US011512313B2

(12) United States Patent
Shapiro et al.

(10) Patent No.: US 11,512,313 B2
(45) Date of Patent: Nov. 29, 2022

(54) FUNCTIONALLY-INTERDEPENDENT SHAPE SWITCHING NUCLEIC ACID NANOPARTICLES

(71) Applicants: The United States of Americans represented by the Secretary, Department of Health and Human Services, Bethesda, MD (US); The University of North Carolina at Charlotte, Charlotte, NC (US)

(72) Inventors: Bruce Allen Shapiro, Gaithersburg, MD (US); Kirill Andreevich Afonin, Charlotte, NC (US); Eckart H. U. Bindewald, Frederick, MD (US); Mathias D. Viard, Frederick, MD (US); Wojciech Kasprzak, Frederick, MD (US); Marina A. Dobrovolskaia, Frederick, MD (US); Justin R. Halman, Charlotte, NC (US)

(73) Assignees: The United States of America, as represented by the Secretary, Department of Health and Human Services, Bethesda, MD (US); The University of North Carolina at Charlote, Charlotte, NC (US)

( * ) Notice: Subject to any disclaimer, the term of this patent is extended or adjusted under 35 U.S.C. 154(b) by 390 days.

(21) Appl. No.: 16/500,765

(22) PCT Filed: Apr. 3, 2018

(86) PCT No.: PCT/US2018/025953
§ 371 (c)(1),
(2) Date: Oct. 3, 2019

(87) PCT Pub. No.: WO2018/187373
PCT Pub. Date: Oct. 11, 2018

(65) Prior Publication Data
US 2020/0199587 A1    Jun. 25, 2020

Related U.S. Application Data

(60) Provisional application No. 62/480,899, filed on Apr. 3, 2017.

(51) Int. Cl.
| C12N 15/113 | (2010.01) |
| A61K 9/14 | (2006.01) |
| A61K 31/7105 | (2006.01) |
| A61K 31/711 | (2006.01) |
| A61K 39/12 | (2006.01) |
| A61K 31/713 | (2006.01) |

(52) U.S. Cl.
CPC .............. *C12N 15/113* (2013.01); *A61K 9/14* (2013.01); *A61K 31/711* (2013.01); *A61K 31/713* (2013.01); *A61K 31/7105* (2013.01); *A61K 39/12* (2013.01)

(58) Field of Classification Search
None
See application file for complete search history.

(56) References Cited

U.S. PATENT DOCUMENTS

| 5,281,781 | A | 1/1994 | Herchenröther et al. |
| 5,466,586 | A | 11/1995 | Davey et al. |
| 5,580,737 | A | 12/1996 | Polisky et al. |
| 5,840,867 | A | 11/1998 | Toole et al. |
| 6,261,783 | B1 | 7/2001 | Jayasena et al. |
| 6,469,158 | B1 | 10/2002 | Usman et al. |
| 6,787,305 | B1 | 9/2004 | Li et al. |
| 10,517,890 | B2 | 12/2019 | Shapiro et al. |
| 2002/0161219 | A1 | 10/2002 | Kanavarioti et al. |
| 2003/0003469 | A1 | 1/2003 | Stinchcomb et al. |
| 2004/0180360 | A1 | 9/2004 | Wilson et al. |
| 2004/0197804 | A1 | 10/2004 | Keefe et al. |
| 2004/0253679 | A1 | 12/2004 | Epstein et al. |
| 2005/0037394 | A1 | 2/2005 | Keefe et al. |
| 2012/0263648 | A1 | 10/2012 | Shapiro et al. |
| 2017/0175122 | A1 | 6/2017 | Guo et al. |
| 2017/0274000 | A1 | 9/2017 | Shapiro et al. |

FOREIGN PATENT DOCUMENTS

| WO | WO 2008/039254 A2 | 4/2008 |
| WO | WO 2010/148085 A1 | 12/2010 |
| WO | WO 2012/125987 A2 | 9/2012 |

(Continued)

OTHER PUBLICATIONS

U.S. Appl. No. 62/480,899, filed Apr. 3, 2017, Shapiro et al.
U.S. Appl. No. 62/623,496, filed Jan. 29, 2018, Dobrovolskaia et al.
U.S. Appl. No. 62/789,033, filed Jan. 7, 2019, Dobrovolskaia et al.
Adlakha-Hutcheon et al., "Controlled destabilization of a liposomal drug delivery system enhances mitoxantrone antitumor activity," *Nature Biotechnology*, 17:775-779 (1999).

(Continued)

*Primary Examiner* — Tracy Vivlemore
(74) *Attorney, Agent, or Firm* — Leydig, Voit & Mayer, Ltd.

(57) ABSTRACT

The description provides a molecular switch comprising at least two nanoparticles, wherein a first nanoparticle comprises DNA and/or RNA oligonucleotides, and a second nanoparticle which is complementary to the first nanoparticle comprises reverse complementary DNA and/or RNA oligonucleotides of the first nanoparticle; wherein the complementary nanoparticles interact under physiological conditions leading to thermodynamically driven conformational changes in the first and second nanoparticles leading to their re-association to release one or more duplexes comprising said DNA and/or RNA oligonucleotides and the reverse complementary DNA and/or RNA oligonucleotides, and wherein the nanoparticles are not rings and have no single stranded toeholds.

20 Claims, 55 Drawing Sheets
Specification includes a Sequence Listing.

(56) References Cited

FOREIGN PATENT DOCUMENTS

| WO | WO 2013/075132 A1 | 5/2013 |
|---|---|---|
| WO | WO 2013/075140 A1 | 5/2013 |
| WO | WO 2014/039809 A2 | 3/2014 |
| WO | WO 2015/042101 A1 | 3/2015 |
| WO | WO 2015/171827 A1 | 11/2015 |
| WO | WO 2017/139758 A1 | 8/2017 |
| WO | WO 2017/197009 A1 | 11/2017 |
| WO | WO 2018/187373 A1 | 10/2018 |
| WO | WO 2019/217576 A1 | 11/2019 |

OTHER PUBLICATIONS

Afonin et al., "Triggering of RNA Interference with RNA-RNA, RNA-DNA, and DNA-RNA Nanoparticles," ACS Nano, 9(1): 251-259 (2015).
Afonin et al., "Computational and Experimental Characterization of RNA Cubic Nanoscaffolds," Methods, 67(2): 256-265 (2014).
Afonin et al., "Multifunctional RNA Nanoparticles," Nano Letters, 14: 5662-5671 (2014).
Afonin et al., "The Use of Minimal RNA Toeholds to Trigger the Activation of Multiple Functionalities," Nano Letters, 16(3): 1746-1753 (2016).
Afonin et al., "In Vitro Assembly of Cubic RNA-Based Scaffolds Designed in silico," Nat. Nanotechnol., 5(9): 676-682 (2010).
Afonin et al., "Activation of different split functionalities upon re-association of RNA-DNA hybrids," Nat. Nanotechnol., 8(4): 296-304 (2013).
Afonin et al., "Co-transcriptional production of RNA-DNA hybrids for simultaneous release of multiple split," Nucleic Acids Research, 42(3): 2085-2097 (2014).
Afonin et al., "Engineered RNA Nanodesigns for Applications in RNA Nanotechnology," RNA Nanotechnology, p. 1-16 (2013).
Afonin, K., "Self-Recognizing Nucleic Acid-Based Shape Switching Nanoparticles: A New Concept of Dynamic RNA Nanotechnology," RNA Nanotechnology Conference held in Berkshire, UK on Aug. 1 -4, 2016.
Andersen et al., "Self-assembly of a nanoscale DNA box with a controllable lid," Nature, 459: 73-77 (2009).
Bath et al., "A Free-Running DNA Motor Powered by a Nicking Enzyme," Angew. Chem. Int. Ed., 44:4358-4361 (2005).
Bindewald et al., "Multistrand Structure Prediction of Nucleic Acid Assemblies and Design of RNA Switches," Nano Letters, 16(3): 1726-1735 (2016).
Blanco et al., "Dendritic cells and cytokines in human inflammatory and autoimmune diseases," Cytokine Growth Factor Rev., 19(1): 41-52 (2008).
Brummelkamp et al., "A System for Stable Expression of Short Interfering RNAs in Mammalian Cells," Science, 296: 550-553 (2002).
Bui et al., "Versatile RNA tetra-U helix linking motif as a toolkit for nucleic acid nanotechnology," Nanomedicine, 13(3): 1137-1146 (2017).
Bujold et al., "Sequence-responsive unzipping DNA cubes with tunable cellular uptake profiles," Chem. Sci., 5: 2449-2455 (2014).
Chelyapov et al., "DNA Triangles and Self-Assembled Hexagonal Tilings," J. Am. Chem. Soc., 126: 13924-13925 (2004).
Chen et al., "An Autonomous DNA Nanomotor Powered by a DNA Enzyme," Angew. Chem. Ind. Ed., 43: 3554-3557 (2004).
Chworos et al., "Building Programmable Jigsaw Puzzles with RNA," Science, 306: 2068-2072 (2004).
Dobrovolskaia et al., "Immunological and hematological toxicities challenging clinical translation of nucleic acid-based therapeutics," Expert Opinion on Biological Therapy, 15(7): 1023-1048 (2015).
Douglas et al., "A Logic-Gated Nanorobot for Targeted Transport of Molecular Payloads," Science, 335(6070): 831-834 (2012).
Elbashir et al., "Duplexes of 21-nucleotide RNAs mediate RNA interference in cultured mammalian cells," Nature, 411: 494-498 (2001).

European Patent Office, International Preliminary Reporton Patentability in International Patent Application No. PCT/US2018/025953, dated Oct. 8, 2019.
European Patent Office, International Search Report in International Patent Application No. PCT/US2018/025953, dsted Aug. 13, 2018.
European Patent Office, Written Opinion in International Patent Application No. PCT/US2018/025953, dated Aug. 13, 2018.
Geary et al., "A single-stranded architecture for cotranscriptional folding of RNA nanostructures," Science, 345(6198): 799-804 (2014).
Grabow et al., "Self-assembling RNA nanorings based on RNAI/II inverse kissing complexes," Nano Letters, 11 (2): 878-887 (2011).
Groves et al., "Computing in mammalian cells with nucleic acid strand exchange," Nat. Nanotechnol., 11 (3):287-294 (2016).
Guo et al., "Inter-RNA Interaction of Phage ø29 pRNA to Form a Hexameric Complex for Viral DNA Transportation," Molecular Cell, 2: 149-155 (1998).
Guo, "The Emerging Field of RNA Nanotechnology," Nat. Nanotechnol., 5(12): 833-842 (2010).
Halman et al., "Functionally-interdependent shape-switching nanoparticles with controllable properties," Nucleic Acids Research, 45(4):2210-2220 (2017).
Halman et al., "Functionally-interdependent shape-switching nanoparticles with controllable properties," Nucleic Acids Research, 45(4): 2210-2220 (2017) (Supporting Information).
Hannon, "RNA interference," Nature, 418:244-251 (2002).
Haque et al., "Ultrastable synergistic tetravalent RNA nanoparticles for targeting to cancers," Nano Today, 7(4): 245-257 (2012).
Haseloff et al., "Simple RNA enzymes with new and highly specific endoribonuclease activities," Nature, 334:585-591 (1988).
He et al., "Hierarchial self-assembly of DNA into symmetric supramolecular polyhedral," Nature, 452:198-201 (2008).
Hutvágner et al., "RNAi: nature abhors a double-strand," Current Opinion in Genetics & Development, 12:225-232 (2002).
Jaeger et al., "The architectonics of programmable RNA and DNA nanostructures," Current Opinion in Structural Biology, 16: 531-543 (2006).
Jimenez et al., "Chemistry and biology of self-cleaving ribozymes," Trends Biochem. Sci., 40(11): 648-661 (2015).
Kaur et al., "Thermodynamic, Counterion, and Hydration Effects for the Incorporation of Locked Nucleic Acid Nucleotides into DNA Duplexes," Biochemistry, 45: 7347-7355 (2006).
Khaled et al., "Controllable Self-Assembly of Nanoparticles for Specific Delivery of Multiple Therapeutic Molecules to Cancer Cells Using RNA Nanotechnology," Nano Letters, 5(9): 1797-1808 (2005).
Khisamutdinov et al., "RNA as a Boiling-Resistant Anionic Polymer Material to Build Robust Structures with Defined Shape and Stoichiometry," ACS Nano, 8(5): 4771-4781 (2014).
Lee et al., "Expression of small interfering RNAs targeted against HIV-1 rev transcripts in human cells," Nature Biotechnology, 19: 500-505 (2002).
Lee et al., "Molecularly Self-Assembled Nucleic Acid Nanoparticles for Targeted In Vivo siRNA Delivery," Nat. Nanotechnol., 7(6): 389-393 (2012).
Lund et al., "Molecular Robots Guided by Prescriptive Landscapes," Nature, 465(7295): 206-210 (2010).
Mao et al., "A nanomechanical device based on the B-Z transition of DNA," Nature, 397: 144-146 (1999).
Mathieu et al., "Six-Helix Bundles Designed from DNA," Nano Letters, 5(4): 661-665 (2005).
McCaffrey et al., "RNA interference in adult mice," Nature, 418: 38-39 (2002).
Meyer et al., "Cationic Liposomes Coated with Polyethylene Glycol as Carriers for Oligonucleotides," The Journal of Biological Chemistry, 273(25): 15621-15627 (1998).
Mironov et al., "Sensing Small Molecules by Nascent RNA: A Mechanism to Control Transcription in Bacteria," Cell, 111: 747-756 (2002).
Miyagishi et al., "U6promoter-driven siRNAs with four uridine 3' overhangs efficiently suppress targeted gene expression in mammalian cells," Nature Biotechnology, 19: 497-500 (2002).

(56) References Cited

OTHER PUBLICATIONS

Modi et al., "A DNA nanomachine that maps spatial and temporal pH changes inside living cells," *Nature Nanotechnology*, 4: 325-330 (2009).
Modi et al., "Two DNA nanomachines map pH changes along intersecting endocytic pathways inside the same cell," *Nature Nanotechnology*, 8: 459-467 (2013).
Oh et al., "siRNA delivery systems for cancer treatment," *Advanced Drug Delivery Reviews*, 61: 850-862 (2009).
Ohno et al., "Synthetic RNA-protein complex shaped like an equilateral triangle," *Nature Nanotechnology*, 6: 116-120 (2011).
Osada et al., "Engineering RNA—Protein Complexes with Different Shapes for Imaging and Therapeutic Applications," *ACS Nano*, 8(8):8130-8140 (2014).
Paddison et al., "Short hairpin RNAs (shRNAs) induce sequence-specific silencing in mammalian cells," *Genes & Development*, 16:948-958 (2002).
Papahadjopoulos et al., "Sterically stabilized liposomes: Improvements in pharmacokinetics and antitumor therapeutic efficacy," *Proc. Natl. Acad. Sci. USA*, 88: 11460-11464(1991).
Paul et al., "Effective expression of small interfering RNA in human cells," *Nature Biotechnology*, 29: 505-508 (2002).
Pinheiro et al., "Challenges and opportunities for structural DNA nanotechnology," *Nat. Nanotechnol.*, 6(12): 763-772 (2011).
Righetti et al., "Temperature-responsive in vitro RNA structurome of *Yersinia pseudotuberculosis*," *PNAS*, 113(26): 7237-7242 (2016).
Rothemund, "Folding DNA to create nanoscale shapes and patterns," *Nature*, 440: 297-302 (2006).
Sharp, "RNA interference—2001," *Genes & Development*, 15: 485-490 (2001).
Shin et al., "A Synthetic DNA Walker for Molecular Transport," *J. Am. Chem. Soc.*, 126: 10834-10835 (2004).
Sui et al., "A DNA vector-based RNAi technology to suppress gene expression in mammalian cells," *PNAS*, 99(8): 5515-5520 (2002).
Takanohashi et al., "Elevation of proinflammatory cytokines in patients with Aicardi-Goutières syndrome," *Neurology*, 80: 997-1002 (2013).
Turner et al., "Cytokines and chemokines: At the crossroads of cell signaling and inflammatory disease," *Biochimica et Biophysica Acta*, 1843: 2563-2582 (2014).
Tuschl, "RNA Interference and Small Interferring RNAs," *ChemBioChem*, 2: 239-245 (2001).
Wang et al., "Self-assembled triangular DNA nanoparticles are an efficient system for gene delivery," *Journal of Controlled Release*, 233: 126-135 (2016).
Whitehead et al., "Knocking down barriers: advances in siRNA delivery," *Nature Reviews: Drug Discovery*, 8: 129-138 (2009).
Winkler et al., "An mRNA structure that controls gene expression by binding FMN," *PNAS*, 99(25): 15908-15913 (2002).
Yingling et al., "Computational Design of an RNA Hexagonal Nanoring and an RNA Nanotube," *Nano Letters*, 7(8):2328-2334 (2007).
Yu et al., "De novo design of an RNA tile that self-assembles into a homo-octameric nanoprism," *Nature Communications*, 6: 5724 (2015).
Yu et al., "RNA interference by expression of short-interferring RNAs and hairpin RNAs in mammalian cells," *PNAS*, 99(9): 6047-6052 (2002).
Yurke et al., "A DNA-fuelled molecular machine made of DNA," *Nature*, 406: 605-608 (2000).
Zamanian-Daryoush et al., "Determinants of Cytokine Induction by Small Interfering RNA in Human Peripheral Blood Mononuclear Cells," *Journal of Interferon & Cytokine Research*, 28: 221-233 (2008).
Zamore et al., "RNAi: Double-Stranded RNA Directs the ATP-Dependent Cleavage of mRNA at 21 to 23 Nucleotide Intervals," *Cell*, 101: 25-33 (2000).
Zhou et al., "A Light-Driven DNA Nanomachine for the Efficient Photoswitching of RNA Digestion," *Angew. Chem. Ind. Ed.*, 49: 2167-2170 (2010).

F

G

E

| cube composition | Tm°C | ± SD |
|---|---|---|
| 6DNAs cube | 35.9 | 0.5 |
| 5DNAs/1RNA cube | 37.1 | 0.4 |
| 4DNAs/2RNAs cube | 39.9 | 0.3 |
| 3DNAs/3RNAs cube | 40.7 | 1.1 |
| 2DNAs/4RNAs cube | 49.8 | 0.2 |
| 1DNA/5RNA cube | 56.6 | 0.2 |
| 6RNAs cube | 59.8 | 0.2 |
| 6DNAs anticube | 36.2 | 0.5 |
| 6RNAs anticube | 68.0 | 1.3 |

FIG. 7 (cont'd)

| Cube composition | Predicted Tm (°C) | Measured Tm (°C) |
|---|---|---|
| 6DNAs cube | 35.2 | 35.9 |
| 5DNAs/1RNA cube | 35.6 | 37.1 |
| 4DNAs/2RNAs cube | 40.0 | 39.9 |
| 3DNAs/3RNAs cube | 39.0 | 40.7 |
| 2DNAs/4RNAs cube | 44.6 | 49.8 |
| 1DNA/5RNAs cube | 48.1 | 56.6 |
| 6 RNAs cube | 56.2 | 59.8 |
| 6 DNAs anticube | 36.0 | 36.2 |

C

B

DNA cube with three Ts at each corner
dA
5'-GGCAACTTTGATCCCTCGGTTTAGCGCCGGCCTTTTCTCCCACACTTTCACG [SEQ ID NO: 1]
dB
5'-GGGAAATTTCGTGGTAGGTTTTGTTGCCCGTGTTTCTACGATTACTTTGGTC [SEQ ID NO: 2]
dC
5'-GGACATTTTCGAGACAGCATTTTTTCCCGACCTTTGCGGATTGTATTTTAGG [SEQ ID NO: 3]
dD
5'-GGCGCTTTTGACCTTCTGCTTTATGTCCCCTATTTCTTAATGACTTTTGGCC [SEQ ID NO: 4]
dE
5'-GGGAGATTTAGTCATTAAGTTTTACAATCCGCTTTGTAATCGTAGTTTGTGT [SEQ ID NO: 5]
dF
5'-GGGATCTTTACCTACCACGTTTTGCTGTCTCGTTTGCAGAAGGTCTTTCCGA [SEQ ID NO: 6]

Fluorescently labeled DNA cube strand
dD-Alexa 488
5'-GGCGCTTTTGACCTTCTGCTTTATGTCCCCTATTTCTTAATGACTTTTGGCC-Alexa 488 [SEQ ID NO: 7]

DNA anti-cube with three As at each corner
anti-dA
5'-CGTGAAAGTGTGGGAGAAAAGGCCGGCGCTAAACCGAGGGATCAAAGTTGCC [SEQ ID NO: 8]
anti-dB
5'-GACCAAAGTAATCGTAGAAACACGGGCAACAAAACCTACCACGAAATTTCCC [SEQ ID NO: 9]
anti-dC
5'-CCTAAAATACAATCCGCAAAGGTCGGGAAAAAATGCTGTCTCGAAAATGTCC [SEQ ID NO: 10]
anti-dD
5'-GGCCAAAAGTCATTAAGAAATAGGGGACATAAAGCAGAAGGTCAAAAGCGCC [SEQ ID NO: 11]
anti-dE
5'-ACACAAACTACGATTACAAAGCGGATTGTAAAACTTAATGACTAAATCTCCC [SEQ ID NO: 12]
anti-dF
5'-TCGGAAAGACCTTCTGCAAACGAGACAGCAAAACGTGGTAGGTAAAGATCCC [SEQ ID NO: 13]

Fluorescently labeled anti-DNA cube strand
anti-dA-Cy5
5'-CGTGAAAGTGTGGGAGAAAAGGCCGGCGCTAAACCGAGGGATCAAAGTTGCC-Cy5 [SEQ ID NO: 14]

RNA cube with three Us at each corner[2]
rA
5'-GGCAACUUUGAUCCCUCGGUUUAGCGCCGGCCUUUUCUCCCACACUUUCACG [SEQ ID NO: 15]
rB
5'-GGGAAAUUUCGUGGUAGGUUUUGUUGCCCGUGUUUCUACGAUUACUUUGGUC [SEQ ID NO: 16]
rC
5'-GGACAUUUUCGAGACAGCAUUUUUUCCCGACCUUUGCGGAUUGUAUUUUAGG [SEQ ID NO: 17]
rD
5'-GGCGCUUUUGACCUUCUGCUUUAUGUCCCCUAUUUCUUAAUGACUUUUGGCC [SEQ ID NO: 18]
rE
5'-GGGAGAUUUAGUCAUUAAGUUUUACAAUCCGCUUUGUAAUCGUAGUUUGUGU [SEQ ID NO: 19]
rF
5'-GGGAUCUUUACCUACCACGUUUUGCUGUCUCGUUUGCAGAAGGUCUUUCCGA [SEQ ID NO: 20]

FIG. 18

Fluorescently labeled RNA cube strand
rD-Alexa 488
5'-GGCGCUUUUGACCUUCUGCUUUAUGUCCCCUAUUUCUUAAUGACUUUUGGCC-Alexa 488 [SEQ ID NO: 21]

DNA cube with three Ts at each corner and with T7RNA polymerase promoter
dA-T7
5'TTCTAATACgACTCACTATAGGCAACTTTGATCCCTCGGTTTAGCGCCGGCCTTTTCTCCCACACTTTCACG
[SEQ ID NO: 22]
dB-T7
5'TTCTAATACgACTCACTATAGGGAAATTTCGTGGTAGGTTTTGTTGCCCGTGTTTCTACGATTACTTTGGTC
[SEQ ID NO: 23]
dC-T7
5'TTCTAATACgACTCACTATAGGACATTTTCGAGACAGCATTTTTTCCCGACCTTTGCGGATTGTATTTTAGG
[SEQ ID NO: 24]
dD-T7
5'TTCTAATACgACTCACTATAGGCGCTTTTGACCTTCTGCTTTATGTCCCCTATTTCTTAATGACTTTTGGCC
[SEQ ID NO: 25]
dE-T7
5'TTCTAATACgACTCACTATAGGGAGATTTAGTCATTAAGTTTTACAATCCGCTTTGTAATCGTAGTTTGTGT
[SEQ ID NO: 26]
dF-T7
5'TTCTAATACgACTCACTATAGGGATCTTTACCTACCACGTTTTGCTGTCTCGTTTGCAGAAGGTCTTTCCGA
[SEQ ID NO: 27]

Complementary strand for split T7 promoter carrying cubes
5'-TATAGTGAGTCGTATTAGAA [SEQ ID NO: 28]

Truncated strand for split T7 promoter carrying cubes with Alexa 488
5'-ATAGTGAGTCG/3AlexF488N/ [SEQ ID NO: 29]

DNA anticube with three As at each corner with T7RNA polymerase promoter
anti-dA-T7
5'CGTGAAAGTGTGGGAGAAAAGGCCGGCGCTAAACCGAGGGATCAAAGTTGCCTATAGTGAGTCGTATTAGAA
[SEQ ID NO: 30]
anti-dB-T7
5'GACCAAAGTAATCGTAGAAACACGGGCAACAAAACCTACCACGAAATTTCCCTATAGTGAGTCGTATTAGAA
[SEQ ID NO: 31]
anti-dC-T7
5'CCTAAAATACAATCCGCAAAGGTCGGGAAAAAATGCTGTCTCGAAAATGTCCTATAGTGAGTCGTATTAGAA
[SEQ ID NO: 32]
anti-dD-T7
5'GGCCAAAAGTCATTAAGAAATAGGGGACATAAAGCAGAAGGTCAAAAGCGCCTATAGTGAGTCGTATTAGAA
[SEQ ID NO: 33]
anti-dE-T7
5'ACACAAACTACGATTACAAAGCGGATTGTAAAACTTAATGACTAAATCTCCCTATAGTGAGTCGTATTAGAA
[SEQ ID NO: 34]
anti-dF-T7
5'TCGGAAAGACCTTCTGCAAACGAGACAGCAAAACGTGGTAGGTAAAGATCCCTATAGTGAGTCGTATTAGAA
[SEQ ID NO: 35]

FIG. 18 (cont'd)

Complementary strand for split T7 promoter carrying anti-cubes
5'-TTCTAATACgACTCACTATA [SEQ ID NO: 36]

Truncated strand for split T7 promoter carrying anti-cubes with Alexa 546
5'-/5AlexF546N/CgACTCACTAT [SEQ ID NO: 37]

Split F30 BROC-COLI aptamer
(5'-gggaa starting sequences were added for in vitro transcription)
F30 broccoli[14]
5'gggaaagUUGCCAUGUGUAUGUGGGAGACGGUCGGGUCCAGAUAUUCGUAUCUGUCGAGUAGAGUGUGGGCUCCC
ACAUACUCUGAUGAUCCUUCGGGAUCAUUCAUGGCAA [SEQ ID NO: 38]
Split aptamer:
BROC
5'gggaaaUUGCCAUGUGUAUGUGGGAGACGGUCGGGUCCAGAUAUU [SEQ ID NO: 39]
COLI
5'gggaaaCGUAUCUGUCGAGUAGAGUGUGGGCUCCCACAUACUCUGAUGAUCCUUCGGGAUCAUUCAUGGCAA
[SEQ ID NO: 40]

RNA cube with three Us at each corner and BROC to form fibers with embedded
aptamers on re-association with anti-cubes
(5'-gggaa starting sequences were added for in vitro transcription)
rA_BROC_fiber
5'gggaaUUGCCAUGUGUAUGUGGGAGACGGUCGGGUCCAGAUAUUGGCAACUUUGAUCCCUCGGUUUAGCGCCGGC
CUUUUCUCCCACACUUUCACG [SEQ ID NO: 41]
rB_BROC_fiber
5'gggaaUUGCCAUGUGUAUGUGGGAGACGGUCGGGUCCAGAUAUUGGGAAAUUUCGUGGUAGGUUUUGUUGCCCGU
GUUUCUACGAUUACUUUGGUC [SEQ ID NO: 42]
rC_BROC_fiber
5'gggaaUUGCCAUGUGUAUGUGGGAGACGGUCGGGUCCAGAUAUUGGACAUUUUCGAGACAGCAUUUUUUCCCGAC
CUUUGCGGAUUGUAUUUAGG [SEQ ID NO: 43]
rD_BROC_fiber
5'gggaaUUGCCAUGUGUAUGUGGGAGACGGUCGGGUCCAGAUAUUGGCGCUUUUGACCUUCUGCUUUAUGUCCCCU
AUUUCUUAAUGACUUUUGGCC [SEQ ID NO: 44]
rE_BROC_fiber_terminal
5'gggaaUUGCCAUGUGUAUGUGGGAGACGGUCGGGUCCAGAUAUUGGGAGAUUUAGUCAUUAAGUUUUACAAUCCG
CUUUGUAAUCGUAGUUUGUGUUUGCCAUGUGUAUGUGGGAGACGGUCGGGUCCAGAUAUU [SEQ ID NO: 45]

FIG. 18 (cont'd)

RNA anti-cube with three As at each corner and COLI
(5'-gggaa starting sequences were added for in vitro transcription)
anti-rA_COLI
5'gggaaCGUAUCUGUCGAGUAGAGUGUGGGCUCCCACAUACUCUGAUGAUCCUUCGGGAUCAUUCAUGGCAACGUG
AAAGUGUGGGAGAAAAGGCCGGCGCUAAACCGAGGGAUCAAAGUUGCC [SEQ ID NO: 46]
anti-rB_COLI
5'gggaaCGUAUCUGUCGAGUAGAGUGUGGGCUCCCACAUACUCUGAUGAUCCUUCGGGAUCAUUCAUGGCAAGACC
AAAGUAAUCGUAGAAACACGGGCAACAAAACCUACCACGAAAUUUCCC [SEQ ID NO: 47]
anti-rC_COLI
5'gggaaCGUAUCUGUCGAGUAGAGUGUGGGCUCCCACAUACUCUGAUGAUCCUUCGGGAUCAUUCAUGGCAACCUA
AAAUACAAUCCGCAAAGGUCGGGAAAAAAUGCUGUCUCGAAAAUGUCC [SEQ ID NO: 48]
anti-rD_COLI
5'gggaaCGUAUCUGUCGAGUAGAGUGUGGGCUCCCACAUACUCUGAUGAUCCUUCGGGAUCAUUCAUGGCAAGGCC
AAAAGUCAUUAAGAAAUAGGGGACAUAAAGCAGAAGGUCAAAAGCGCC [SEQ ID NO: 49]
anti-rE_COLI
5'gggaaCGUAUCUGUCGAGUAGAGUGUGGGCUCCCACAUACUCUGAUGAUCCUUCGGGAUCAUUCAUGGCAAACAC
AAACUACGAUUACAAAGCGGAUUGUAAAACUUAAUGACUAAAUCUCCC [SEQ ID NO: 50]
anti-rF_COLI
5'gggaaCGUAUCUGUCGAGUAGAGUGUGGGCUCCCACAUACUCUGAUGAUCCUUCGGGAUCAUUCAUGGCAAUCGG
AAAGACCUUCUGCAAACGAGACAGCAAAACGUGGUAGGUAAAGAUCCC [SEQ ID NO: 51]

DNA cubes and anti-cubes designed to release DS RNA against GFP[15] upon re-association.

DNA cube with three Ts at each corner carrying sense DS RNA (GFP)
dA-DS GFP
5'CGGTGGTGCAGATGAACTTCAGGGTCAttGGCAACTTTGATCCCTCGGTTTAGCGCCGGCCTTTTCTCCCACACT
TTCACG [SEQ ID NO: 52]
dB- DS GFP
5'CGGTGGTGCAGATGAACTTCAGGGTCAttGGGAAATTTCGTGGTAGGTTTTGTTGCCCGTGTTTCTACGATTACT
TTGGTC [SEQ ID NO: 53]
dC- DS GFP
5'CGGTGGTGCAGATGAACTTCAGGGTCAttGGACATTTTCGAGACAGCATTTTTTCCCGACCTTTGCGGATTGTAT
TTTAGG [SEQ ID NO: 54]
dD- DS GFP
5'CGGTGGTGCAGATGAACTTCAGGGTCAttGGCGCTTTTGACCTTCTGCTTTATGTCCCCTATTTCTTAATGACTT
TTGGCC [SEQ ID NO: 55]
dE- DS GFP
5'CGGTGGTGCAGATGAACTTCAGGGTCAttGGGAGATTTAGTCATTAAGTTTTACAATCCGCTTTGTAATCGTAGT
TTGTGT [SEQ ID NO: 56]
dF- DS GFP
5'CGGTGGTGCAGATGAACTTCAGGGTCAttGGGATCTTTACCTACCACGTTTTGCTGTCTCGTTTGCAGAAGGTCT
TTCCGA [SEQ ID NO: 57]

FIG. 18 (cont'd)

DNA anti-cube with three As at each corner carrying antisense DS RNA (GFP)
anti-dA-antisense DS GFP
5'CGTGAAAGTGTGGGAGAAAAGGCCGGCGCTAAACCGAGGGATCAAAGTTGCCaaTGACCCTGAAGTTCATCTGCA
CCACCG [SEQ ID NO: 58]
anti-dB-antisense DS GFP
5'GACCAAAGTAATCGTAGAAACACGGGCAACAAAACCTACCACGAAATTTCCCaaTGACCCTGAAGTTCATCTGCA
CCACCG [SEQ ID NO: 59]
anti-dC-antisense DS GFP
5'CCTAAAATACAATCCGCAAAGGTCGGGAAAAAATGCTGTCTCGAAAATGTCCaaTGACCCTGAAGTTCATCTGCA
CCACCG [SEQ ID NO: 60]
anti-dD-antisense DS GFP
5'GGCCAAAAGTCATTAAGAAATAGGGGACATAAAGCAGAAGGTCAAAAGCGCCaaTGACCCTGAAGTTCATCTGCA
CCACCG [SEQ ID NO: 61]
anti-dE-antisense DS GFP
5'ACACAAACTACGATTACAAAGCGGATTGTAAAACTTAATGACTAAATCTCCCaaTGACCCTGAAGTTCATCTGCA
CCACCG [SEQ ID NO: 62]
anti-dF-antisense DS GFP
5'TCGGAAAGACCTTCTGCAAACGAGACAGCAAAACGTGGTAGGTAAAGATCCCaaTGACCCTGAAGTTCATCTGCA
CCACCG [SEQ ID NO: 63]

DS RNA against GFP[15]
DS RNA sense
5'-pACCCUGAAGUUCAUCUGCACCACCG [SEQ ID NO: 64]
DS RNA antisense
5'-CGGUGGUGCAGAUGAACUUCAGGGUCA [SEQ ID NO: 65]

Fluorescently labeled RNA
DS RNA sense 3`-end labeled with Alexa488
5'-pACCCUGAAGUUCAUCUGCACCACCG-Alexa488 [SEQ ID NO: 66]
DS RNA antisense 5`-end labeled with Alexa546
5'-Alexa546-CGGUGGUGCAGAUGAACUUCAGGGUCA [SEQ ID NO: 67]

DNA cubes and anti-cubes designed to release DS RNA against PLK1 and BCL-2
upon re-association DNA cube with three Ts at each corner carrying sense DS RNA
dA-DS PLK1 sense
5'TCGTCATTAAGCAGCTCGTTAATGGTttGGCAACTTTGATCCCTCGGTTTAGCGCCGGCCTTTTCTCCCACACTT
TCACG [SEQ ID NO: 68]
dB-DS BCL2 sense
5'CTGCGACAGCTTATAATGGATGTACTTttGGGAAATTTCGTGGTAGGTTTTGTTGCCCGTGTTTCTACGATTACT
TTGGTC [SEQ ID NO: 69]

DNA anti-cube with three As at each corner carrying antisense DS RNA
anti-dA DS PLK1 antisense
5'CGTGAAAGTGTGGGAGAAAAGGCCGGCGCTAAACCGAGGGATCAAAGTTGCCaaACCATTAACGAGCTGCTTAAT
GACGA [SEQ ID NO: 70]
anti-dB DS BCL2 antisense
5'GACCAAAGTAATCGTAGAAACACGGGCAACAAAACCTACCACGAAATTTCCCaaaaGTACATCCATTATAAGCTG
TCGCAG [SEQ ID NO: 71]

FIG. 18 (cont'd)

DS RNA against PLK1 designed based on the validate siRNA sequences[16]
DS RNA sense
5'- pCCAUUAACGAGCUGCUUAAUGACGA [SEQ ID NO: 72]
DS RNA antisense
5'-UCGUCAUUAAGCAGCUCGUUAAUGGUU [SEQ ID NO: 73]

DS RNA against BCL2 designed based on the validate siRNA sequences[17]
DS RNA sense
5'-pGUACAUCCAUUAUAAGCUGUCGCAG [SEQ ID NO: 74]
DS RNA antisense
5'-CUGCGACAGCUUAUAAUGGAUGUACUU [SEQ ID NO: 75]

Ring/Anti-ring nanoparticles

RNA ring[18]
nrA
5'-GGGAACCGUCCACUGGUUCCCGCUACGAGAGCCUGCCUCGUAGC [SEQ ID NO: 76]
nrB
5'-GGGAACCGCAGGCUGGUUCCCGCUACGAGAGAACGCCUCGUAGC [SEQ ID NO: 77]
nrC
5'-GGGAACCGCGUUCUGGUUCCCGCUACGAGACGUCUCCUCGUAGC [SEQ ID NO: 78]
nrD
5'-GGGAACCGAGACGUGGUUCCCGCUACGAGUCGUGGUCUCGUAGC [SEQ ID NO: 79]
nrE
5'-GGGAACCACCACGAGGUUCCCGCUACGAGAACCAUCCUCGUAGC [SEQ ID NO: 80]
nrF
5'-GGGAACCGAUGGUUGGUUCCCGCUACGAGAGUGGACCUCGUAGC [SEQ ID NO: 81]

RNA anti-ring
(5'-gggaa starting sequences were added for in vitro transcription)
nrA
5'-gggaaGCUACGAGGCAGGCUCUCGUAGCGGGAACCAGUGGACGGUUCCC [SEQ ID NO: 82]
nrB
5'-gggaaGCUACGAGGCGUUCUCUCGUAGCGGGAACCAGCCUGCGGUUCCC [SEQ ID NO: 83]
nrC
5'-gggaaGCUACGAGGAGACGUCUCGUAGCGGGAACCAGAACGCGGUUCCC [SEQ ID NO: 84]
nrD
5'-gggaaGCUACGAGACCACGACUCGUAGCGGGAACCACGUCUCGGUUCCC [SEQ ID NO: 85]
nrE
5'-gggaaGCUACGAGGAUGGUUCUCGUAGCGGGAACCUCGUGGUGGUUCCC [SEQ ID NO: 86]
nrF

FIG. 18 (cont'd)

DNA anti-nanoring with T7RNA POL PROMOTER
Anti-nrA-T7
5'GCTACGAGGCAGGCTCTCGTAGCGGGAACCAGTGGACGGTTCCCTATAGTGAGTCGTATTAGAA [SEQ ID NO: 87]
Anti-nrB-T7
5'GCTACGAGGCGTTCTCTCGTAGCGGGAACCAGCCTGCGGTTCCCTATAGTGAGTCGTATTAGAA [SEQ ID NO: 88]
Anti-nrC-T7
5'GCTACGAGGAGACGTCTCGTAGCGGGAACCAGAACGCGGTTCCCTATAGTGAGTCGTATTAGAA [SEQ ID NO: 89]
Anti-nrD-T7
5'GCTACGAGACCACGACTCGTAGCGGGAACCACGTCTCGGTTCCCTATAGTGAGTCGTATTAGAA [SEQ ID NO: 90]
Anti-nrE-T7
5'GCTACGAGGATGGTTCTCGTAGCGGGAACCTCGTGGTGGTTCCCTATAGTGAGTCGTATTAGAA [SEQ ID NO: 91]
Anti-nrF-T7
5'GCTACGAGGTCCACTCTCGTAGCGGGAACCAACCATCGGTTCCCTATAGTGAGTCGTATTAGAA [SEQ ID NO: 92]

Triangle/Anto-triangel nanoparticles
RNA triangle
rA
5'GGAUGCUGGUACUUUUGAAACAUUUCGAGUCGCGAGGGUUUUCCCAUCGUUGGCCCGUAUCGCGUUUUCUUAUGAAGA [SEQ ID NO: 93]
rB
5'-GGUCGCGACCUUCUUUUCCCUCGCGACUCGAAAUGUUUCUUUUCGAGGUCGCCC [SEQ ID NO: 94]
rC
5'-GGAUCUUUCGCCUUUUCGCGAUACGGGCCAACGAUGGGUUUUGAAGGUCGCGAC [SEQ ID NO: 95]
rD
5'-GGGCGACCUCGUUUUGUACCAGCAUCCUCUUCAUAAGUUUUGGCGAAAGAUCC [SEQ ID NO: 96]

DNA triangle
dA
5'GGATGCTGGTACTTTTGAAACATTTCGAGTCGCGAGGGTTTTCCCATCGTTGGCCCGTATCGCGTTTTCTTATGAAGA [SEQ ID NO: 97]
dB
5'-GGTCGCGACCTTCTTTTCCCTCGCGACTCGAAATGTTTCTTTTCGAGGTCGCCC [SEQ ID NO: 98]
dC
5'-GGATCTTTCGCCTTTTCGCGATACGGGCCAACGATGGGTTTTGAAGGTCGCGAC [SEQ ID NO: 99]
dD
5'-GGGCGACCTCGTTTTGTACCAGCATCCTCTTCATAAGTTTTGGCGAAAGATCC [SEQ ID NO: 100]

FIG. 18 (cont'd)

```
DNA anti-triangle
Anti-dA
5'TCTTCATAAGAAAAGGCGATACGGGCCAACGATGGGAAAACCCTCGCGACTCGAAATGTTTCAAAAGTACCAGCA
TCC [SEQ ID NO: 101]
Anti-dB
5'-GGGCGACCTCGAAAAGAAACATTTCGAGTCGCGAGGGAAAAGAAGGTCGCGACC [SEQ ID NO: 102]
Anti-dC
5'-TCGCGACCTTCAAAACCCATCGTTGGCCCGTATCGCCAAAACGCGAAAGATCC [SEQ ID NO: 103]
Anti-dD
5'-GATCTTTCGCGAAAACTTATGAAGAGGATGCTGGTACAAAACGAGGTCGCCC [SEQ ID NO: 104]
```

FIG. 18 (cont'd)

FUNCTIONALLY-INTERDEPENDENT SHAPE SWITCHING NUCLEIC ACID NANOPARTICLES

CROSS-REFERENCE TO RELATED APPLICATIONS

This patent application is a U.S. National Phase Patent Application of International Patent Application No. PCT/US2018/025953, filed Apr. 3, 2018, which claims the benefit of U.S. Provisional Patent Application No. 62/480,899, filed Apr. 3, 2017, both of which are hereby incorporated by reference in their entireties.

STATEMENT REGARDING FEDERALLY SPONSORED RESEARCH AND DEVELOPMENT

This invention was made with Government support under project numbers ZIA BC00838234 and ZIA BC01106110 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 25,292 Byte ASCII (Text) file named "744889_ST25.txt," dated Sep. 30, 2019.

RELATED APPLICATIONS AND INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND OF THE INVENTION

Nucleic acids (RNA and DNA) have been acknowledged as a premiere building material for nanotechnology due to their biocompatibility and programmability. The option of both canonical and non-canonical base pairings tremendously expands the diverse set of RNA and DNA structural motifs available as building blocks (1-13). The programmable multitasking as well as the ability to dynamically respond to the environment makes nucleic acids an attractive material for tailor-made applications in both biotechnology and personalized therapy.

In recent decades, a wide array of artificially designed dynamic DNA assemblies have been shown to respond to a broader spectrum of physicochemical stimuli or ligands. Rationally designed DNA nanomachines can carry out a rotary motion by switching from B- to Z-DNA in increased ionic strength (14), sense the pH (15, 16), and respond to the changes from visible to UV light (17). DNA "walkers" are capable of directional movement based on strand displacement (18, 19), enzymatic activity (20, 21), or in accordance with the prescriptive DNA origami landscapes (22). DNA boxes with a programmable lid (23) and DNA "nanorobots" (24) can be used for delivery and release of different cargos.

Recently, a DNA cube that selectively forms a flat 2D structure after hybridization to fusion gene that is characteristic for a prostate cancer cell line was engineered. Although authors have demonstrated that the cubes are taken up by a number of cell lines, the dynamic response has only been shown in vitro (25). Although, numerous creative innovations of dynamic DNA nanoassemblies have been described, the majority are, however, only functional in vitro and their immediate practical applications in living systems remain unclear.

In addition to being a carrier of genetic information, RNAs are now being recognized to function as scaffolds, enzymes, switches, aptamers, as well as regulators of gene expression. The emerging field of RNA nanotechnology applies the current knowledge related to the structure and function of natural and artificial classes of RNAs to further address specific biomedical challenges by engineering nanodevices that can interact with cellular machinery (2).

While RNA interference (RNAi) continues to hold incredible potential, numerous challenges associated with the application of RNAi technology must be addressed before it can be made into a viable therapy. The most prominent include transporting, targeting, and stabilizing short interfering RNAs (siRNAs) into tumor cells after injection into a patient's bloodstream. One of the most promising set of solutions to date includes the use of various types of nanoparticles (NPs) (Whitehead et al. 2009; Oh and Park 2009).

The rapidly expanding field of nanobiology opens up the possibilities for the development of new methods and compositions that can be used for the diagnosis, prognosis, and treatment of a multitude of diseases and conditions. However, while an increasing number of novel drugs and therapeutic agents are being discovered, the problem of delivering them specifically to the desired site or cell has not been solved. RNA nanoparticles have been shown to be able to carry multiple components, including molecules for specific cell recognition, image detection, and therapeutic treatment. The use of such protein-free nanoparticles holds the promise for the repeated long-term treatment of chronic diseases with low immune response and should avoid the problems of short retention time of small molecules and the difficulty of delivery of particles larger than 100 nanometers.

For example, NPs can provide several distinct advantages toward the advancement of RNAi therapeutics. For instance, they have been shown to produce a nanoparticle effect that improves cellular uptake. Moreover, NPs offer an increased degree of protection against ribonuclease degradation while also accommodating additional functional groups like aptamers to aid cellular targeting.

While a broad range of materials have been used in RNAi nanotechnology, including some exotic synthetic materials, unmodified RNA nucleotides that serve as both the therapeutic and the structural core of NPs are thought to provide unique advantages. For example, the use of natural RNA nucleotides—in addition to RNA's biocompatibility—takes advantage of RNA's inherent ability to self-assemble and spatially arrange multiple siRNAs, RNA or DNA aptamers, flourescent dyes, small molecules, RNA-DNA hybrids with split functionalities, and proteins. Furthermore, NPs made of unmodified nucleotides can be synthesized directly via run-off transcription, making their ease of synthesis and cost of production attractive for scaled-up production.

Formation of functional RNA NPs has been previously described and can take place either with one-pot assembly or directly with T7 RNA polymerase transcription reactions when equimolar amounts of DNA templates encoding specifically designed RNAs that are part of the composition of the functional RNA NPs (see, e.g. PCT/US2013/058492, incorporated by reference in its entirety herein).

Building dynamic RNA nanoparticles that can communicate with one another will further improve the operation of functional systems. In fact, metabolite and cofactor responsive riboswitches and ribozymes or temperature sensing RNA thermometers are examples of dynamic RNAs autogenic in nature (26-29). Recently, two approaches of dynamic RNA (30) and RNA-DNA hybrid (31) nanostructures that conditionally activate gene silencing in diseased cells in vitro and in vivo were reported. The first approach is based on computer-generated two-stranded RNA switches that are activated only in the presence of specific mRNAs through interaction with a single-stranded (ss) RNA toehold of the switch (30). The second approach is based on RNA-DNA hybrids with split-functionalities activated only when two complementary copies are introduced into the same cell. Strand exchange, with subsequent intracellular activation of functionalities, is promoted by the interaction of complementary ssDNA (31) or ssRNA (32) toeholds. This concept was further used by other research groups for various applications (33). The simultaneous delivery and release of multiple functionalities was achieved by including them all into the longer hybrids (34). Alternatively, RNA and/or DNA nanoscaffolds can be decorated with multiple hybrids and activated by adding individual cognate DNA/RNA strands hybrids (35, 36). This approach requires, however, the simultaneous presence of the nanoparticle and six individual cognate hybrids in the same cell to activate six functionalities. While being efficient, previously described nanodevices typically demand intensive computer-assisted design and the use of specifically programmed toeholds.

Accordingly, there remains a need in the art for the development of nanoscaffolds to address several present challenges associated with NP-based delivery of functionalities, e.g., siRNA functionalities. Such challenges include, for example, cell-targeting, ease of synthesis, and triggered activation of therapeutic functionalities, and to provide a safe and efficient nanoparticle for the delivery of effective therapeutic and diagnostic functionalities, such as siRNAs.

SUMMARY

The subject matter described herein sets out to describe a series of interdependent complementary nucleic acid nanoparticles that take advantage of dynamic interaction and shape switching to activate multiple functionalities embedded in the complementary particles. As opposed to previously described nanoparticle work, this new approach does not require any toeholds to initiate the interactions and their design principles are simple. Additionally, only two particles are required to simultaneously activate multiple functionalities embedded therein. The novel interrelated nanoparticles are designed by simply taking the reverse complements of the existing nucleic acid scaffolds and assembling them into the "anti-scaffolds." The complementary scaffolds and anti-scaffolds are embedded with partial functionalities (e.g., promoter sequences, gene encoding sequences, siRNA sequences, Dicer substrate sequences, optical sensors, aptamers) that are made whole (and therefore activated) upon the interaction between the two complementary nanoparticles and the resultant formation of functionally activated duplexes of double stranded DNA molecules (e.g., with activated functionalities that include promoters, coding regions encoding therapeutic proteins or functional cube-forming RNA strands, or aptamers and optical response elements) and double stranded RNA molecules (e.g., with activated functionalities including siRNA/Dicer substrates, aptamers, and optical response elements).

The subject matter described herein is based at least in part, upon the discovery of dynamic interdependent and complementary nucleic acid interacting nanoparticles ("cubes" or "scaffold" and "anti-cubes" or "anti-scaffold" each comprising a plurality of single strands of DNA or RNA or a mixture thereof) which each on their own house multiple latent functionalities, and wherein through an interparticle and interactive process between a pair of complementary scaffold and anti-scaffold nanoparticles, there transpires a simultaneous (a) disassembly of the single nucleic acid strands of the complementary nanoparticles with (b) the formation of double-strand duplexes of DNA or RNA between the corresponding strands of the complementary nanoparticles, wherein each duplex comprises one strand from a scaffold and a complementary strand from the anti-scaffold, wherein formation of the duplexes simultaneously activates multiple latent functionalities which were initially separated or split between the pair of interacting nanoparticles.

The compositions and methods described herein contemplate the simultaneous activation of a wide range of initially latent functionalities which are activated only upon combining and reacting the at least two complementary nanoparticles, with said latent functionalities, including, but not limited to, transcriptional activation (i.e., transcriptional activation of DNA duplexes to form desired protein-encoding mRNA or self-assembling nanoparticle-forming RNA molecules), optical reporters (e.g., FRET), Dicer substrates and/or siRNA (e.g., for targeted gene silencing or knockdown), and aptamers (e.g., malachite green).

In some embodiments, the complementary nanoparticles (i.e., a cube and anti-cube each with at least one or with multiple latent functionalities) are comprised alone of single strands of DNA or RNA or a combination of DNA and RNA strands, i.e., the strands together form the overall shape of the scaffold and anti-scaffold with no further latent functional elements attached or otherwise included. In this embodiment, the latent functionalities are imparted alone by the single strands of DNA and/or RNA (or mixture thereof) that make up the core shape of the complementary nanoparticles. When the complementary nanoparticles interact and become disassembled, they are simultaneously converted to DNA and/or RNA duplexes which themselves have the desired or intended functionalities. Such functionalities can include, for example, transcriptional activation (e.g., wherein a formed DNA duplex is designed with a promoter sequence and a gene coding region, or a DNA duplex is formed with a promoter and a region the codes for an RNA nanoparticle-forming strand) or siRNA (e.g., a formed RNA duplex becomes a substrate for Dicer processing, which then produces an siRNA molecule that may function to carry out targeted gene knock-down), and other functionalities.

In other embodiments, one or more of the single strands of DNA or RNA or a combination of DNA and RNA strands that make up the overall core shape of the scaffold and anti-scaffold are modified to comprise one or more latent appendaged functionalities. The latent appendaged functionalities may comprise half or a portion of an optical response moiety (e.g., FRET component, such as Alexa488 or Alexa546, or a BROC or a COLI moiety of a BROC-COLI aptamer), or half or a portion of a transcriptional promoter, or half or a portion of a Dicer substrate, or half or a portion of an aptamer (e.g., malachite green), or the like. The latent appendaged functionality may be joined directly to the core single DNA or RNA strands of the cube or anti-cube particles (e.g., COLI or BROC portions of the BROC-COLI aptamers, see e.g., FIG. 3). The latent appendaged functionalities may also take the form of an extended hybrid arms that comprise one or more latent functionalities. For example, a DNA cube have at least one hybrid arm may comprise a first strand that operates as a latent promoter sequence, whose other half is part of a complementary hybrid arm in the DNA anti-cube particle, that upon reconstitution as a whole promoter in a resulting DNA duplex can drive transcription of a downstream DNA sequence in the same DNA duplex. The hybrid arms may also be hybridized to one or more shorter complementary sequences each representing half of a functionality, such as half of an aptamer sequence (e.g., malachite green) or half of an siRNA molecule or Dicer substrate, which are each in turn functionalized upon forming RNA duplexes with the RC strands from the corresponding and complementary nanoparticle.

The latent functionalities that are activatable through the interaction of complementary cube/anti-cube nanoparticles include, but are not limited to: (i) transcriptional activation (e.g., through the formation of a DNA duplex comprising a promoter sequence and a transcribable sequence) resulting in formation of a mRNA, single strand RNA molecule as an assembly unit for forming an self-assembling RNA cube, or some other functional RNA molecule, (ii) formation of an RNA duplex Dicer substrate for siRNA-based gene silencing, (iii) formation of an optical response marker (e.g., FRET) formed by joining initially separated or latent optical response moieties (e.g., Alexa 488 and Alexa 546) divided between complementary strands of the cubes and anti-cues, and (iv) reassembly of double-stranded nucleic acid-based aptamers (e.g., Malachite Green isothiocyanate) initially split between cubes and anti-cubes.

In another aspect, the nanoparticles can be activated by physical interaction of two complementary otherwise initially inactive nanoparticles with controllable thermodynamic, immunogenic, and chemical properties. In certain embodiments, by optimizing the ratio between RNA and DNA strands entering the composition of assemblies, one can create nanoparticles with optimal immunomodulatory properties when activation of the immune system is desirable. After interaction of the cognate nanoparticles, e.g., under in vitro conditions or in human cells, constructs undergo isothermal shape-switching resulting in activation of one or more functionalities including RNAi, optical response, transcription and split aptamer re-assembly through the simultaneous (a) disassembly of interacting cognate cubes and anti-cubes comprising single strands of DNA or RNA and (b) the formation of double-stranded duplexes of DNA, RNA, or hybrids of DNA and RNA, wherein each duplex comprises one strand of DNA or RNA from a "cube" and another strand of complementary DNA or RNA from the cognate "anti-cube."

In still further embodiments, the number of duplexes that are formed from a pair of interacting cubes and anti-cubes will be a function of the number of pairs of cognate interacting nucleic acid molecules constituting the cubes and anti-cubes.

In one exemplary embodiment, the cubes are formed from six single-stranded DNA or RNA molecules (A, B, C, D, E, and F), and the anti-cubes are formed from six cognate or complementary single-stranded DNA or RNA molecules (anti-A, anti-B, anti-C, anti-D, anti-E, and anti-F). The "cognate" strands have the reverse complementary sequences of the cube sequences. Upon interaction and subsequent disassembly of the cubes and anti-cubes, one set of six distinct duplexes are formed in conjunction with the disassembly: A/anti-A duplex, B/anti-B duplex, C/anti-C duplex, D/anti-D duplex, E/anti-E duplex, and F/anti-F duplex. These duplexes may be embedded with functionality, e.g., template for transcription of a coding region, substrate for Dicer and siRNA gene silencing, or reassembled FRET pairs (Alex 488 and Alexa 546) as an optical response.

In another exemplary embodiment, the cubes are formed from six single-stranded DNA or RNA molecules (A, B, C, D, E, and F), wherein each strand further comprises an extended single-strand functional arm of DNA or RNA at the 5' or 3' end of the A, B, C, D, E, or F strands ("functional arms"). Each of the functional arms may be single-stranded or may comprise one or more double-stranded portions over the length of the arms. The single-strand functional arm may itself constitute half of a function domain, e.g., one strand of DNA of a RNA polymerase promoter. The double-strand portions may also include various functionalities, e.g., split promoter sequence, split nucleic acid-based apatamer sequence, split Dicer substrate sequence or split siRNA sequence. The cubes in this embodiment would paired up with cognate anti-cubes comprising six single-stranded DNA or RNA molecules (anti-A, anti-B, anti-C, anti-D, anti-E, and anti-F), wherein each of the single-strands further comprise an extended single-strand functional "anti-arm" of DNA or RNA at the 5' or 3' end of the anti-A, anti-B, anti-C, anti-D, anti-E, and anti-F strands. Each of the functional anti-arms are complementary to and would hybridize with the cognate functional arms of the cubes. Thus, the anti-arms may similarly be fully single-stranded or may comprise one or more double-stranded portions over the length of the anti-arms, Upon simultaneous disassembly of the cubes and anti-cubes (and their associated functional arms and anti-arms), and assembly of one or more sets of duplexes, said duplexes provide said one or more functionalities, e.g., an assembled transcriptional unit with promoter, an assembled acid-based apatamer sequence, an assembled Dicer substrate sequence or siRNA sequence, and assembled FRET pairs (Alex 488 and Alexa 546) as an optical response to track the formation of the duplexes.

In certain embodiments (e.g., FIG. 1H), the cubes and anti-cubes may each comprise a three-dimensional cuboid shape, having six (6) "sides" or "faces," twelve (12) "edges" (the double-stranded intersection of two single strands from two separate sides), and eight (8) "corners" (the terminal point of three edges). The single strands of DNA or RNA fold to form the "sides" of the cubes and anti-cubes. The sides of the cubes and anti-cubes meet along double-stranded sections forming the "edges" of the cubes and anti-cubes, and the edges terminate at "corners." The corners may include single-stranded portions of one or more of the single-strands of DNA or RNA making up the sides. See FIG. 1H(4). Without being bound by theory, the corners of the cubes and anti-cubes are thought to provide a nucleation site for the interaction and formation of the resulting duplexes formed between the strands of the cubes and the complementary or cognate strands of the anti-cubes. Further, it is theorized that when the cube comes into contact with the anti-cube, the single strands of the cube pair up and begin to hybridize with the cognate or complementary single strands of the anti-cube, beginning at the corner regions since these elements comprise single strand portions. The interactions and hybridizations between the cube strands and the cognate anti-cube strands (or the "anti-strands") lead to the simultaneous deconstruction or otherwise disassembly of the cubes and anti-cubes and the concomitant formation of the duplexes of DNA or RNA, and the concomitant triggering of split functionalities.

Importantly, no toehold sequences are necessary for the cubes and anti-cubes to interact with one another and simultaneously become disassembled while forming cognate functional duplexes.

In addition, only two complementary nanoparticles are necessary to activate multiple functionalities to a cell.

The cubes and anti-cubes are not limited to actual cubes or cuboids, but may encompass other two and three dimensional shapes, including triangles, pyramids, and tetrahedrons, except the cubes and anti-cubes do not encompass rings. Rings and anti-rings were found not to interact with one another and simultaneously become disassembled while forming cognate functional duplexes.

Importantly, only two nanoparticles are required to simultaneously activate multiple functionalities and no ssRNA or ssDNA toeholds are needed to initiate the interaction. Moreover, in the case of co-transcriptional assemblies, only one specifically designed DNA nanoparticle is needed to efficiently produce an RNA counterpart. Overall, the presented strategy allows for the use of simple, multifunctional, and conditionally activated nanoparticles and provides a promising future for their use in nanobioscience.

Thus, in one aspect, the present disclosure relates to a multi-component multiple functionality delivery system comprising at least two complementary nanoparticles, wherein first nanoparticle comprises DNA and/or RNA oligonucleotides, and the second nanoparticle which is complementary to the first nanoparticle comprises reverse complementary DNA and/or RNA oligonucleotides of the first nanoparticle; wherein the complementary nanoparticles interact under physiological conditions leading to thermodynamically driven conformational changes leading to the simultaneous disassembly of the two complementary nanoparticles with re-association of the cognate oligonucleotides to form multiple duplexes. Preferably, the nanoparticles are not rings and have no single stranded toeholds.

In one embodiment, the disclosure provides a multi-component multiple functionality delivery system comprising at least two complementary nanoparticles, wherein first nanoparticle comprises DNA, and the second nanoparticle which is complementary to the first nanoparticle comprises reverse complementary DNA of the first nanoparticle; wherein the complementary nanoparticles interact under physiological conditions leading to thermodynamically driven conformational changes leading to re-association to form multiple duplexes, and wherein the nanoparticles are not rings and have no single stranded toeholds.

In another embodiment, the disclosure provides a multi-component multiple functionality delivery system comprising at least two complementary nanoparticles, wherein first nanoparticle comprises RNA, and the second nanoparticle which is complementary to the first nanoparticle comprises reverse complementary RNA of the first nanoparticle; wherein the complementary nanoparticles interact under physiological conditions leading to thermodynamically driven conformational changes leading to re-association to form multiple duplexes, and wherein the nanoparticles are not rings and have no single stranded toeholds.

In another embodiment, the disclosure provides a multi-component multiple functionality delivery system comprising at least two nanoparticles, wherein first nanoparticle comprises a hybrid of DNA and RNA, and the second nanoparticle which is complementary to the first nanoparticle comprises reverse complementary hybrid DNA and RNA of the first nanoparticle; wherein the complementary nanoparticles interact under physiological conditions leading to thermodynamically driven conformational changes leading to re-association to form multiple duplexes, and wherein the nanoparticles are not rings and have no single stranded toeholds.

In some embodiments, complementary nanoparticles further comprise multiple functionalities that become activated only upon the interaction of complementary nanoparticles and the concomitant formation of duplexes having one or more functionalities, wherein the functionalities include but are not limited to siRNA or RNAi (or duplex RNA Dicer substrates which form siRNAs once processed), transcription assembly (e.g., duplex DNA with transcription promoter and gene coding region), optical response (e.g., reassembled FRET pairs (Alex 488 and Alexa 546, each coupled to one of the strands of the reassembled duplex)) and split aptamer (e.g., a double-stranded nucleic acid based aptamer such as Malachite Green).

In other embodiments, nanoparticles of polyfunctional switch can be cubes, tubes, triangle or any other shape but not rings.

In some additional embodiments, ratio of DNA and RNA in nanoparticles of the polyfunctional switch controls the immunostimulatory activity, thermodynamic stability, resistance to nuclease degradation, rate of re-association and cost of production of nanoparticles.

In some embodiments, the oligonucleotides control more than one function after re-association.

In certain embodiments, the complementary nanoparticles are six stranded cubes and anti-cubes.

In other embodiments, the complementary nanoparticles of the cube and anti-cube nanoparticles comprise only DNA oligonucleotides, only RNA oligonucleotides or DNA and RNA oligonucleotides in various ratios.

In additional embodiments, DNA and/or RNA oligonucleotides of the complementary nanoparticles have more than one functionality attached thereto (e.g., at the edges) that get activated after re-association.

In other embodiments, functionalities that get activated after re-association are RNAi agents, split DS RNAs, transcription promoters, T7 RNA polymerase promotors, optical response markers, and split aptamers.

In some embodiments, nanoparticles are attached to a lipid-based delivery system, for example, Lipofactamine 2000.

In additional embodiments, nanoparticles after delivery induce immune response upon re-association.

In some embodiments, immune-stimulation depends on the ratio of RNA and DNA in the nanoparticle cubes and anti-cubes described herein. In certain embodiments, the cubes and cognate anti-cubes may comprise six single strands of DNA (6DNA cube and 6DNA anti-cube). In other embodiments, the cube may comprise 5 strands of DNA and 1 strand of RNA (5DNA/1RNA cube) and the cognate anticube may comprise the complementary strands (complementary 5 strands of DNA and 1 strand of RNA) (5DNA/1RNA cube and 5DNA/1RNA anti-cube). In other embodiments, the cube may comprise 4 strands of DNA and 2 strands of RNA (4DNA/2RNA cube) and the cognate anti-cube may comprise the complementary strands (complementary 4 strands of DNA and 1 strand of RNA) (4DNA/2RNA anti-cube). In still other embodiments, the cube may comprise 3 strands of DNA and 3 strands of RNA (3DNA/3RNA cube) and the cognate anti-cube may comprise the complementary strands (complementary 3 strands of DNA and 3 strands of RNA) (3DNA/3RNA anti-cube). Still other embodiments may comprise a cube with 2 strands of DNA and 4 strands of RNA (2DNA/4RNA cube) and the cognate anti-cube may comprise the complementary strands (complementary 2 strands of DNA and 4 strand of RNA) (2DNA/4RNA anti-cube). Still other embodiments may comprise a cube with 1 strand of DNA and 5 strands of RNA (1DNA/5RNA cube) and the cognate anti-cube may comprise the complementary strands (complementary 1 strand of DNA and 5 strands of RNA) (1DNA/5RNA anti-cube). Still other embodiments may comprise a cube with 6 strands of RNA (6RNA cube) and the cognate anti-cube may comprise the complementary strands (complementary 6 strands of RNA) (6RNA anti-cube).

It was surprisingly observed that, as discussed in the Examples and shown in FIG. 1, as the ratio of DNA to RNA is decreased (i.e., increasing the ratio of RNA to DNA), the thermal stability of the cubes/anti-cubes is increased. Thus, there is an inverse relationship between the ratio of DNA to RNA and temperature stability. Accordingly, cubes/anti-cubes having 6DNAs and no RNA are expected to have the lowest thermal stability, whereas cubes/anti-cubes having 6RNAs and no DNA are expected to have the highest thermal stability. And, 5DNA/1RNA, 4DNA/2RNA, 3DNA/3RNA, 2DNA/4RNA, and 1DNA/5RNA cubes/anti-cubes are expected to have increasing thermal stability.

It was also surprisingly observed, as discussed in the Examples and shown in FIG. 1, that as the ratio of DNA to RNA is decreased (i.e., increasing the ratio of RNA to DNA), the immunogenicity of the cubes/anti-cubes is increased. Thus, there is an inverse relationship between the ratio of DNA to RNA and immunogenicity. Accordingly, cubes/anti-cubes having 6DNAs and no RNA are expected to have the lowest degree of immunogenicity, whereas cubes/anti-cubes having 6RNAs and no DNA are expected to have the highest degree of immunogenicity. And, 5DNA/1RNA, 4DNA/2RNA, 3DNA/3RNA, 2DNA/4RNA, and 1DNA/5RNA cubes/anti-cubes are expected to have increasing levels of immunogenicity.

It was also surprisingly observed, as discussed in the Examples and shown in FIG. 1, that as the ratio of DNA to RNA is decreased (i.e., increasing the ratio of RNA to DNA), the stability of the nanoparticles in blood serum is generally increased. Thus, there is generally an inverse relationship between the ratio of DNA to RNA and stability in blood serum. Accordingly, cubes/anti-cubes having 6DNAs and no RNA are expected to have the lowest degree of blood serum stability, whereas cubes/anti-cubes having 6RNAs and no DNA are expected to have a higher degree of serum stability. And, 5DNA/1RNA, 4DNA/2RNA, 3DNA/3RNA, 2DNA/4RNA, and 1DNA/5RNA cubes/anti-cubes are expected to have generally increasing levels of blood serum stability. It was further surprisingly observed that cubes or anti-cubes having the same amount of DNA and RNA were found to have almost the same or more stability as 1DNA/5RNA or 6RNA particles.

In another aspect, the invention provides a method for treating a disease or disorder in a subject by administering a therapeutically effective amount of a composition comprising at least two reverse complementary nanoparticles to the subject, wherein one or more therapeutic functionalities are activated by the interaction of the complementary nanoparticles.

In another aspect, the invention provides a method for treating a subject having a disease or disorder treatable with one or more RNAi agents, involving administering a composition comprising at least two reverse complementary nanoparticles to the subject.

A further aspect of the invention provides a cell including a composition of the invention.

Another aspect of the invention provides a pharmaceutical composition including a composition of the invention.

An additional aspect of the invention provides a kit including a composition of the invention, and directions for its use.

In certain embodiments, the invention provides at least two RNA and/or DNA reverse complementary nanocubes with multiple functionalities.

In some embodiments, the reverse complementary nanocubes comprise at least one of the sequences described herein (in the description and Figures), including any of the sequence identifiers identified herein.

In one embodiment, the functionalities comprise one or more agents. In another embodiment, the agents are selected from one or more of the group consisting of: inhibitory nucleic acids, fluorescent dyes, small molecules, RNA-DNA hybrids with split functionalities, split lipase, split GFP, proteins, therapeutic agents and imaging agents. In a related embodiment, the inhibitory nucleic acids are selected from the group consisting of: siRNAs, RNA or DNA aptamers and ribozymes.

In one embodiment, the one or more agents are the same. In another embodiment, the one or more agents are different.

In another embodiment, a first RNA is complementary to a second RNA and when duplexed forms an siRNA.

In another embodiment, the siRNA inhibits a target RNA. In a further embodiment, the target RNA is one which produces a therapeutically beneficial result when inhibited. In another further embodiment, the target RNA comprises an RNA that encodes a protein involved in a disease process or a portion thereof. In a further related embodiment of any one of the above aspects, the target RNA encodes an apoptosis inhibitor protein. In another further related embodiment of any one of the above aspects, the target RNA is a pathogenic RNA genome, an RNA transcript derived from the genome of the pathogenic agent, or a portion thereof. In one embodiment, the pathogenic agent is a virus, a bacteria, a fungus, or a parasite. In another embodiment, the target RNA is a viral RNA genome or a portion thereo The invention also features a pharmaceutical composition comprising at least two reverse complementary nanoparticles with multiple functionalities of any one of the aspects of the invention.

In one embodiment, the pharmaceutical composition further comprises a pharmaceutically acceptable excipient, carrier, or diluent.

In another embodiment, the pharmaceutical composition is formulated for the treatment of a disease. In still another embodiment, the pharmaceutical composition is formulated for the treatment of an infection by a pathogenic agent. In another related embodiment, the pathogenic agent is a virus, a bacteria, a fungus, or a parasite.

In another embodiment of any of the above aspects or embodiments, the pharmaceutical composition further comprises a second agent that treats or reduces the symptoms associated with infection by the pathogenic agent.

In one embodiment, the second agent is an anti-viral agent.

In another embodiment, the pharmaceutical composition is formulated for the treatment of a neoplasia.

In another further embodiment, the second agent is an anti-cancer agent.

The invention also features a method of inhibiting or reducing the expression of a target gene in a cell comprising contacting the cell with a therapeutically effective amount of the RNA NP or R/DNA NP of any of the above aspects or embodiments, or the composition of any one of the above aspects or embodiments.

The invention also features a method of killing a pathogen infected cell comprising contacting the cell with a therapeutically effective amount of the RNA nanoparticle (NP) or R/DNA nanoparticle of any one of the above aspects or embodiments or the composition of any one of the above aspects or embodiments.

The invention also features a method of inhibiting replication of a pathogen in a cell comprising contacting the cell with a therapeutically effective amount of the complementary nanoparticles of any one of the above aspects or embodiments or the composition of any one of the above aspects or embodiments.

In one embodiment, the cell is in a subject.

The invention also features a method of reducing pathogenic burden in a subject comprising administering a therapeutically effective amount of the complementary nanoparticles of any one of the above aspects or embodiments or the composition of any one of the above aspects or embodiments In one embodiment, the subject is at risk of developing a pathogenic infection.

In another embodiment, the subject is diagnosed with having a pathogenic infection.

The invention also features a method of treating or preventing a pathogenic infection in a subject comprising administering a therapeutically effective amount of the complementary nanoparticles of any one of the above aspects or embodiments or the composition of any one of the above aspects or embodiments.

In one embodiment, the method reduces the pathogenic burden, thereby treating or preventing the pathogenic infection. In another embodiment, the method induces death in infected cell, thereby treating or preventing the pathogenic infection.

In one embodiment, the subject is a mammal. In another embodiment, the subject is a human.

In one embodiment, the pathogen is a virus, bacteria, fungus, or parasite.

In another embodiment of any one of the above aspects or embodiments, the method further comprises contacting the cell with a therapeutically effective amount of a second therapeutic agent or administering a therapeutically effective amount of the second therapeutic agent to the subject.

In one embodiment, the second therapeutic agent treats the pathogenic infection or the symptoms associated with the pathogenic infection.

The invention also features a method of killing a neoplastic cell comprising contacting the cancer cell with a therapeutically effective amount of the complementary nanoparticles of the above aspects or embodiments or the composition of any one of the above aspects or embodiments, thereby killing the neoplastic cell.

The invention also features a method of treating a subject having a neoplasia, the method comprising administering to a subject a therapeutically effective amount of the complementary nanoparticles of any one of the above aspects or embodiments or the composition of any one of the above aspects or embodiments, thereby treating the subject.

In one embodiment, the neoplastic cell is a cancer cell which is present in a solid tumor.

In another embodiment, the method further comprises contacting the cell with a therapeutically effective amount of a second therapeutic agent or administering a therapeutically effective amount of the second therapeutic agent to the subject.

In one embodiment, the second therapeutic agent is an anti-cancer agent.

The invention also features a kit comprising the RNA nanoparticle or R/DNA nanoparticle of any one of the above aspects or embodiments or the composition of any one of the above aspects or embodiments.

In one aspect, the kit further comprises a second therapeutic agent.

In another aspect, the invention relates to a pharmaceutical composition for triggering RNA interference In a further aspect, the invention relates to a method for treating a subject having a disease or disorder treatable with one or more RNAi agents, comprising administering a composition comprising a DNA or RNA nanostructure described herein.

Other aspects of the invention are described in, or are obvious from, the following disclosure, and are within the ambit of the invention.

The anti-cube is similarly formed, but the single stranded sequences are the complementary sequences, anti-A, anti-B, anti-C, anti-D, anti-E, and anti-F. At 37° C., the cube and anti-cube structures contact one another and become simultaneously disassembled while duplexes are formed between the complementary single strands. In this embodiment, the process would result in the following duplexes: A/anti-A duplex, B/anti-B duplex, C/anti-C duplex, D/anti-D duplex, E/anti-E duplex, and F/anti-F duplex.

Figure 12:
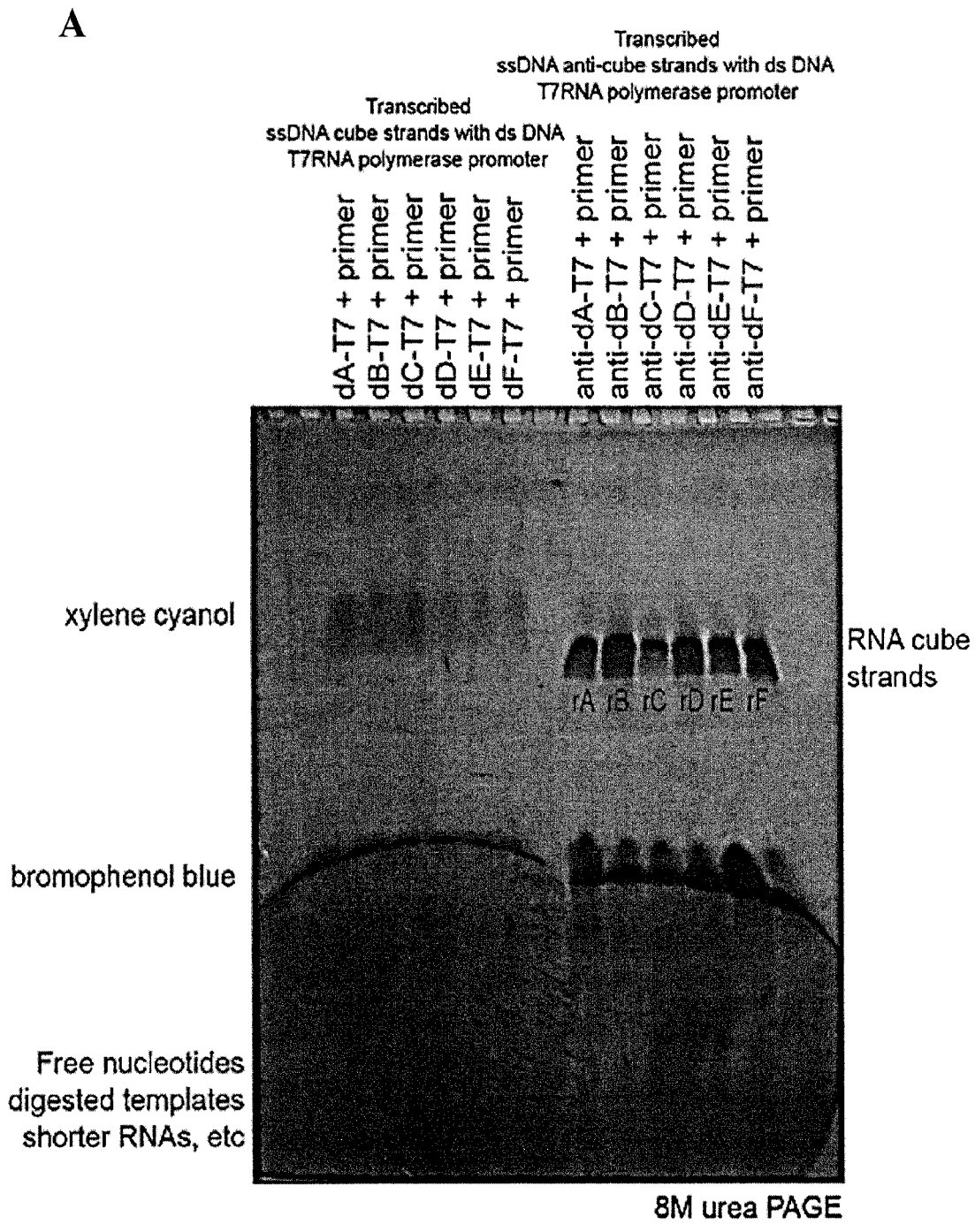
Figure 12B:
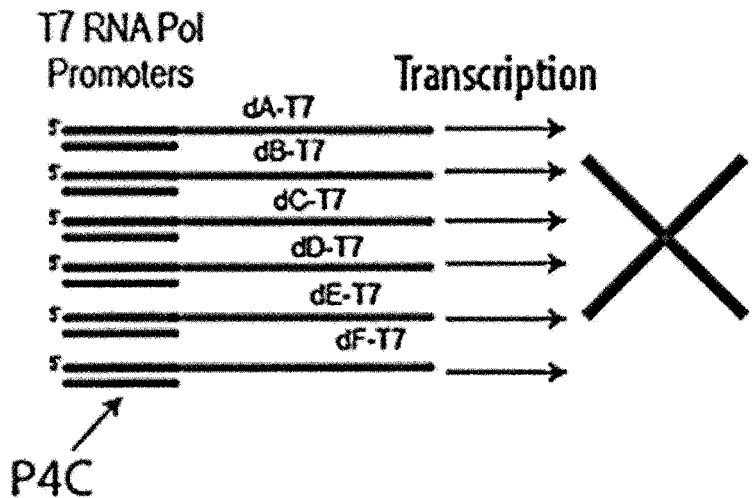
Figure 12B:
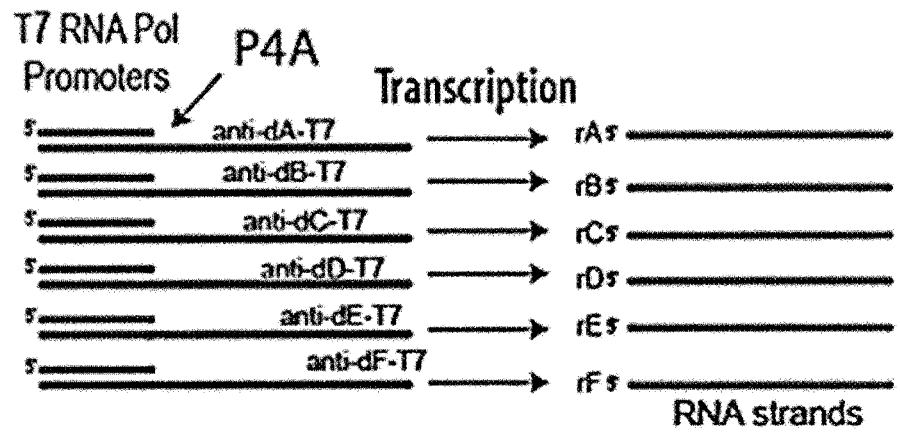

FIG. 12 demonstrates transcription of ssDNA anti-cube strands comprising a 20 bp T7RNA polymerase promoter produces corresponding RNA cube strands rA, rB, rC, rD, rE, and rF. (A) Denaturing 8M urea PAGE that demonstrates the relative yields of transcribed individual template ssDNA cube strands and ssDNA anti-cube strands both comprising dsDNA promoters for T7 RNA Polymerase. Only the ssDNA anti-cubes result in transcriptional production of product RNA strands: rA, rB, rC, rD, rE, and rF. The bands are visualized by UV shadowing. (B) Schematic depicting the transcription of template ssDNA cube strands with 20 bp T7RNA polymerase promoters (top) and template ssDNA anti-cube strands with 20 bp T7RNA polymerase promoters (bottom). The ssDNA cube strands are not transcribed because they lack the proper 3' substrate. The ssDNA anti-cube strands are transcribed to produce corresponding RNA strands: rA, rB, rC, rD, rE, and rF.

Figure 13:
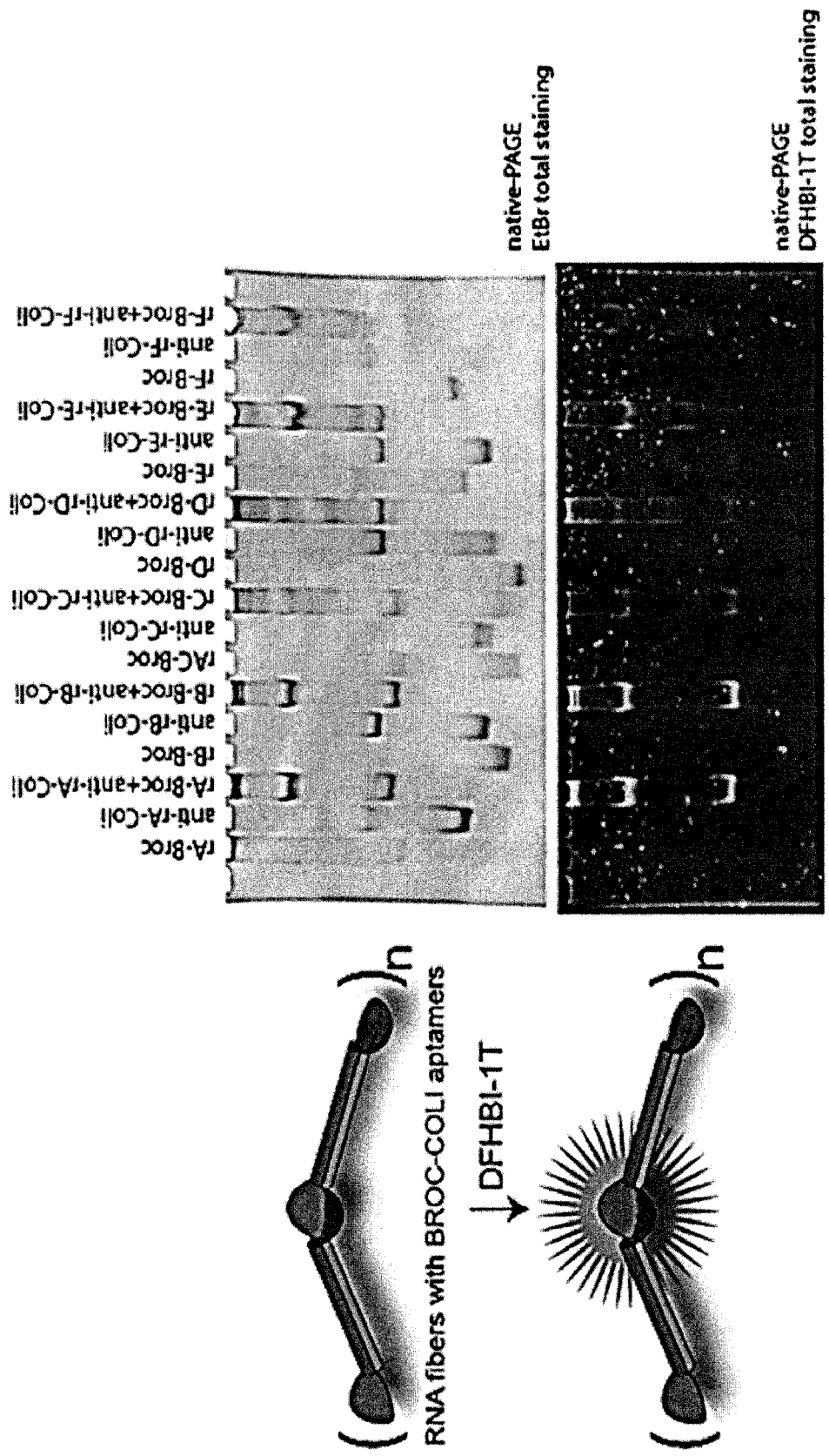

FIG. 13 demonstrates fiber formation and simultaneous activation of multiple BROCCOLI aptamers. Schematics of activation of aptamers (left panel) and total EtBr and DFHBI-1T stained native-PAGE (right panel) demonstrates fiber formation and aptamer activation when stained with DFHBI-1T.

Figure 14:
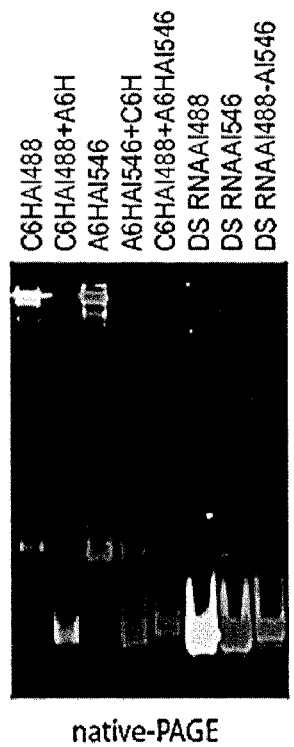
Figure 14:
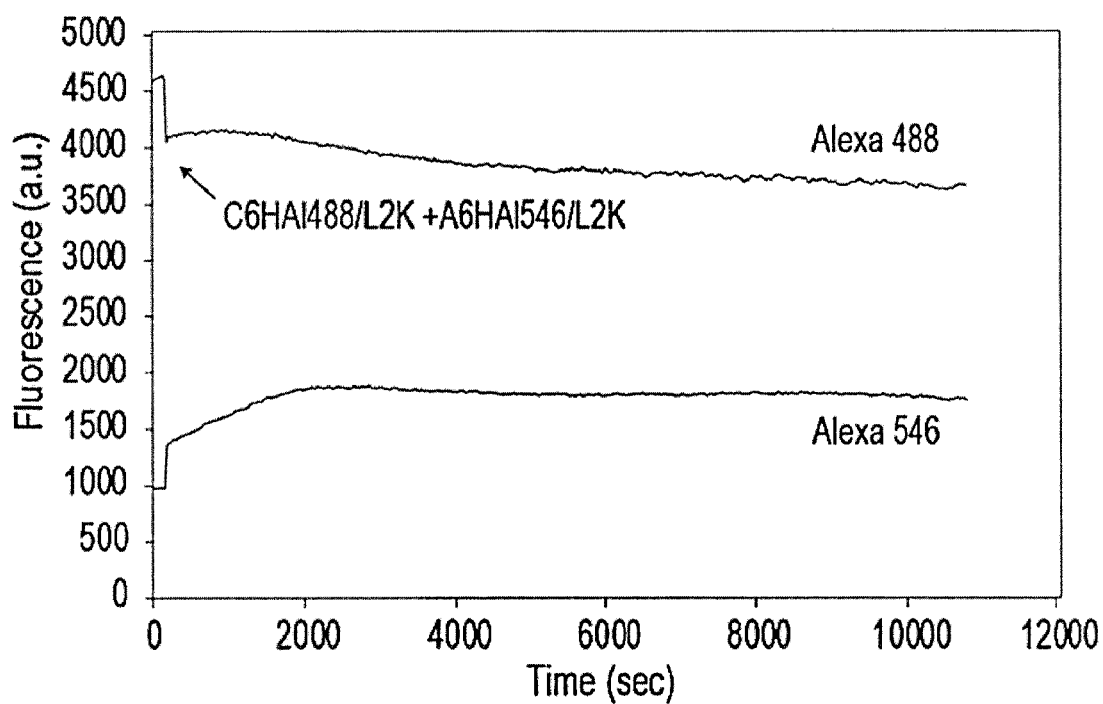
Figure 14:
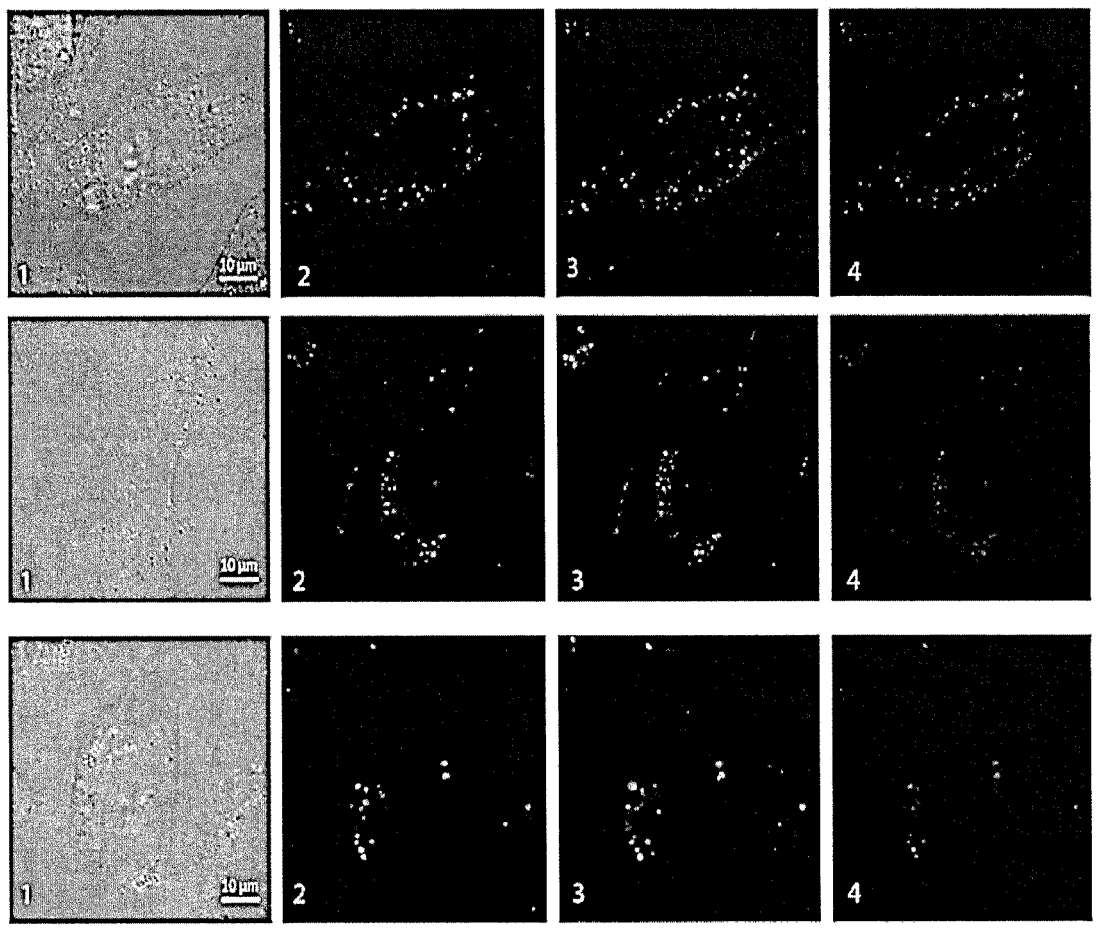

FIG. 14 demonstrates activation of FRET with complementary shape switching nanoparticles. (A) In vitro re-association of fluorescently labeled cubes and anti-cubes with split DS RNAs was visualized by native-PAGE. (B) Fluorescence time traces show no re-association between the fluorescently labeled with Alexa488 and Alexa546 cubes and anti-cubes carrying split Dicer Substrate RNAs (DS RNAs) when associated with Lipofectamine 2000 (L2K). (C) For intracellular FRET experiments, human prostate cancer (PC-3) cells were co-transfected with fluorescently labeled cubes and anti-cubes and images were taken on the next day. Numbers at each image correspond to (1) differential interference contrast images, (2) Alexa 488 emission, (3) Alexa 546 emission, (4) bleed-through corrected FRET image.

Figure 15:
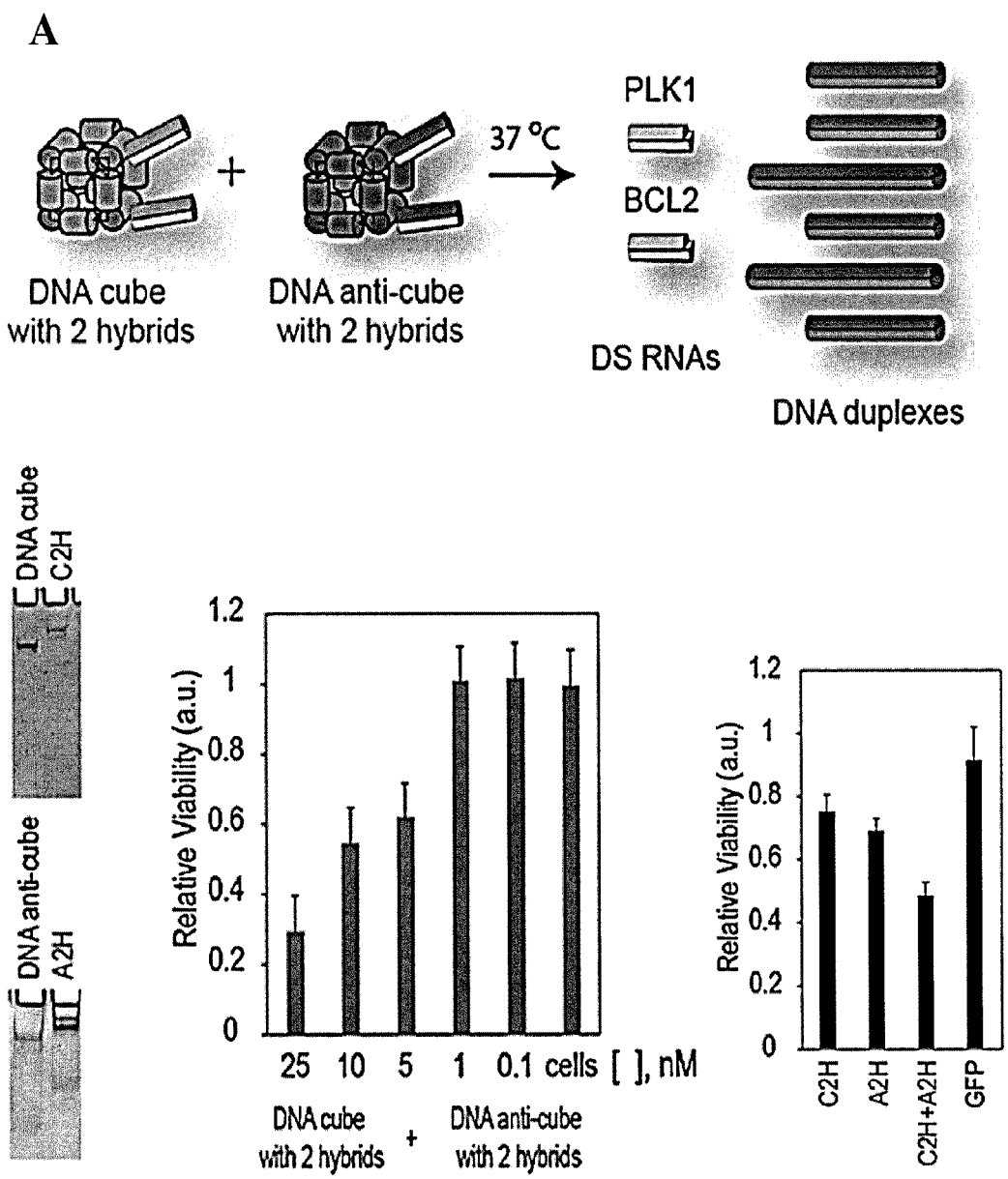
Figure 15:
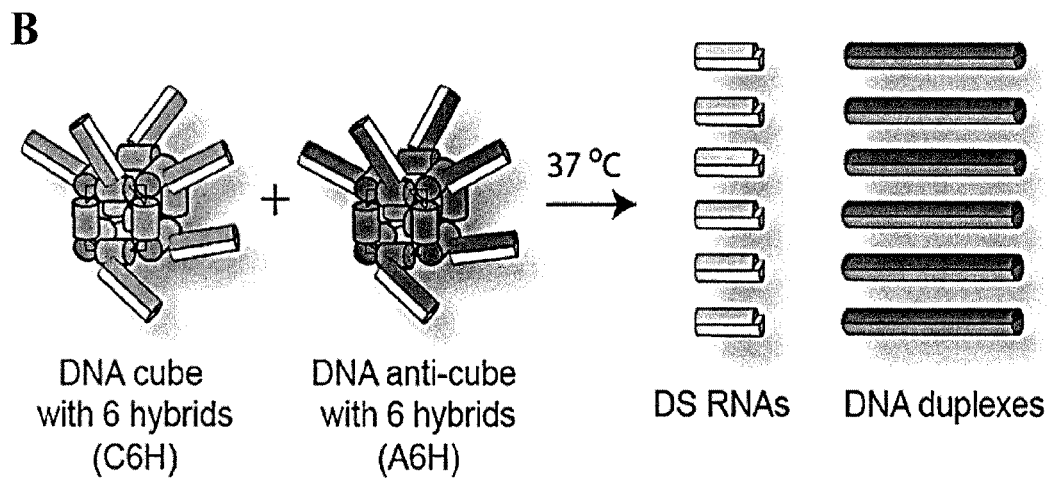
Figure 15:
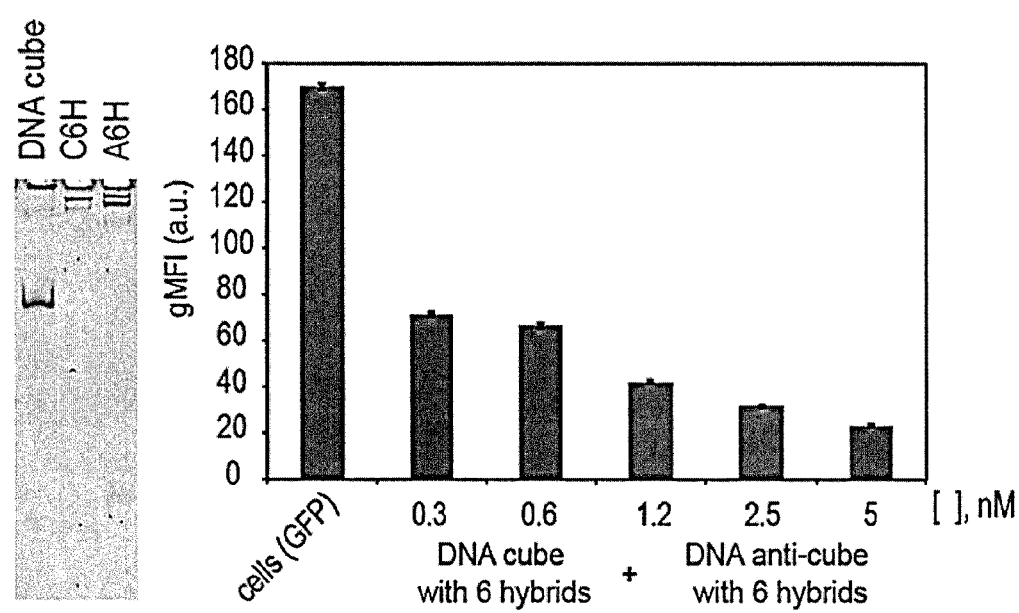

FIG. 15 demonstrates activation of RNA interference with complementary shape switching nanoparticles. (A) The schematic at the top depicts the interaction of DNA cubes with 2 functional DNA/RNA hybrid arms (C2H) and DNA anti-cubes with 6 function DNA/RNA complementary hybrid arms (A2H) which at 37° C. simultaneously disassemble and form two sets of duplexes: 2 double stranded RNA duplexes (formed from the complementary DNA/RNA hybrid arms) and 6 double stranded DNA duplexes. Cell viability assay for HeLa cells transfected with nanoparticles (at 5 nM final) designed to release two DS RNAs: one against PLK1 and the other against BCL2. As negative control, cubes releasing DS RNAs that target GFP were used. (B) The schematic at the top depicts the interaction of DNA cubes with 6 functional DNA/RNA hybrid arms (C6H) and DNA anti-cubes with 6 function DNA/RNA complementary hybrid arms (A6H) which at 37° C. simultaneously disassemble and form two sets of duplexes: 6 double stranded RNA duplexes (formed from the complementary DNA/RNA hybrid arms) and 6 double stranded DNA duplexes. The RNA duplexes may be processed by Dicer to form siRNAs for target gene knockdown. The lower graph and gel image show the results of GFP knockdown assays for human breast cancer cells expressing enhanced GFP (MDA-MB-231/GFP) using the above-described cube/anti-cube system. Then after the transfection of cells, eGFP expression was analyzed with flow cytometry. gMFI corresponds to the geometric mean fluorescence intensity. Error bars denote SEM.

Figure 16:
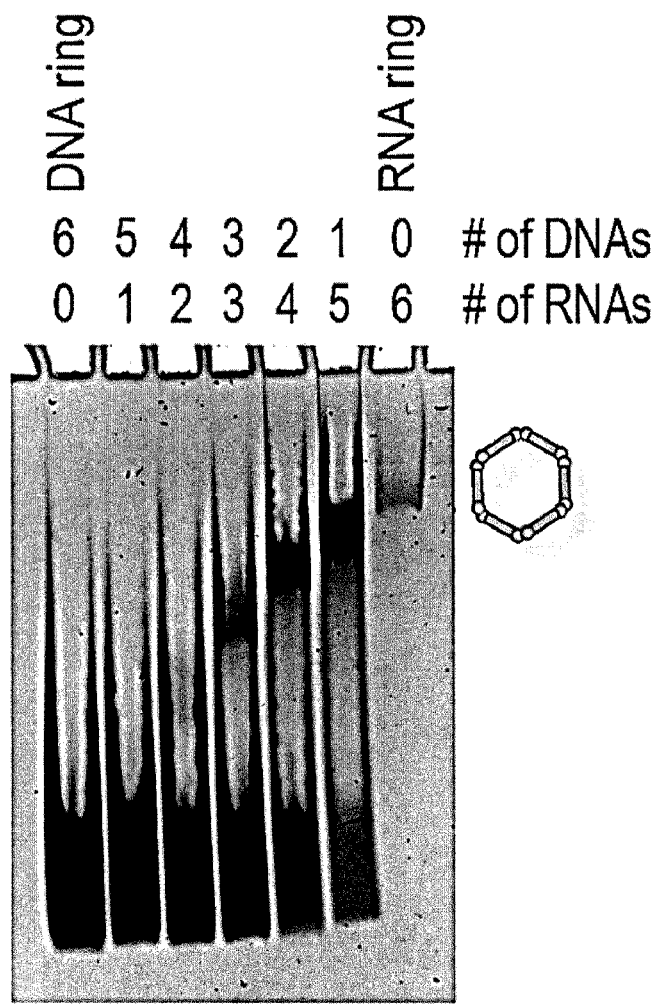

FIG. 16 demonstrates that assembly of RNA and DNA monomers show no assembly for nanorings.

Figure 17:
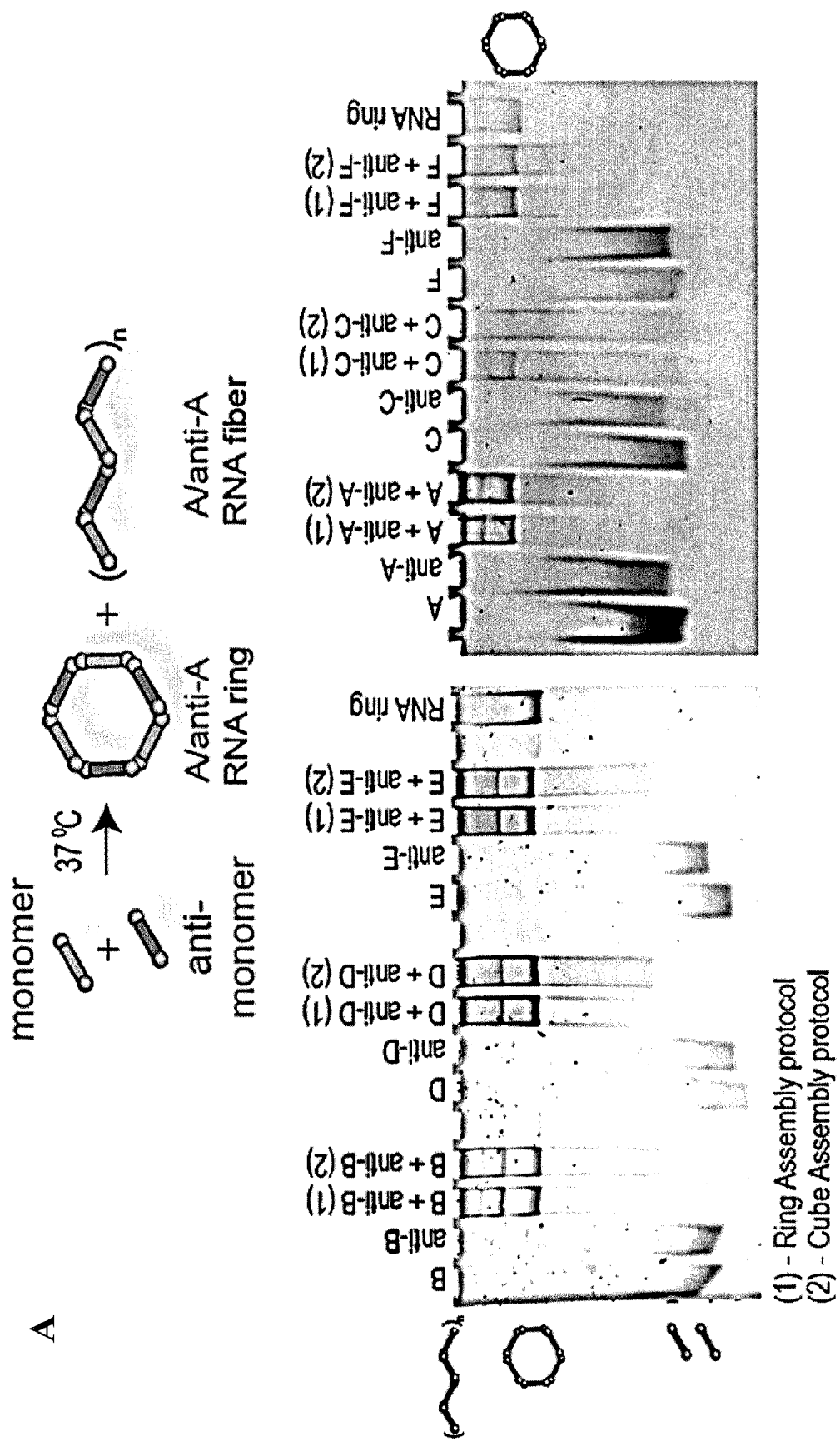
Figure 17:
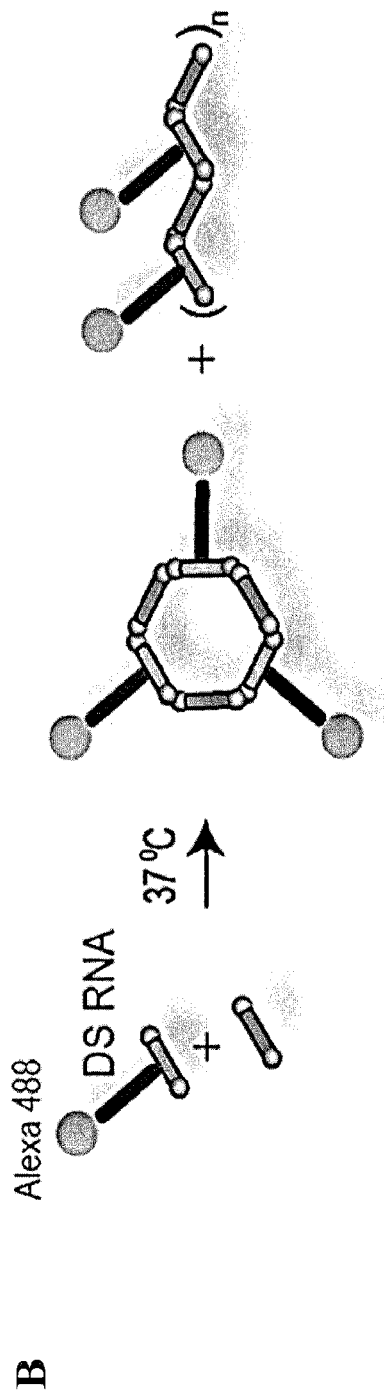
Figure 17:

FIG. 17 demonstrates that contrary to assembled rings, individual monomers and anti-monomers form the mixture of ring ("RNA ring") and fiber structures ("RNA fiber") as shown by native-PAGE. (A) Assemblies of non-functionalized monomers. Two different assembly protocols explained in methods were tested. Depending on the kissing loop sequence the formation either of fibers (e.g., A and anti-A) or rings (e.g., F and anti-F) can be promoted. (B) assembly of functionalized with DS RNAs and Alexa 488 dye monomers lead to the formation of functional fibers and rings.

FIG. 18 provides sequences (SEQ ID NOs: 1-104) used in the present disclosure for preparing the cubes and anti-cubes in various embodiments of the invention.

DETAILED DESCRIPTION

Figure 6:
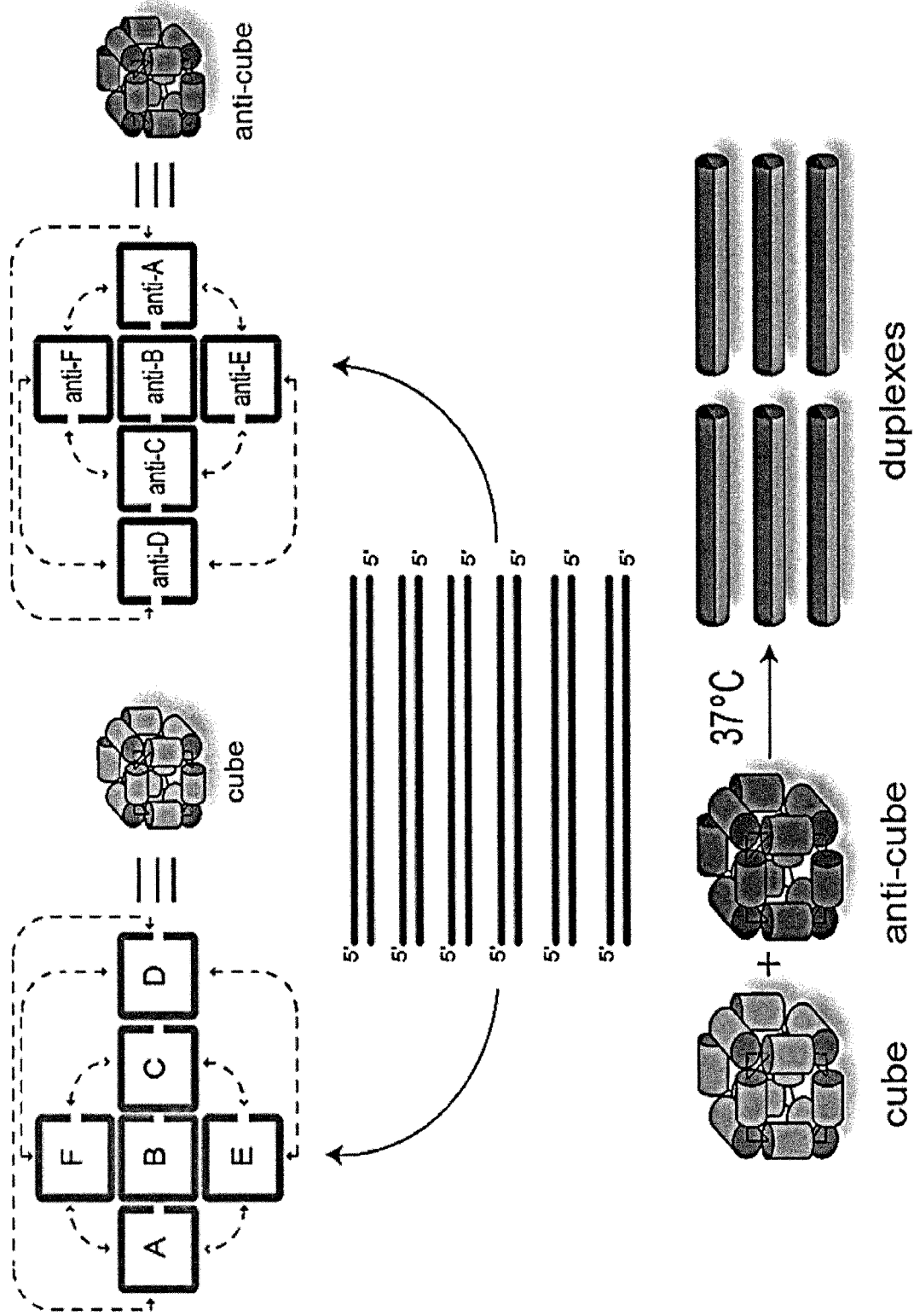
FIG. 6 includes schematics explaining the designing principles of complementary nanoparticles. The schematic depicts that the cube nanoparticle is formed by the single strands A, B, C, D, E, and F (can be RNA or DNA) first folding into individual looped structures, which then assemble into a three-dimensional cube structure through interactions between the edges of the A, B, C, D, E, and F loops. The anti-cube is similarly formed, but the single stranded sequences are the complementary sequences, anti-A, anti-B, anti-C, anti-D, anti-E, and anti-F. At 37° C., the cube and anti-cube structures contact one another and become simultaneously disassembled while duplexes are formed between the complementary single strands. In this embodiment, the process would result in the following duplexes: A/anti-A duplex, B/anti-B duplex, C/anti-C duplex, D/anti-D duplex, E/anti-E duplex, and F/anti-F duplex.

The disclosure provides a series of interdependent complementary nucleic acid nanoparticles that take advantage of dynamic interaction and shape switching to activate multiple functionalities. As opposed to previously described work, this new approach does not require any toeholds to initiate the interactions and their design principles are simple. Additionally, only two particles are required to simultaneously activate multiple functionalities. The novel interrelated nanoparticles are designed by simply taking the reverse complements of the existing RNA scaffolds and assembling them into the "anti-scaffolds" (FIG. 6).

Figure 1:
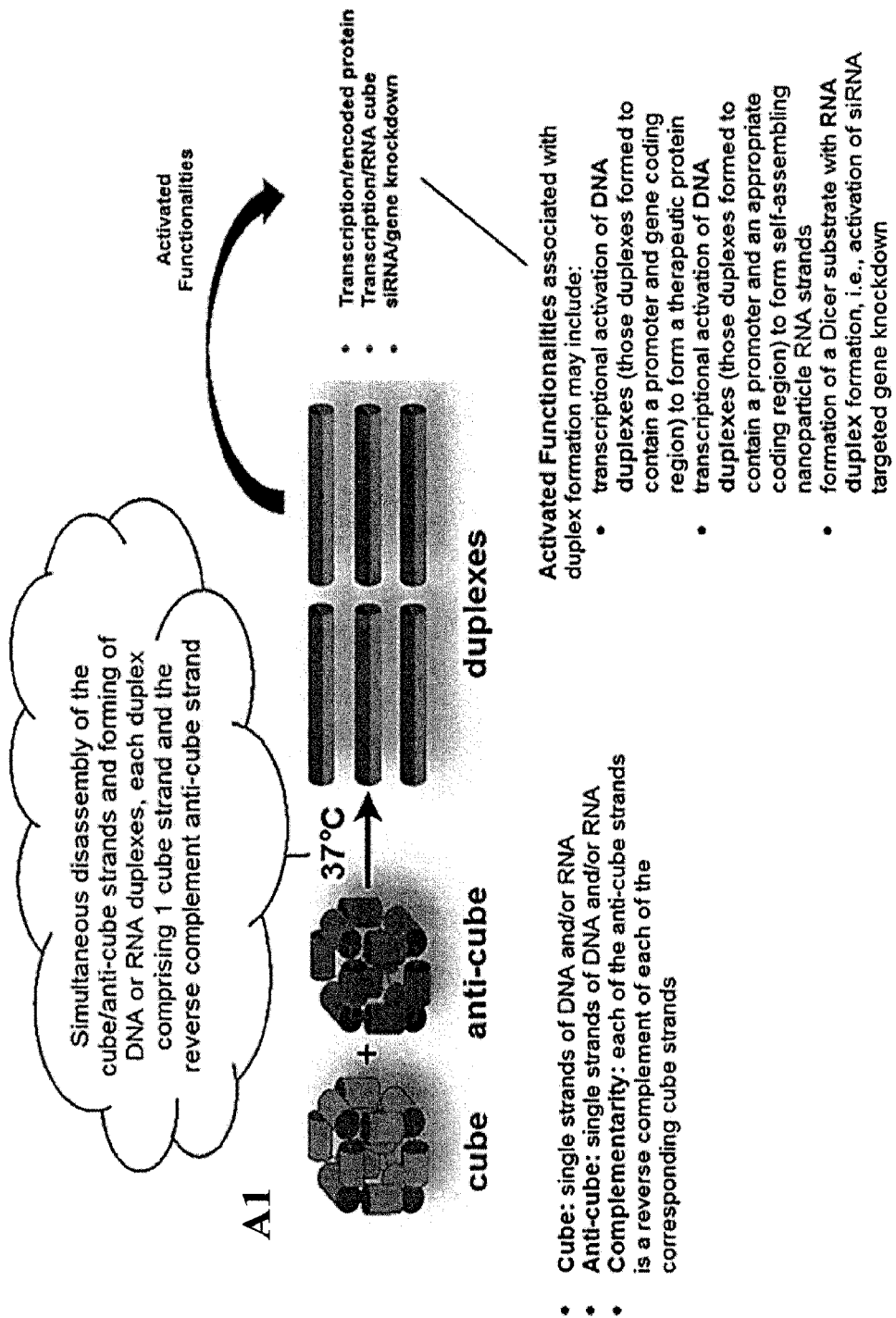
FIG. 1 shows fine-tunable isothermal re-association of complementary shape switching nanoparticles. (A1) Schematic representation of re-association between the complementary cube and anti-cube nanoparticles. In the embodiment depicted, each cube comprises a plurality of single strands of DNA or RNA or a mixture of DNA and RNA strands which form the core particle. Each anti-cube comprises an equal plurality of single strands of DNA or RNA or a mixture of DNA and RNA, and wherein the anti-cube strands are reverse complements of a corresponding strand of the cube. The cube and anti-cube comprise one or more more latent functionalities split between the strands ("the strands") and the RC strands (or "the anti-strands"). The functionalities are formed only when the strands and the anti-strands produce a corresponding duplex upon particle interaction. At 37° C., the cube and anti-cube undergo an interparticle interaction whereby the strands of the cube and the anti-cube disassemble while simultaneously forming DNA and/or RNA duplexes as between hybridized pairs of the strands of the cube and the reverse complement strands of the anti-cube. The formed duplexes have one or more functionalities. For example, a formed DNA duplex may comprise a formed promoter and a gene coding region and give rise to a mRNA and then an encoded therapeutic protein. In another example, a formed DNA duplex may comprises a formed promoter and a sequence encoding a functional RNA product, such as an RNA cube forming RNA strand. The formation of other functionalities is contemplated and this depiction is meant to be non-limiting. (A2) depicts generally the embodiment of A1 but where each of the cube and anti-cube strands further comprise appendaged latent functionalities. In the embodiment, the DNA cube comprises 6 single strands of DNA forming the core scaffold and each encoding a functional RNA sequence for forming an RNA cube. Each of the cube strands further comprises a latent functional appendage in the form of a hybrid DNA molecule, wherein one molecule constitutes half of a T7 RNA Polymerase promoter sequence, and a second shorter DNA sequence hybridized to it is complexed with one half of a FRET fluorescence optical reporter. The DNA anti-cube is similarly constructed but where each of the DNA core single strands are the reverse complement of the cube core strands, and further whether each of the latent appendaged hybrid arms comprises reverse complement sequences to the DNA cube hybrid arms. Further, the shorter functional DNA of the DNA anti-cube is complexed with the second half of the FRET optical sensor. Once the cube and anti-cube interact they undergo simultaneous disassembly and reconstitution as two sets of DNA duplexes, each duplex comprising one strand from the DNA cube and the corresponding RC second strand from the DNA anti-cube. Note that in the case of the optical reporter duplexes, only one of the duplexes comprises the reconstituted FRET complex and the other five duplexes are unmodified and thus, non-functional. The second set of DNA duplexes to form each comprise one strand from a DNA cube (comprised of a core DNA cube strand and its extension arm constituting the half promoter sequence) and the cognate RC of the DNA anti-cube (comprised of the corresponding RC DNA anti-cube strand and its extension arm constituting the other half promoter sequence). Once formed, this set of DNA duplexes comprise a T7 promoter and a sequence encoding one of six functional RNA strands that together autoassemble to form an RNA cube. Thus, in this embodiment, the activated functions include (1) an optical sensor and (2) activated transcription of RNA strands that then autoassemble to form an RNA cube. The formation of other functionalities is contemplated and this depiction is meant to be non-limiting. (B) 3D models of nanoparticles. (C) Experimental and predicted (in grey) melting temperatures of nanoparticles controlled by their compositions and native-PAGE with corresponding assemblies. Error bars indicate s.d.; N=3 (D) Relative re-association rates of RNA, RNA/DNA and DNA cubes and DNA anti-cubes at 25° C. with the formation of DNA and RNA/DNA duplexes and native-PAGE with corresponding re-associations visualized after 30 mins of incubations. Error bars indicate s.d.; N=3. (E) Relative stabilities of nanoparticles in the presence of DNase, RNase and human blood serum. Results are normalized to corresponding non-treated samples. Error bars indicate s.d.; N=3. In (C-E), note that the higher number of RNA strands per nanoparticle weakens the extent of total staining. (F) Immunostimulatory properties of RNA, RNA/DNA and DNA shape-switching nanoparticles delivered using lipofectamine 2000. Error bars indicate s.d.; N=2. Statistically significant results (compared to a positive control, PC) are indicated with asterisks (P-value<0.05). For IL-1β and TNFα all results are statistically significant. (G) AMF images of RNA, RNA/DNA, DNA cubes and RNA anti-cube. (H) provides a detailed schematic showing the structural and functional features of various embodiments of the cube/anti-cube nanoparticles described herein. (1) depicts the general interaction between a cube and an anti-cube at 37 C results in a simultaneous disassembly of the cube and the anti-cube and an assembly of six duplexes comprising one strand each from the cube and the anti-cube. Toeholds are not required for the interation. (2) and (3) show the flattened views of the cube having single-stranded nucleic acid molecules A, B, C, D, E, and F and the cognate anti-cube having the complementary single-stranded nucleic acid molecules anti-A, anti-B, anti-C, anti-D, anti-E, and anti-F. The arrows in (2) and (3) depict interacting sides of the final cube and anti-cube which come together to form double-stranded edges. (4) depicts the detailed features of a single cube or anti-cube showing each "side" of the cube as comprising a single strand nucleic acid (e.g., A-F, or anti-A-anti-F), the "edges" as a double-stranded interaction between two sides, and the "corners" which terminate the edges and comprise single-stranded portions. Without being bound by theory, the corners may provide nucleation sites that may help commence and facilitate the interaction between a cube and an anti-cube, resulting in the formation of the associated functional duplexes, without the need for single-stranded toehold sequences. (5) provides a listing of the general features of the cube, anti-cube, and duplex elements. (6) provides a schematic showing that the cubes and anti-cubes may also in certain embodiments comprise additional functional arms (or anti-arms in the case of a anti-cube). The functional arms may comprise one or one or more functionalities or split functionalities, including (a) split-functional nucleic acid aptamer (e.g., malachite green), (b) split siRNA-forming or Dicer substrate-forming functionality, (c) split promoter-forming functionality (e.g., split T7 RNA polymerase promoter), and (d) split optical-detection functionality (e.g., split Alexa-546 and Alexa-488 tags for Förster resonance energy transfer (FRET)).
Figure 1:
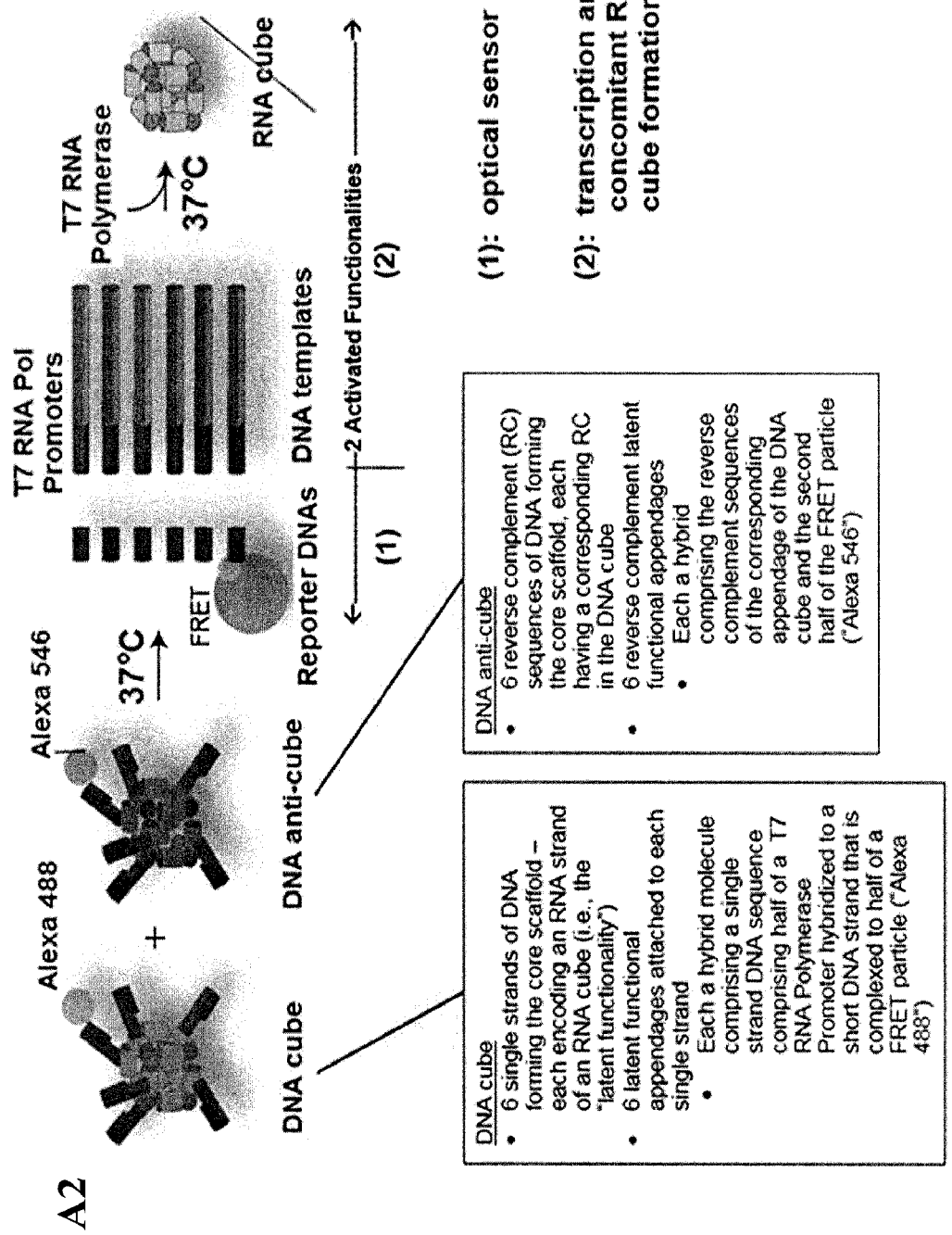
Figure 1:
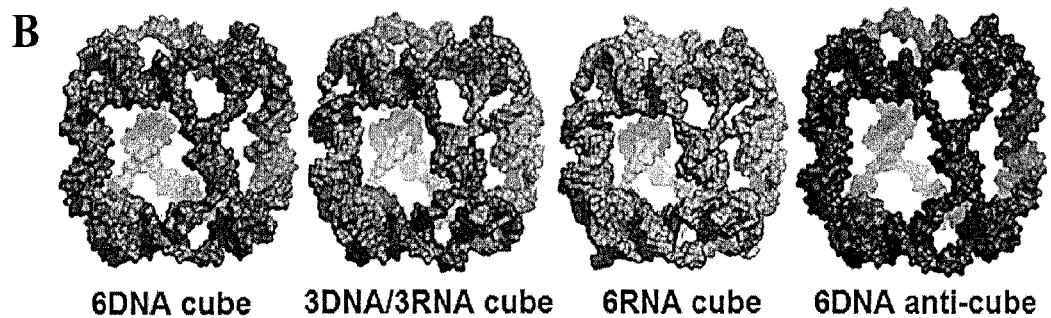
Figure 1:
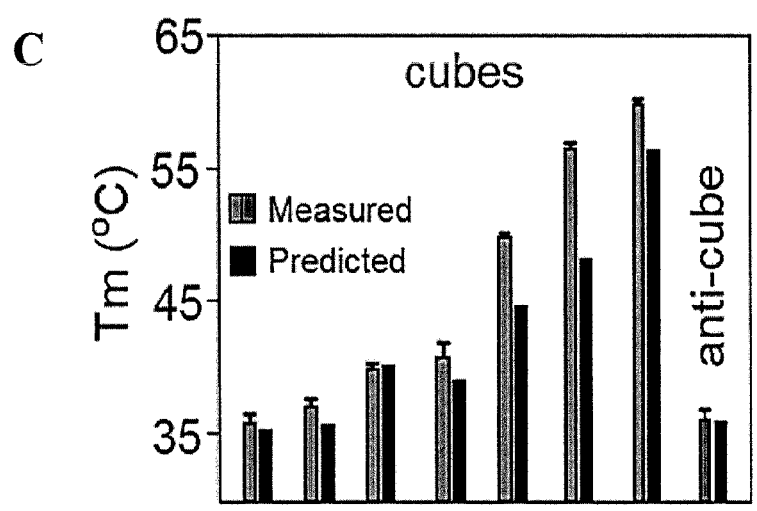
Figure 1:
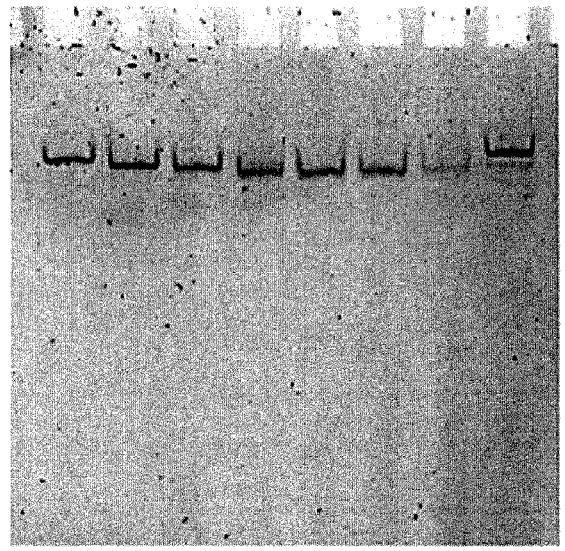
Figure 1:
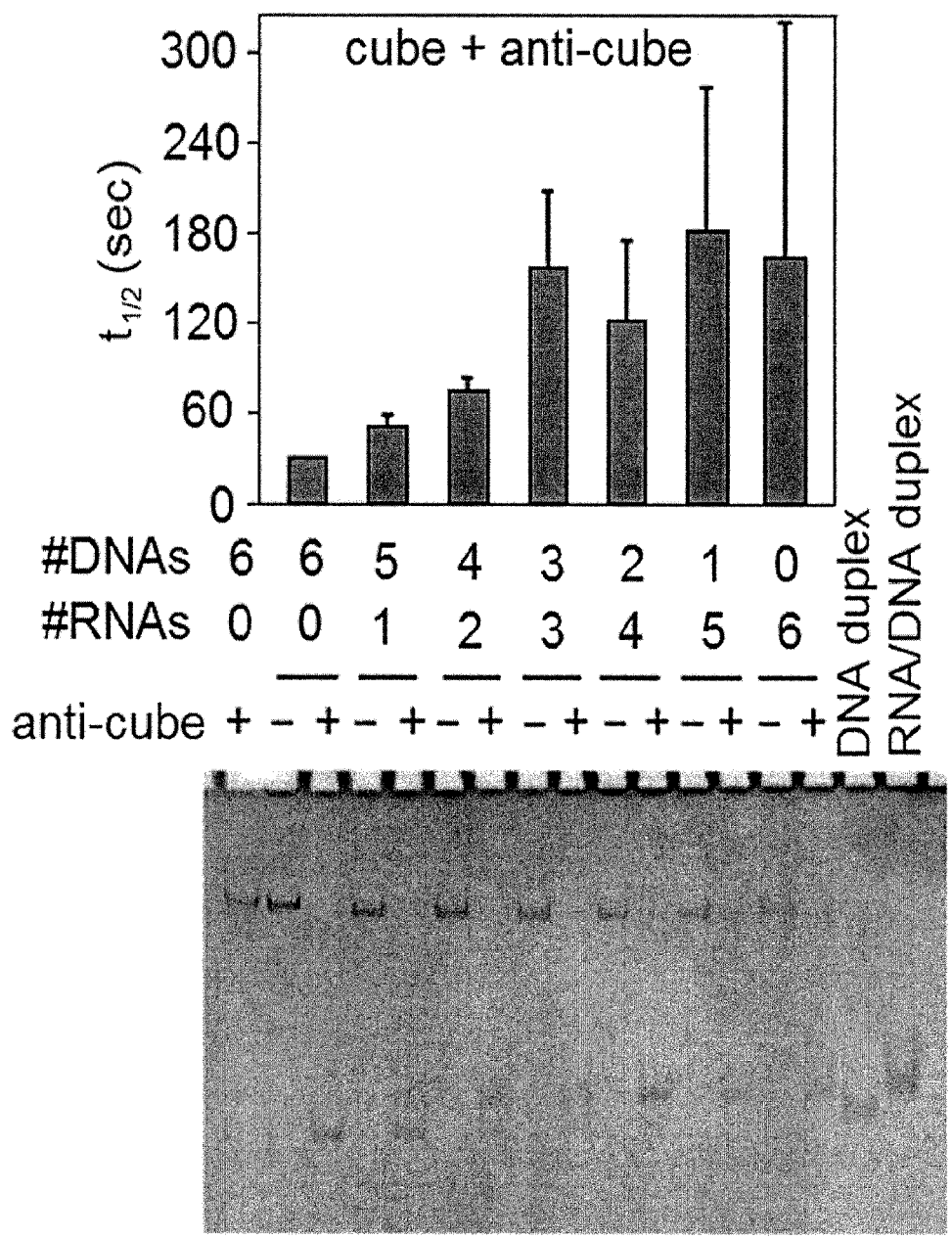
Figure 1:
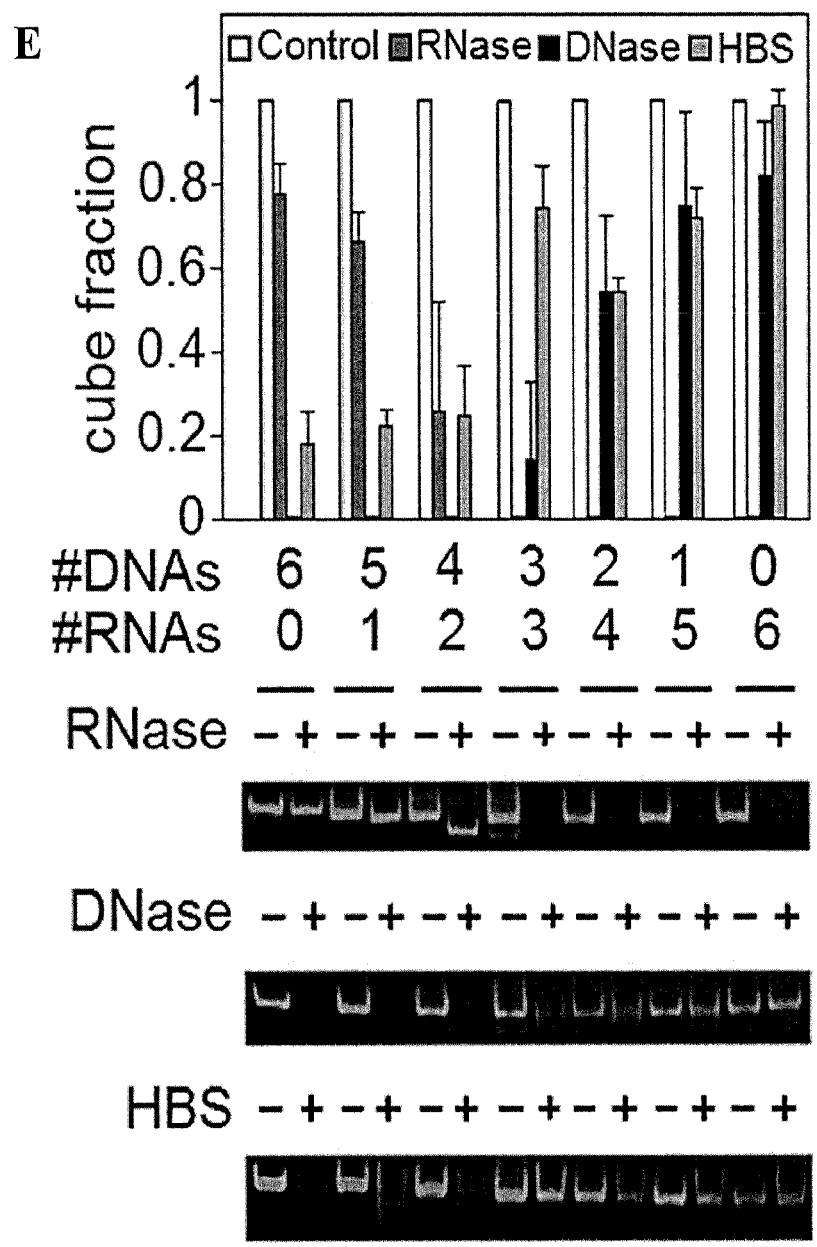
Figure 1:
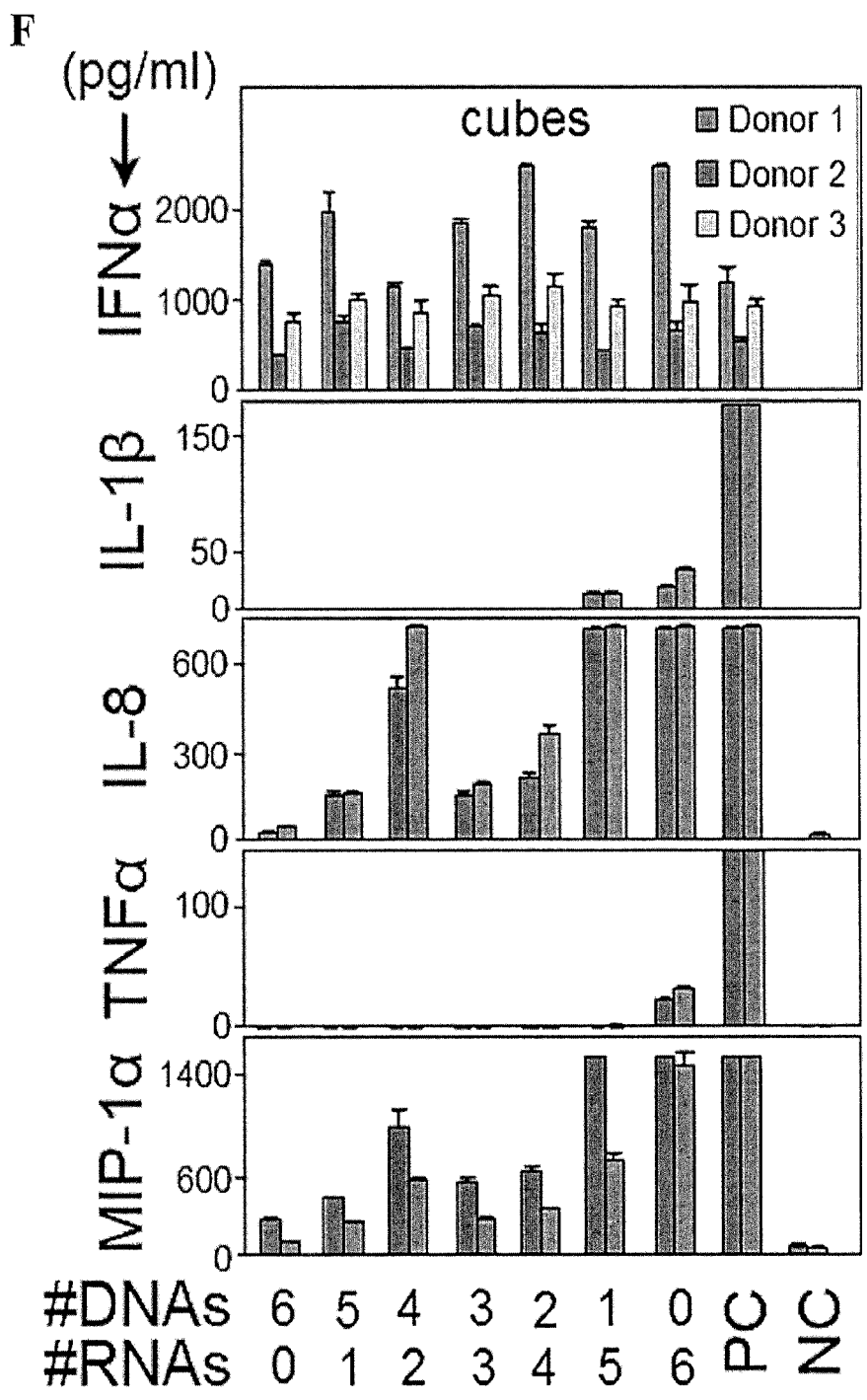
Figure 1:
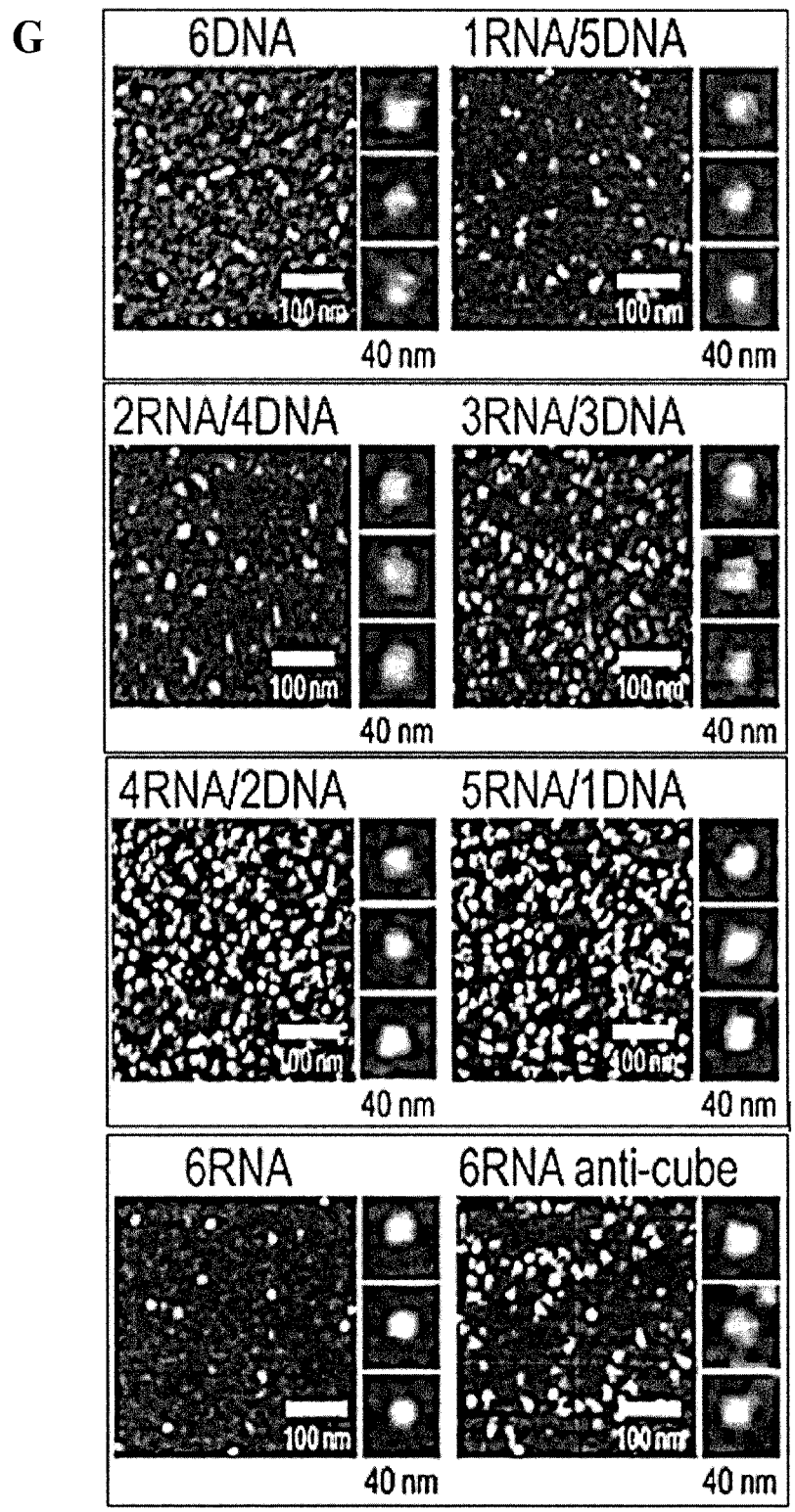
Figure 1:
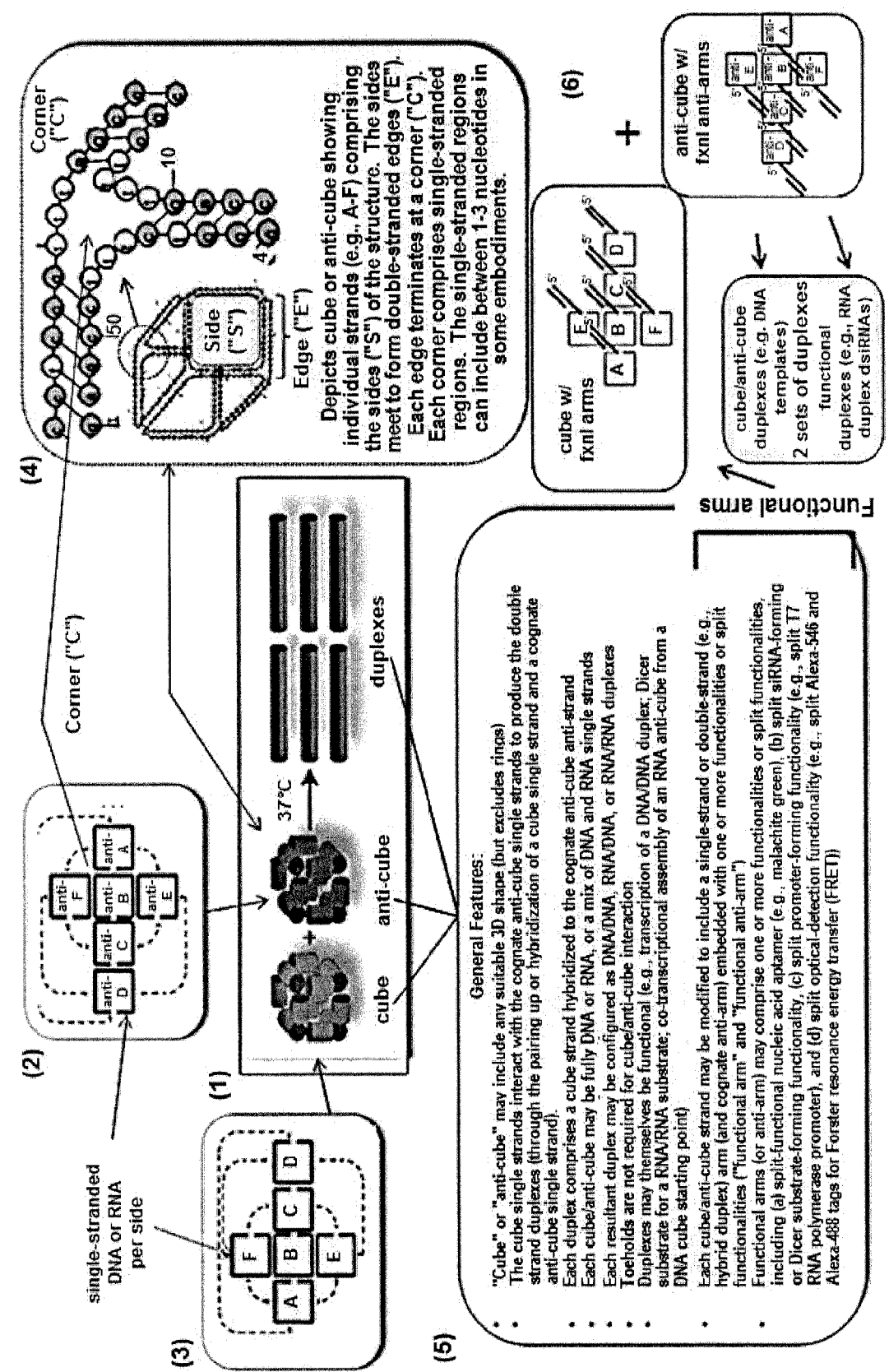

As a proof of concept, nucleic acid cubes and their reverse complements, anti-cubes, are extensively characterized in this work (e.g., FIG. 1). The interaction of cubes with anti-cubes at physiological conditions leads to conformational changes and to the swift formation of multiple duplexes or fibers that can further activate transcription, Förster resonance energy transfer (FRET), formation of functional aptamers, and specific gene silencing. The current research work shows that the immunostimulatory activity, thermodynamic stability, resistance to nuclease degradation, re-association rate, and cost of production for interdependent complementary nanoparticles vary tremendously depending on their composition (e.g., DNA vs RNA). Additionally, RNA hexameric rings and engineered RNA and DNA triangle scaffolds and their corresponding anti-scaffolds are also explored along with nanocubes.

Thus, in one aspect, the disclosure provides RNA and DNA nanoscaffolds in the form of cube structures (e.g., wherein a series of three uracil or three thymine residues form a preferred turn at the corner of a cube structure), which have been designed to address several challenges associated with NP-based siRNA delivery including serum stability, reduced immunogenicity, ease of synthesis, delivery of defined stoichiometries of RNAi agents, and triggered activation of therapeutic functionalities. The instant invention provides interdependent complementary nanoparticles with only two RNA and/or DNA cubes and anti-cubes comprising one or more functionalities. These functionalized polyvalent RNA and/or DNA nanocubes are suitable for therapeutic or diagnostic use in a number of diseases or disorders.

The RNA and DNA nanoparticles described herein have the ability to assemble, e.g., self-assemble, into higher order structures, e.g., a nanocube structure. Methods and compositions of RNA nanoparticles that have the ability to assemble are described in US Publication US2012 0263648. Specific preparation and assembly of nanocube structures as described herein were recently disclosed in Afonin et al. ("Computational and Experimental Characterization of RNA Cubic Nanoscaffolds" *Methods* (2014)).

Most importantly, the cubes and anti-cubes "collectively called nanocubes" of the present invention do not require any toeholds and several nanoparticles for hybridization and functionalization. Instead, only two particles designed by simply taking the reverse complements of each other are required which take advantage of dynamic interaction and shape switching to activate multiple functionalities simultaneously under physiological conditions.

Advantageously, the nanocubes of the instant invention provide a number of improvements over other nanoparticles currently available. For example, the RNA nanocubes of the invention may induce reduced immune responses, as compared to protein nanoparticles currently used, and even in contrast to certain previously described RNA nanoparticles possessing non-cube structures. Indeed, without wishing to be bound by theory, it is initially hypothesized herein that RNA or DNA nanoparticle structure plays a significant role in determining whether an RNA or DNA nanoparticle is immunostimulatory/initiates and interferon and/or PKR response upon administration. Thus, the nanocube structures described herein have been observed to be particularly non-immunostimulatory. This is especially true for DNA nanocubes of the invention, which have been found to exhibit significantly reduced levels of immunostimulation, even as compared to RNA nanocubes, and especially as compared to protein nanoparticles and/or RNA nanoparticles previously described.

Moreover, the nanocubes of the invention are small enough to allow for increased efficiency of administration, while also maintaining a fixed stoichiometry of RNAi payloads across the six arms that result in either dsRNA arms active for RNAi in RNA nanocube formats as described herein, or free dsRNAs active for RNAi that are released from DNA nanocube formats described herein. The nanocubes described herein comprise multiple RNA or DNA subunits each of which has the ability to bind an agent. Moreover, multiple different agents can be present within a single nanoparticle. Previous studies have shown that RNA nanostructures are effective drug delivery vehicles (see, for example, Khaled et al. (2005) Nano Letters 5:1797-1808).

Definitions

The instant invention provides polyfunctional nanoparticles comprising RNA and/or DNA oligonucleotides in shapes of cubes, triangles or any shape other than rings. In some preferred embodiments, these interdependent shape switches comprise multi-functional RNA and/or DNA cubes and anti-cubes further comprising therapeutic, diagnostic and/or delivery agents. Further, these multifunctional interdependent shape switches described herein can be used as drug delivery compositions to treat various diseases or conditions.

The following definitions will be useful in understanding the instant invention.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the term "administering" is meant to refer to a means of providing the composition to the subject in a manner that results in the composition being inside the subject's body. Such an administration can be by any route including, without limitation, subcutaneous, intradermal, intravenous, intra-arterial, intraperitoneal, and intramuscular.

As used herein, the term "functionalities" refers to an activity of a substance or molecule. In various embodiments, DNA duplexes which are formed as a result of intermolecular interaction between at least two complementary nanoparticles may posess one or more functionality. For instance, a duplex DNA may include a functional transcriptional promoter and protein sequence, a functional promoter and a region encoding a functional RNA, an aptamer, or be attached to a functional agent, such as an optical marker (e.g., FRET molecules). In the context of a formed RNA duplex, functionalities may include a Dicer substrate (for forming an siRNA molecule), an aptamer, or be attached to a functional agent, such as an optical marker (e.g., FRET molecules). Other functionalities are contemplated.

In various embodiments, the complementary nanoparticles of the invention comprise "latent" or "split" functionalities. The term "latent" or "split" functionalities refers to a functionality, e.g., a double-stranded nucleic acid aptamer functionality, siRNA molecule, promoter/coding region, optical sensor (e.g., FRET), which is initially bifurcated or physically separated or split into separate but potentially joinable pieces in complementary cube and anti-cube nanoparticles. When the cube and anti-cube systems contact each other, the cubes and anti-cubes are simultaneously disassembled, whereby the individual and cognate strands of DNA and/or RNA in the cubes and anti-cubes interact to form a series of duplexes, including a double-stranded aptamer duplex. A split functionality is initially inactive when its two components are separated into different cubes and anti-cubes, and which then become activated only upon formation of DNA and/or RNA duplexes from the interaction and disassembly of the cubes and anti-cubes.

As used herein, an "aptamer" is an oligonucleotide that is able to specifically bind an analyte of interest other than by base pair hybridization. Aptamers typically comprise DNA or RNA or a mixture of DNA and RNA. Aptamers may be naturally occurring or made by synthetic or recombinant means. The aptamers are typically single stranded, but may also be double stranded or triple stranded. They may comprise naturally occurring nucleotides, nucleotides that have been modified in some way, such as by chemical modification, and unnatural bases, for example 2-aminopurine. See, for example, U.S. Pat. No. 5,840,867. The aptamers may be chemically modified, for example, by the addition of a label, such as a fluorophore, or a by the addition of a molecule that allows the aptamer to be crosslinked to a molecule to which it is bound. Aptamers are of the same "type" if they have the same sequence or are capable of specific binding to the same molecule. The length of the aptamer will vary, but is typically less than about 100 nucleotides.

As used herein, the term "therapeutic agent" is meant to refer to an agent that is capable of exerting an effect on a target, in vitro or in vivo.

As used herein, the term "chemotherapeutic agent" is meant to include a compound or molecule that can be used to treat or prevent a cancer. A "chemotherapeutic agent" is meant to include acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlornaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B;

cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

As used herein, the term "effective amount" refers to that amount of a therapeutic agent alone that produces the desired effect (such as treatment of a medical condition such as a disease or the like, or alleviation of a symptom such as pain) in a patient. In some aspects, the phrase refers to an amount of therapeutic agent that, when incorporated into a composition of the invention, provides a preventative effect sufficient to prevent or protect an individual from future medical risk associated with a particular disease or disorder. A physician or veterinarian of ordinary skill can readily determine and prescribe the effective amount of the bioactive agent required to treat and/or prevent the progress of the condition.

As used herein, the term "cancer" is used to mean a condition in which a cell in a subject's body undergoes abnormal, uncontrolled proliferation. Thus, "cancer" is a cell-proliferative disorder. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

The terms "cancer," "neoplasm," and "tumor," are used interchangeably and in either the singular or plural form, refer to cells that have undergone a malignant transformation that makes them pathological to the host organism. By "neoplastic cell" is meant a cell that is a component of a neoplasia.

As used herein, a "composition" refers to the combination of an active agent (e.g., a polyvalent RNA nanoparticle). The composition additionally can comprise a pharmaceutically acceptable carrier or excipient and/or one or more therapeutic agents for use in vitro or in vivo.

As used herein, the term "conjugated" is understood as attached, linked, or otherwise present on a nanoparticle.

As used herein, "disease" is meant to refer to any condition or disorder that damages or interferes with the normal function of a cell, tissue, or organ.

As used herein, "effective amount" is meant to refer to the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

As used herein, "inhibits neoplasia" is meant decreases the propensity of a cell to develop into neoplasia or slows, decreases, or stabilizes the growth or proliferation of a neoplasia.

As used herein, "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

As used herein, "kits" are understood to contain at least the non-standard laboratory reagents of the invention and one or more non-standard laboratory reagents for use in the methods of the invention.

As used herein, the term "nanoparticle" is meant to refer to a particle between 10 nm and 200 nm in size. A nanoparticle according to the invention comprises a ribonucleic acid (RNA). The RNA can be obtained from any source, for example bacteriophages phi 29, HIV, Drosophila, the ribosome, or be a synthetic RNA.

As used herein, the term "nanocube" or "cube" is meant to refer to a form of oligonucleotide-based nanoparticle that forms a cube-like structure when the strands comprising the nanocube associate/assemble via annealing. In certain embodiments, a nanocube of the invention is formed by at least six independent oligonucleotide strands that can be either DNA or RNA, and which associate to form the "scaffold" or "core" portion of the nanocube. Optionally, a nanocube of the invention also possesses oligonucleotide "arms" that comprise one strand that is covalently attached to the scaffold region of the cube (and therefore can be considered a component of the nanocube scaffold, even if not forming a part of the cube structure), that scaffold-attached arm being capable of annealing to a complementary single-stranded RNA or DNA oligonucleotide that is not so tethered to the nanocube scaffold structure.

As used herein, the recitation "complementary nanoparticles" refers to at least two nanoparticles (a first and a second interacting nanoparticle, i.e., a scaffold and an anti-scaffold or a cube and an anti-cube), wherein each nanoparticle is formed from a plurality of DNA or RNA single strand sequences and wherein the strands of the first nanoparticle and the strands of the second nanoparticle are the reverse complementary sequences of the other. Upon interparticle interaction between complementary nanoparticles, the strands of the first nanoparticle hybridize to the cognate and reverse complementary strands of the second nanoparticle to form functionalized duplexes of DNA or RNA.

An "anti-cube" refers to a nanocube or nanoparticle that is complementary to a cube and is comprised of the reverse complement sequences of the individual DNA or RNA strands of a cube. For example, if a cube comprises 6 individual single stranded DNA sequences dA, dB, dC, dD, dE, and dF, the anti-cube comprises 6 individual single stranded DNA sequences that are the reverse complements of those sequences and may be referred to as anti-dA, anti-dB, anti-dC, anti-dD, anti-dE, and anti-dF. The "d" designates a single strand of DNA. In another example, it a cube comprises 6 individual single stranded RNA sequences rA, rB, rC, rD, rE, and rF, the anti-cube would comprise 6 reverse complement sequences anti-rA, anti-rB, anti-rC, anti-rD, anti-rE, and anti-rF. The "r" designates a single strand of RNA. The cubes and anti-cubes may also be composed of a mix of single strands of DNA and RNA, e.g., if a cube is rA, rB, rC, dD, dE, and dF, (i.e. 3RNA/3DNA), the anticube would be anti-rA, anti-rB, anti-rC, anti-dD, anti-dE, and anti-dF (i.e., anti-3RNA/anti-3DNA).

While specific sequences were used in the creation of RNA and/or DNA nanocube scaffolds, it is contemplated, as will be recognized by the skilled artisan, that the spacing of nucleotides within oligonucleotide strands that form cube structures, as well as the use of, e.g., three "U" or "T"

residues at "corners" of the nanocube structure, are more important to the construction and functionality of an individual nanocube than the precise sequences of the oligonucleotide strands that make up a nanocube of the invention. Indeed, the skilled artisan will recognize that provided that annealing between cognate strands occurs at defined locations of the nanocube, substitution of one nucleotide for another at a given position can be performed without fear of disrupting the nanocube structure. Thus, a broad range of sequences beyond those specifically exemplified herein are contemplated for inclusion within the structure of a nanocube, as ultimately, three dimensional structure is more important to the functionality of the nanocubes described herein than precise sequence.

The term "obtaining" is understood herein as manufacturing, purchasing, or otherwise coming into possession of.

The term "oligonucleotide" as used herein includes linear oligomers of nucleotides or analogs thereof, including deoxyribonucleosides, ribonucleosides, and the like. Typically, oligonucleotides range in size from a few monomeric units, e.g., 3-4, to several hundreds of monomeric units. Olgionucleotides can have inhibitory activity or stimulatory activity.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.*, 15th Ed. (Mack Publ. Co., Easton (1975)).

The term "subject" is intended to include organisms needing treatment. Examples of subjects include mammals, e.g., humans, dogs, cows, horses, pigs, sheep, goats, cats, mice, rabbits, rats, and transgenic non-human animals. In certain embodiments, the subject is a human.

The term "toehold" refers to nucleation site of a domain comprising a nucleic acid sequence designed to initiate hybridization of the domain with a complementary nucleic acid sequence.

As used herein, the term "therapeutic agent" includes a drug and means a molecule, group of molecules, complex or substance administered to an organism for diagnostic, therapeutic, preventative medical, or veterinary purposes. This term includes externally and internally administered topical, localized and systemic human and animal pharmaceuticals, treatments, remedies, nutraceuticals, cosmeceuticals, biologicals, devices, diagnostics and contraceptives, including preparations useful in clinical screening, prevention, prophylaxis, healing, wellness, detection, imaging, diagnosis, therapy, surgery, monitoring, cosmetics, prosthetics, forensics and the like. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA), ribonucleic acid (RNA), or mixtures or combinations thereof, including, for example, DNA nanoplexes. Pharmaceutically active agents include the herein disclosed categories and specific examples. It is not intended that the category be limited by the specific examples. Those of ordinary skill in the art will recognize also numerous other compounds that fall within the categories and that are useful according to the invention. Examples include a growth factor, e.g., NGF or GNDF, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifingal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

As used herein, the term "treated," "treating" or "treatment" includes the diminishment or alleviation of at least one symptom associated or caused by the state, disorder or disease being treated. A subject that has been treated can exhibit a partial or total alleviation of symptoms (for example, tumor load), or symptoms can remain static following treatment according to the invention. The term "treatment" is intended to encompass prophylaxis, therapy and cure.

As used here, the phrase "5' or 3' sticky ends" is meant to refer to the 3' and/or 5' protruding ends of DNA or RNA that will bond with complementary sequences of bases. In certain embodiments, the RNA motifs have 5' or 3' sticky ends. In certain embodiments, the 5' or 3' sticky ends are located in the middle of a helix. According to the invention, the 5' and 3' sticky ends can be engineered to be used for self-assembly of nanocube structures.

Other definitions appear in context throughout the disclosure.

Complementary Interacting Nanoscaffolds (e.g., Cubes and Anti-Cubes)

In certain aspects, the present invention is based, at least in part, upon the discovery of dynamic interdependent nucleic acid interacting nanoparticles ("nanoscaffolds" and "anti-scaffolds" or equivalently "cubes" and "anti-cubes") which through a process of simultaneous (a) disassembly of interacting cognate cubes and anti-cubes comprising single strands of DNA or RNA and (b) the formation of double-stranded duplexes of DNA or RNA wherein each duplex comprises one strand of DNA or RNA from a "cube" and another strand of complementary DNA or RNA from the cognate "anti-cube." The duplexes may comprise one or more functionalites which may be initially "split" in an inactive form in each of the cognate cubes and anti-cubes and which become activated upon the formation of the duplexes. Such functionalities may include transcriptional activation through the formation of a DNA duplex with an initially split promoter sequence, an RNA duplex that functions as a Dicer substrate for siRNA-based gene silencing, optical response (e.g., FRET) formed through the joining (in a duplex) of initially split optical response moieties (e.g., Alexa 488 and Alexa 546), and reassembly of double-stranded nucleic acid-based aptamers (e.g., Malachite Green isothiocyanate) initially split between cubes and anti-cubes.

In certain embodiments, the multiple functionalities are associated with the formation of those duplexes formed between the complementary RC strands of the cubes and anti-cubes, respectively. For example, a duplex DNA formed between the cube/anti-cube DNA strands could include a promoter and a coding region, such that formation of the duplex would result in a transcription substrate for the production of a mRNA and concomitant protein. In another example, a duplex DNA formed between the cube/anti-cube DNA strands could include a promoter and a region coding for a functional RNA strand, such that formation of the duplex would result in a transcription substrate for the production of a self-assembling RNA cube. In addition, such DNA duplexes could bring together optical response elements (e.g., FRET or BROC-COLI elements) which are initially decoupled as between the complementary cubes and anti-cubes. In other embodiments, addition functionality may be associated with functional arms of single stranded or double-stranded nucleic acids attached to the cubes that may comprise one or more functionalities. The "appendaged" functionalities may include split promoters, aptamers, Dicer substrates for siRNA-based gene silencing, and split optical response elements (e.g., FRET or BROC-COLI), e.g., and may be in addition to the functionalities already derived from the core strands of the complementary nanoparticles.

The nanoparticles can be activated by physical interaction of two complementary otherwise initially inactive nanoparticles with controllable thermodynamic, immunogenic, and chemical properties. By optimizing the ratio between RNA and DNA strands entering the composition of assemblies, one can create nanoparticles with optimal immunomodulatory properties when activation of the immune system is desirable. After interaction of the cognate nanoparticles, e.g., under in vitro conditions or in human cells, constructs undergo isothermal shape-switching resulting in activation of one or more functionalities including RNAi, optical response, transcription and split aptamer re-assembly through the simultaneous (a) disassembly of interacting cognate cubes and anti-cubes comprising single strands of DNA or RNA and (b) the formation of double-stranded duplexes of DNA, RNA, or hybrids of DNA and RNA, wherein each duplex comprises one strand of DNA or RNA from a "cube" and another strand of complementary DNA or RNA from the cognate "anti-cube."

In one exemplary embodiment, the cubes are formed from six single-stranded DNA or RNA molecules (A, B, C, D, E, and F), and the anti-cubes are formed from six cognate or complementary single-stranded DNA or RNA molecules (anti-A, anti-B, anti-C, anti-D, anti-E, and anti-F). Upon interaction and simultaneous disassembly of the cubes and anti-cubes, one set of six distinct duplexes are formed: A/anti-A duplex, B/anti-B duplex, C/anti-C duplex, D/anti-D duplex, E/anti-E duplex, and F/anti-F duplex. These duplexes may be embedded with functionality, e.g., template for transcription of a coding region, substrate for Dicer and siRNA gene silencing, or reassemble FRET pairs (Alex 488 and Alexa 546) as an optical response. The number of core strands can range and is not limited. For example, the number of core strands (and ultimate nanoparticle shapes) could be 2, 3, 4, 5, 7, 8, 9, 10, 11, 12 or more.

In another exemplary embodiment, the cubes are formed from six single-stranded DNA or RNA molecules (A, B, C, D, E, and F), wherein each strand further comprises an extended single-strand functional arm of DNA or RNA at the 5' or 3' end of the A, B, C, D, E, or F strands ("functional arms"). Each of the functional arms may be single-stranded or may comprise one or more double-stranded portions over the length of the arms. Such double-strand portions may include various functionalities, e.g., split promoter sequence, split nucleic acid-based apatamer sequence, split Dicer substrate sequence or split siRNA sequence. The cubes in this embodiment may be paired up with cognate anti-cubes comprising six single-stranded DNA or RNA molecules (anti-A, anti-B, anti-C, anti-D, anti-E, and anti-F), wherein each of the single-strands further comprise an extended single-strand functional "anti-arm" of DNA or RNA at the 5' or 3' end of the anti-A, anti-B, anti-C, anti-D, anti-E, and anti-F strands. Each of the functional anti-arms are complementary to and would hybridize with the cognate functional arms of the cubes, thereby activating the embedded functions that are initially separated as between the complementary nanoparticles. Thus, the anti-arms may similarly be fully single-stranded or may comprise one or more double-stranded portions over the length of the anti-arms, Upon simultaneous disassembly of the cubes and anti-cubes (ane their associated functional arms and anti-arms), and assembly of one or more sets of duplexes, said duplexes provide said one or more functionalities, e.g., an assembled transcriptional unit with promoter, an assembled acid-based apatamer sequence, an assembled Dicer substrate sequence or siRNA sequence, and assembled FRET pairs (Alex 488 and Alexa 546) as an optical response to track the formation of the duplexes.

In certain embodiments, in connection with FIG. 1H, the cube and anti-cubes may each comprise a three-dimensional cuboid shape, having six (6) "sides" or "faces," twelve (12) "edges" (the double-stranded intersection of two single strands from two separate sides), and eight (8) "corners" (the terminal point of three edges). The single strands of DNA or RNA fold to form the "sides" of the cubes and anti-cubes. The sides of the cubes and anti-cubes meet along double-stranded sections forming the "edges" of the cubes and anti-cubes, and the edges terminate at "corners." The corners may include single-stranded portions of one or more of the single-strands of DNA or RNA making up the sides. See FIG. 1H(4). Without being bound by theory, the corners of the cubes and anti-cubes are thought to provide a nucleation site for the interaction and formation of the resulting duplexes formed between the strands of the cubes and the complementary or cognate strands of the anti-cubes. Further, it is theorized that when the cube comes into contact with the anti-cube, the single strands of the cube pair up and begin to hybridize with the cognate or complementary single strands of the anti-cube, beginning at the corner regions since these elements comprise single strand portions. The interactions and hybridizations between the cube strands and the cognate anti-cube strands (or the "anti-strands") lead to the simultaneous deconstruction or otherwise deassembly of the cubes and anti-cubes and the formation of the duplexes of DNA or RNA, and the concomitant triggering of split functionalities. Importantly, no toehold sequences are necessary for the cubes and anti-cubes to interact with one another and simultaneously become disassembled while forming cognate functional duplexes.

The cubes and anti-cubes are not limited to actual cubes or cuboids, but may encompass other two and three dimensional shapes, including triangles, pyramids, and tetrahedrons, except the cubes and anti-cubes do not encompass rings. Rings and anti-rings were found not to interact with one another and simultaneously become disassembled while forming cognate functional duplexes.

As will be appreciated, the complementary nanoscaffolds (i.e., the cubes and anti-cubes) described herein are composed of single and/or double stranded RNA and/or DNA elements. The elements can include the "core" cube and anti-cube single-stranded nucleic acid molecules, as well as the functional double-stranded or single-stranded nucleic acid arms. RNA and DNA have a number of advantages for nanostructure design. Nanocube structures provide a size range that is large enough to avoid the problem of expulsion from the cell, but are small enough to avoid the problems of cell delivery often encountered with larger particles. RNA is the only biopolymer that can carry genetic information and has catalytic properties. RNA can naturally fold into complex motifs, and RNA motifs are capable of self-assembly. RNA has a natural functionality, for instance RNA can function as ribozymes or riboswitches. Further, RNA is advantageous in eliciting a very low immune response. Moreover, the construction of RNA into ordered, patterned superstuctures has a number of desirable characteristics, including the ability to self-assemble in precisely defined ways, the ability to undergo editing and replication, the ability to undergo controlled disassembly. RNA has versatility in function and structure. Functionally, RNA is the only biopolymer that can carry genetic information and that possesses catalytic properties. Structurally, RNA has predictable intra and intermolecular interactions with well-known structural geometry. The RNA strands that consist of adenine (A), guanine (G), cytosine (C), and uridine (U) can naturally, or can be programmed, to self-assemble via complementary base pairing. The helical region of RNA has a well-known nanometer scale structural geometry of 2.86 nm per helical turn with 11 base pairs and a 2.3 nm diameter. The self-assembly of RNA into complex structures can be facilitated via complementary base pairing or inter- and intra-molecular interactions of the different single stranded regions in the RNA, including internal bulges and loop motifs, and single-stranded overhangs or "sticky-ends". In addition to Watson-Crick base pairing, A, G, C and T can also pair with other, unconventional bases (i.e. non-canonical base-pairing). For purpose of building nanocube structures, DNA has been identified to possess many of the above-described attributes of RNA.

The methods of the invention can be used to assemble RNA and/or DNA nanocubes composed of six or more strands. E.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 112, 113, 114, 115, 116, 117, 118, 119, 120, 121, 122, 123, 124, 125 or more distinct RNA and/or DNA strands.

RNA and DNA Synthesis

RNA molecules and DNA molecules used to make the complementary nanocubes (e.g., the cubes and anti-cubes) of the invention can be produced recombinantly or synthetically by methods that are routine for one of skill in the art. For example, synthetic RNA molecules can be made as described in US Patent Application Publication No.: 20020161219, or U.S. Pat. Nos. 6,469,158, 5,466,586, 5,281,781, or 6,787,305.

Design

One general approach that may be used to create the RNA, or DNA and/or RNA-DNA hybrid elements of the cubes and anti-cubes described herein, is to take known RNA and/or DNA structures, cut them into the building blocks, and reengineer single-stranded loops and regions to facilitate the desired self-assembly. The self-assembly of all the above discussed RNA and/or DNA building blocks into the nanostructures described herein (the cubes and anti-cubes) may be mediated by the complementarity of oligonucleotide regions such as hairpin loops and loop receptors that form non-covalent RNA-RNA, RNA-DNA and/or DNA-DNA interactions, as well as by certain sections that simply are capable of annealing (e.g., the hybridized sequences that form a given side of a core structure and the single-stranded region that forms the "corner" of a cube structure—such corners generally comprise a series of three uracil or three thymine residues in the nanocubes set forth herein. For precise assembly of the RNA and/or DNA building blocks, each of the corresponding complementary interactions (e.g., loop-loop interactions) can be uniquely reengineered.

Two main experimental approaches are used for programmable self-assembly of nucleic acids nanostructures (Jaeger, L.; Chworos, A. Curr Opin Struct Biol 2006, 16, (4), 531-43). The first is a single-step assembly, which is commonly used for DNA nanostructures (Chelyapov, N.; Brun, Y.; Gopalkrishnan, M.; Reishus, D.; Shaw, B.; Adleman, L. J Am Chem Soc 2004, 126, (43), 13924-5; Mathieu, F.; Liao, S.; Kopatsch, J.; Wang, T.; Mao, C.; Seeman, N. C. Nano Lett 2005, 5, (4), 661-5.). The second is a stepwise assembly, which has been commonly described for RNA nanostructures (Chworos, A.; Severcan, I.; Koyfman, A. Y.; Weinkam, P.; Oroudjev, E.; Hansma, H. G.; Jaeger, L. Science 2004, 306, (5704), 2068-72). In the single-step assembly approach, all molecules are mixed together followed by the slow cool annealing procedure. This is only possible if the target building block structure is the one that has the highest number of Watson-Crick base pairs and is therefore the most stable. However, it is understood that thermodynamic stability of different shapes of nanoparticles is also an important consideration, at times more so than Watson base pairing. This approach is, thus, based on the preferential folding of the building blocks at higher temperatures followed by the self-assembly of these building blocks through weaker interactions into final nanostructures at lower temperatures. However, usually there are many other possible structures that are only slightly less stable. In this case, the stepwise approach can be used where the building blocks are separately formed in the first step are then mixed together in the presence of high magnesium (Mg++) concentration to form a final nanostructure. This approach is more time consuming and the melting temperatures of the building blocks and the final nanostructure should be well separated.

The complementary nanoscaffolds described herein (e.g., the cubes and anti-cubes) may be designed to self-assemble by using a number of available building block elements that directed self-assembly. As such, a number of RNA motifs are available as building blocks, including but not limited to RNA I and/or RNA II motifs, kissing loops, RNA I inverse (RNA Ii) and/or RNA II inverse (RNA IIi) motifs. As used herein, the term "motif" in reference to a nanoparticle is meant to refer to a double-stranded or single-stranded ribonucleic acid or analog thereof. Individual motifs are joined together into larger particles by attachment to each other. Attachment can occur by non-covalent linking. Numerous high-resolution RNA structures determined by NMR or X-ray crystallography can be separated into building blocks for design of new RNA nanoparticles and nanomaterials. U.S. application Ser. No. 13/378,985, incorporated by reference in its entirety herein, describes methods of making RNA nanoparticles.

The complementary nanoscaffolds (e.g., the cubes and anti-cubes) are not limited to cuboid-shaped nanoscaffolds (and anti-scaffolds). Rather, the nanoscaffolds may take other forms and shapes including other three-dimensional shapes, such as pyramids and tubes, and other two-dimensional shapes, such as triangles. However, it has been shown that the interaction and re-assembly of the complementary cubes and anti-cubes discussed and reported herein does not operate with respect to nanoparticle rings, and thus, ring-shaped nanoparticles are not contemplated herein.

Conjugation to Nanocubes

The complementary nanoscaffolds (e.g., cubes and anti-cubes) may be used to deliver one or more functionalities to cells, and preferably one or more split functionalities. RNA and/or DNA nanocubes comprising more than one functionality can be used to deliver agents. For example, polyvalent RNA nanocubes, RNA-DNA hybrid nanocubes or DNA-RNA hybrid nanocubes comprising more than one functionalities can be used to deliver one or more agents that are selected from one or more of the group consisting of: siRNAs, RNA or DNA aptamers, fluorescent dyes, small molecules, RNA-DNA hybrids with split functionalities, split lipase, split GFP, proteins, therapeutic agents and imaging agents.

The compositions of the present invention have therapeutic uses. Any number of diseases or disorders can be treated by the compositions of the present invention and may be limited, in fact, only by the agent or agents that can be loaded in the inside of the nanoparticle or conjugated to the outside.

For example, the complementary interacting nanoparticles described herein can be engineered to carry multiple siRNAs against different disease targets. In one exemplary embodiment, six different siRNAs against different parts of the HIV-1 genome can be used for combinatorial RNAi therapy The invention is not limited to the treatment of any disease or group of diseases, but is rather defined by the siRNAs or other therapeutic functionalities that can be used to treat particular diseases. This concept of targeting a specific pathway upon the presence of a particular RNA in the cytoplasm can be applied to cancer (including cancer stem cells) or RNA viruses in general (e.g. Flaviviruses, Alphaviruses). HAART therapy as it currently exists, can successfully suppress virus replication within the human host. With this approach, however, it is currently not possible to eradicate the HIV virus from an infected patient because approved HIV drugs act as virus suppressors and do not kill human cells that are infected by the virus. The present invention can also lead to a novel anti-viral drug that has the unique feature of selectively killing HIV infected cells using appropriate aptamers, for cell targeting, that are associated with RNA NPs containing specific siRNAs or RNA/DNA siRNA hybrids. The guide strands are designed to be an antisense to human apoptosis inhibitor genes (BCL-2, FLIP, STAT3, XIAP, SURVIVIN, etc). Thus, the activation of RNAi (RNA interference pathway) will result in apoptosis of the HIV-infected cell. In addition, in a more general sense, the siRNA targets may include cancer related genes, for example, but not limited to, the hypoxia pathway: Hif1alpha, VEGF; DNA repair pathway: PARP; microRNAS: miR21, miR7, mIR128a, mIR210; cancer stem cells: genes in NOTCH, HEDGEHOG, PTEN, WNT, TGFbeta pathways; immune modulation: Interleukin (IL-6, IL-10) and genes in the JAK/STAT, SMAD, TNFalpha. In principle the concept can be expanded to include any genetically related diseases.

Exemplary potential applications of the complementary interacting nanoparticles described herein in which 2, 3, 4, 5, 6 or more independent agents are coupled to a nanoparticle include using one or more agents to target a macromolecular structure or a cell and using the second one to alter the function/properties of the macromolecule or cell, e.g., using a protein to target a cell and using a toxin or cell death protein to kill the targeted cell, using an siRNA to silence genes, or using a fluorescent particle for visualization, or using a chemical or protein to target a protein within a complex and another one to alter the function of a different component of the complex.

In certain embodiments, the complementary interacting nanoparticles described herein may comprise one or more agents. In further preferred embodiments, the agent can be conjugated to the nanoparticle. Conjugated can be understood as attached, linked, mixed, or otherwise present on or in a magnetoliposome. For example, an agent can be conjugated by covalent or ionic linkage, by use of a chelate or other linker moiety. As used herein, conjugation of an agent to a nanoparticle does not disrupt the desired activity of the agent.

The agent can comprise any material or compound or composition or agent for in vivo or in vitro use for imaging, diagnostic or therapeutic treatment that can be enclosed in the inside the nanoparticle or can be conjugated with the nanoparticle without appreciably disturbing the physical integrity of the nanoparticle. A nanoparticle can comprise one or more agents of one or more types. For example, a nanoparticle can comprise a therapeutic agent, and the targeting of the agent can be followed by further conjugation with an imaging agent. Similarly, cocktails of therapeutic agents are typically used in the treatment of cancer. A nanoparticle can comprise more than one type of therapeutic agent.

Examples of agents include inhibitory nucleic acids, including but not limited to siRNAs, RNA or DNA aptamers, fluorescent dyes, small molecules, RNA-DNA hybrids with split functionalities, split lipase, split GFP, proteins, therapeutic agents and imaging agents (for example gadolinium, manganese, chromium, or iron).

In certain embodiments, the complementary interacting nanoparticles described herein operate by forming inhibitory nucleic acid molecules once in target cells. Such inhibitory nucleic acids include single and double stranded nucleic acid molecules (e.g., DNA, RNA, and analogs thereof) that bind a nucleic acid molecule that encodes target RNA (e.g., antisense oligonucleotide molecules, siRNA, shRNA) as well as nucleic acid molecules that bind directly to a target polypeptide to modulate its biological activity (e.g., aptamers).

Catalytic RNA molecules or ribozymes that include an antisense target RNA sequence of the present disclosure can be used to inhibit expression of target RNAs in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

siRNA

The complementary interacting nanoparticles described herein (e.g., cubes and anti-cubes) may be employed to deliver one or more siRNAs to cells, and preferably in a split manner whereby the siRNA functionalities are split amongs the initial cubes and anti-cubes and activated only upon the interaction of the cubes/anti-cubes and their subsequent disassembly with the concomitant formation of the functional duplexes comprising the complementary strands of each of the initial nanoparticles. In therapeutic embodiments, the target RNA of the split siRNA functionality is a disease related gene. For example, in a non-limiting embodiment, the target RNA is a gene that is involved in HIV. In another embodiment, the target RNA gene is a gene that is involved in cancer development or progression. In another embodiment, target RNA expression is reduced in a virus infected cell. In another embodiment, the target RNA encodes apoptosis inhibitor proteins and the cells are infected with HIV. RNAi is a method for decreasing the cellular expression of specific proteins of interest (reviewed in Tuschl, ChemBioChem 2:239-245, 2001; Sharp, Gene Dev 15:485-490, 2000; Hutvagner and Zamore, Curr Opin Genet Devel 12:225-232, 2002; and Hannon, Nature 418: 244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the disclosure, the complementary interacting nanoparticles described herein deliver a RNA duplex comprising between eight and nineteen consecutive nucleobases of a nucleobase oligomer of the disclosure. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to 30 or more nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Gene Dev 16:948-958, 2002. Paul et al. Nat Biotechnol 20:505-508, 2002; Sui et al. Proc Natl Acad Sci USA 99:5515-5520, 2002; Yu et al. Proc Natl Acad Sci USA 99:6047-6052, 2002; Miyagishi et al. Nat Biotechnol 20:497-500, 2002; and Lee et al. Nat Biotechnol 20:500-505, 2002, each of which is hereby incorporated by reference. In certain embodiments, the sense strand of the double stranded siRNA is split into two smaller oligonucleotides, also referred to as three stranded siRNA.

The invention encompasses stabilized complementary interacting nanoparticles described herein having further modifications that protect against 3' and 5' exonucleases as well as endonucleases. Such modifications desirably maintain target affinity while increasing stability in vivo. In various embodiments, the complementary interacting nanoparticles described herein include chemical substitutions at the ribose and/or phosphate and/or base positions of a given nucleobase sequence. For example, complementary nanoparticles of the invention include chemical modifications at the 2' position of the ribose moiety, circularization of the aptamer, 3' capping and 'spiegelmer' technology. Complementary nanoparticles having A and G nucleotides sequentially replaced with their 2'-OCH3 modified counterparts are particularly useful in the methods of the invention. Such modifications are typically well tolerated in terms of retaining affinity and specificity. In various embodiments, complementary nanoparticles described herein include at least 10%, 25%, 50%, or 75% modified nucleotides. In other embodiments, as many as 80-90% of the complementary nanoparticles described herein contain stabilizing substitutions. In other embodiments, 2'-OMe containing nanoparticles are synthesized. Such nanoparticles are desirable because they are inexpensive to synthesize and natural polymerases do not accept 2'-OMe nucleotide triphosphates as substrates so that 2'-OMe nucleotides cannot be recycled into host DNA. Using methods described herein, complementary nanoparticles described herein will be selected for increased in vivo stability. In one embodiment, complementary nanoparticles described herein having 2'-F and 2'-OCH3 modifications are used to generate nuclease resistant aptamers. In other embodiments, the nucleic acids of the invention have one or more locked nucleic acids (LNA). LNA refers to a modified RNA nucleotide. The ribose of the LNA is modified with an extra bridge connecting the 2' oxygen and the 4' carbon which locks the ribose into the North or 3'-endo conformation. See e.g., Kaur, H. et al., Biochemistry, vol. 45, pages 7347-55; and Koshkin, A. A., et al., Tetrahedron, vol. 54, pages 3607-3630. In other embodiments, one or more nucleic acids of the invention incorporate a morpolino structure where the nucleic acid bases are bound to morpholine rings instead of deoxyribose rings and are linked through phosphorodiamidate groups instead of phosphates. See eg., Summerton, J. and Weller, D., Antisense & Nucleic Acid Drug Development, vol. 7, pages 187-195. Yet other modifications, include (PS)-phosphate sulfur modifications wherein the phosphate backbone of the nucleic acid is modified by the substitution of one or more sulfur groups for oxygen groups in the phosphate backbone. Other modifications that stabilize nucleic acids are known in the art and are described, for example, in U.S. Pat. No. 5,580,737; and in U.S. Patent Application Publication Nos. 20050037394, 20040253679, 20040197804, and 20040180360.

Agents

The complementary nanoscaffolds (e.g., cubes and anti-cubes) described herein may also comprise targeting or tropism agent such that the nanoscaffolds are targeted to a delivery site. For example, the targeting agent may be a ligand, e.g. a peptide ligand that has specific cell surface binding partners, e.g., ligand receptors which are preferentially exhibited on the surface of a target cell. As used herein, "receptor" and "ligand" refer to two members of a specific binding pair that are binding partners. A receptor is that member of the pair that is found localized on the surface of the target; the ligand is the member of the pair that is found on the surface of the nanoparticle. Accordingly, in certain embodiments, the invention features a nanoparticle comprising a member of a binding pair, or a fragment thereof that retains the capacity to specifically bind the other member of the binding pair, on its surface and the other member of that binding pair, or a fragment thereof that retains the capacity to specifically bind its partner, is present on the surface of a target. In certain embodiments, the targeting agent may be an antibody, for example a single-chain antibody, for which a binding partner would include an antigen thereof, or a fragment, derivative or variant thereof that retains the capacity to bind to the single-chain antibody.

The complementary nanoscaffolds (e.g., cubes and anti-cubes) described herein may also comprise a further therapeutic agent that may be delivered to a site. A therapeutic agent may be a molecule, atom, ion, receptor and/or other entity which is capable of detecting, identifying, inhibiting, treating, catalyzing, controlling, killing, enhancing or modifying a target such as a protein, glyco protein, lipoprotein, lipid, a targeted cell, a targeted organ, or a targeted tissue. In certain cases, the therapeutic agent is a radiotherapeutic agent, and can be selected from, but is not limited to radioactive gadolinium, radioactive boron, and radioactive iodine.

In certain examples, the agent can be, but is not limited to: drugs, such as antibiotics, analgesics, hypertensives, cardiotonics, and the like, such as acetaminaphen, acyclovir, alkeran, amikacin, ampicillin, aspirin, bisantrene, bleomycin, neocardiostatin, carboplatin, chloroambucil, chloramphenicol, cytarabine, daunomycin, doxorubicin, fluorouracil, gentamycin, ibuprofen, kanamycin, meprobamate, methotrexate, novantrone, nystatin, oncovin, phenobarbital, polymyxin, probucol, procarbabizine, rifampin, streptomycin, spectinomycin, symmetrel, thioguanine, tobramycin, temozolamide, trimethoprim, cisplatin, oxaliplatin, mechlorethamine, cyclophosphamide, chlorambucil, azathioprine, mercaptopurine, vinca alkaloids, taxanes, vincristine, vinblastine vinorelbine, vindesine, etoposide, teniposide, paclitaxel, irinotecan, topotecan, amsacrine, etoposide, etoposide phosphate, teniposide, and dactinomycinand valban; diphtheria toxin, gelonin, exotoxin A, abrin, modeccin, ricin, radioactive gadolinium, radioactive boron, and radioactive iodine; or toxic fragments thereof; metal ions, such as the alkali and alkaline-earth metals; radionuclides, such as those generated from actinides or lanthanides or other similar transition elements or from other elements, such as $^{51}$Cr, $^{47}$Sc, $^{67}$Cu, $^{67}$Ga, $^{82}$Rb, $^{89}$Sr, $^{88}$Y, $^{90}$Y, $^{99m}$Tc, $^{105}$Rh, $^{109}$Pd, $^{111}$In, $^{115m}$In, $^{125}$I, $^{131}$I, $^{140}$Ba, $^{140}$La, $^{149}$Pm, $^{153}$Sm, $^{159}$Gd, $^{166}$Ho, $^{175}$Yb, $^{177}$Lu, $^{186}$Re, $^{188}$Re, $^{194}$Ir, and $^{199}$Au; signal generators, which includes anything that results in a detectable and measurable perturbation of the system due to its presence, such as fluorescing entities, phosphorescence entities and radiation; signal reflectors, such as paramagnetic entities, for example, Fe, Gd, Cr, or Mn; chelated metal, such as any of the metals given above, whether or not they are radioactive, when associated with a chelant; signal absorbers, such as contrast agents and electron beam opacifiers, for example, Fe, Gd, Cr, or Mn; antibodies, including monoclonal antibodies and anti-idiotype antibodies; antibody fragments; hormones; biological response modifiers such as interleukins, interferons, viruses and viral fragments; diagnostic opacifiers; and fluorescent moieties. Other pharmaceutical materials include scavenging agents such as chelants, antigens, antibodies or any moieties capable of selectively scavenging therapeutic or diagnostic agents.

Other examples of therapeutic agents include antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable therapeutic moieties include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The complementary nanoscaffolds described herein (e.g., cubes and anti-cubes) may be directed to target sites, e.g. as described above. Preferred target sites comprise cancer cells, solid tumors, sites of inflammation and damaged bone or tissue.

For example, complementary nanoparticles described herein may further comprise an antibody or a peptide that acts as a targeting moiety to enable specific binding to a target cell bearing a target molecule, e.g., a cell surface marker to which the antibody or peptide is directed or a disease-specific marker to which the antibody or peptide is directed. The nanoparticle may further comprise a nucleotide, e.g. an oligonucleotide, that acts as a targeting moiety to enable specific binding to a target cell bearing a target molecule. For example, the oligonucleotide may be an aptamer that binds a specific target molecule.

A number of "molecular beacons" (often fluorescence compounds) can be attached to the complementary nanoparticles described herein to provide a means for signaling the presence of, and quantifying, a target analyte. Molecular beacons, for example, employ fluorescence resonance energy transfer-based methods to provide fluorescence signals in the presence of a particular analyte/biomarker of interest. In preferred embodiments, the term "molecular beacon" refers to a molecule or group of molecules (i.e., a nucleic acid molecule hybridized to an energy transfer complex or chromophore(s)) that can become detectable and can be attached to a nanoparticle under preselected conditions. Similarly, amplifying fluorescent polymers (AFPs) can be utilized in the present invention. An AFP is a polymer containing several chromophores that are linked together. As opposed to isolated chromophores that require 1:1 interaction with an analyte in conventional fluorescence detection, the fluorescence of many chromophores in an AFP can be influenced by a single molecule. For example, a single binding event to an AFP can quench the fluorescence of many polymer repeat units, resulting in an amplification of the quenching. Quenching is a process which decreases the intensity of the fluorescence emission. Molecular beacons and AFPs, including their methods for preparation, that can be used in the present invention are described in numerous patents and publications, including U.S. Pat. No. 6,261,783.

Any protein can be coupled to complementary nanoscaffolds described herein. For instance, glycoproteins are most easily coupled, as they can be oxidized to generate an active aldehyde group. Other proteins can be coupled via their —COOH group(s) but with lower efficiency. However, other means known in the art, such as di-imide reagents, e.g. carbodiimide can be used to couple proteins lacking sugars to the nanoparticles.

Polyethylene Glyocol (PEG) chains can be conjugated to the complementary nanoscaffolds described herein. PEG chains render the nanotubes highly water-soluble. PEG-phospholipids (PEG-PL) have been used in the formation of micelles and liposomes for drug delivery (Adlakha-Hutcheon, G.; Bally, M. B.; Shew, C. R.; Madden, T. D. Nature Biotech. 1999, 17, 775-779; Meyer, O.; Kirpotin, D.; Hong, K.; Sternberg, B.; Park, J. W.; Woodle, M. C.; Papahadjopoulos, D. J. Biol. Chem. 1998, 273, 15621-15627; Papahadjopoulos, D.; Allen, T. M.; Gabizon, A.; Mayhew, E.; Matthay, K.; Huang, S. K.; Lee, K. D.; Woodle, M. C.; Lasic, D. D.; Redemann, C.; Martin, F. J. Proc. Nat. Acad. Sci. USA. 1991, 88, 11460-11464).

Functional groups can be coupled to the complementary nanoscaffolds described herein, for instance the functional group can be a reactive functional group. Suitable functional groups include, but are not limited to, a haloacetyl group, an amine, a thiol, a phosphate, a carboxylate, a hydrazine, a hydrazide an aldehyde or a combination thereof. Other functional groups include groups such as a reactive functionality or a complementary group. In addition, RNA functional groups can be attached, as for example ribozymes or riboswitch aptamers.

The complementary nanoscaffolds described herein can be used for attachment of small molecules for specific interactions with nucleic acids, carbohydrates, lipids, proteins, antibodies, or other ligands.

The complementary nanoparticles described herein can have dyes attached. The dye is can be a fluorescent dye, or a plurality of fluorescent dyes. Suitable dyes include, but are not limited to, YOYO-1, JOJO-1, LOLO-1, YOYO-3, TOTO, BOBO-3, SYBR, SYTO, SYTOX, PicoGreen, Oli-Green, and combinations thereof. Other dyes include, thiazole orange, oxazole yellow, or non-intercalating dyes such as fluorescein, rhodamine, cyanine or coumarin based dyes, and combinations thereof. Other suitable dyes include, but are not limited to, 4-acetamido-4'-isothiocyanatostilbene-2, 2'disulfonic acid; acridine and derivatives: acridine, acridine isothiocyanate; 5-(2'-aminoethyl)aminonap-hthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethyl-couluarin (Coumaran 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,-2'-disulfonic acid; 4,4'-diisothiocyanatostilbene-2,2'-disulfonic acid; 5-[dimethylamino] naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amin-ofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Ciba-cron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalocyanine; and naphthalo cyanine. Suitable dyes for use in the nanoparticles of the present invention include, without limitation, a family of homodimeric cyanine DNA intercalating dyes from Molecular Probes that cover the visible spectrum, such as YOYO-1 (488/509), JOJO-1 (532/545), LOLO-1 (565/579), and YOYO-3 (612/631), SYBR-101 (488/505) and SYTO-62 (652/676). Given sufficient detection SN, dyes are mixed in various ratios in a single particle such that, for example, different fluorescence spectra are obtained from mixtures of just 2 dyes.

According to the invention, one or more therapeutic, diagnostic, or delivery agents are directly included in the complementary nanoparticles described herein. In certain embodiments, the delivery agent can be a targeting agent. Targeting agents are used to direct the nanoparticles described herein to a tissue or cell target. An exemplary embodiment of a targeting agent is an antibody. For example, antibodies suitable for use as targeting agents in the present invention include antibodies directed to cell surface antigens which cause the antibody-nanoparticle complex to be internalized, either directly or indirectly. For example, in the treatment of cancer, suitable antibodies include antibodies to CD33 and CD22. CD33 and CD22 that are over-expressed and dimerized on lymphomas.

In certain preferred embodiments of the invention, biotin is conjugated to the complementary nanoscaffolds described herein. For example, the nanoparticles of the invention can be further functionalized using biotin-streptavidin interactions to immobilize molecules inside or outside the polyhedra, e.g. polyhedral cages. For example, streptavidin can be conjugated to guanosine mono-phosphothioate (GMPS)-modified tectoRNAs by means of a biotin linker. In certain preferred embodiments, the biotin linker is incorporated to a mono-phosphothioate at the 5' position of tectoRNAs.

A wide variety of particle sizes are suitable for the present invention. In certain aspects, the particle has a diameter of about 10 nanometers to about 10 microns. Preferably the particle diameter is about 10 to 700 nanometers, and more preferably, the diameter of about 10 nanometers to about 100 nanometers.

The complementary nanoscaffolds described herein have a number of uses. For example, the nanoparticles can be used in drug delivery, imaging, nanocircuits, cell growth surfaces, medical implants, medical testing, or gene therapy, and particularly, where it is desirable to split functionality.

In one particular embodiment, the complementary nanoscaffolds described herein (e.g., cubes and anti-cubes) as described herein can be used in biological meshes. In one exemplary embodiment, the invention as described herein may find use as a biosensor in, for example, pathogen detection. In one particular embodiment, self-assembling nano-meshes are used to attach biosensors for pathogen detection or for x-ray crystallography by placing multiple copies of a protein or functional RNAs, for example, on the mesh. Biosensors for pathogen detection are advantageously employed in bioterrorism capacities.

In another exemplary embodiment, the complementary nanoscaffolds described herein (e.g., cubes and anti-cubes) of the invention, as described herein, are employed as skeletons or scaffolds for tissue growth.

These uses are exemplary, and not considered to be limiting.

Functional Hybrid Arms

The complementary nanoscaffolds described herein (e.g., cubes and anti-cubes) may comprise RNA/DNA and DNA/RNA hybrid elements, e.g., hybrid functional arms, comprising one or more latent functionalities (e.g., siRNA, optical markers, aptambers, promoters). Control over the coincident delivery of different functionalities and their synchronized intracellular activation can significantly contribute to the biomedical applications of RNA and DNA nanoparticles. Described herein are several different, yet intrinsically related methodologies based on activation of RNA interference (RNAi) in human cells. It is newly described herein how RNA and DNA nanoscaffolds can be functionalized with multiple short interfering RNAs (siRNAs) (e.g. siRNAs targeting six different parts of HIV-1) as well as RNA-DNA hybrids. The RNA-DNA hybrids cannot be diced and thus are not active. Cognate hybrids re-associated through ssDNA toeholds interactions and released either the functional RNA nanoparticles or siRNAs. Several cell culture experiments demonstrated FRET and RNAi activation by conditional triggering of split functionalities in cells. The key idea is to split the functional entity (e.g. Dicer Substrate RNAs, referred to herein as DS RNAs or DsiRNAs, RNA aptamers, FRET pair of dyes) into two complementary nanoparticles (for example cube and anti-cube). The resulting inactive hybrids in two complementary nanoparticles would interact under physiological conditions and trigger the thermodynamically favorable re-association process when both of the cognate hybrids were present in close proximity. The re-association released the split functionalities and restored their original function.

Compositions

The invention, in part, pertains to a drug delivery composition comprising at least two complementary and interacting nanoparticles (cubes and anti-cubes) as described herein. The cubes and anti-cubes may be comprised of a plurality of single stranded DNA or RNA molecules which are reverse complements of one another. That is, if the cube comprises six single-stranded DNA molecules, the anti-cube comprises six single-stranded DNA molecules which are the reverse complement of the strands of the cube. Many other configurations are contemplated, in terms of overall shape (3D and 2D shapes are contemplated) and the constitution and number of RNA and DNA strands as described herein elsewhere, as well as the inclusion of additional functionalities, including hybrid arms. Any of these configurations may be formulated into a drug delivery composition. The drug delivery composition of the invention can gain entry into a cell or tissue.

Advantageously, the drug delivery composition of the invention provides for a more controlled delivery of an active agent, especially a therapeutic agent, to a site of action at an optimum rate and therapeutic dose. Thus, improvements in therapeutic index may be obtained by modulating the distribution of the active ingredient in the body. Association of the active ingredient with a delivery system enables, in particular, its specific delivery to the site of action or its controlled release after targeting the action site. By reducing the amount of active ingredient in the compartments in which its presence is not desired, it is possible to increase the efficacy of the active ingredient, to reduce its toxic side effects and even modify or restore its activity.

Fine-Tuning of Physical Characteristics

As demonstrated herein, the relationship between the ratio of DNA to RNA single-strands in the cube and anti-cube affects the degree of thermal stability, chemical reactivity, and immunogenicity, and other characteristics in a predictable manner.

It was surprisingly observed, as discussed in the Examples and shown in FIG. 1 that as the ratio of DNA to RNA is decreased (i.e., increasing the ratio of RNA to DNA), the thermal stability of the cubes/anti-cubes is increased. Thus, there is an inverse relationship between the ratio of DNA to RNA and temperature stability. Accordingly, cubes/anti-cubes having 6DNAs and no RNA are expected to have the lowest thermal stability, whereas cubes/anti-cubes having 6RNAs and no DNA are expected to have the highest thermal stability. And, 5DNA/1RNA, 4DNA/2RNA, 3DNA/3RNA, 2DNA/4RNA, and 1DNA/5RNA cubes/anti-cubes are expected to have increasing thermal stability.

It was also surprisingly observed, as discussed in the Examples and shown in FIG. 1 that as the ratio of DNA to RNA is decreased (i.e., increasing the ratio of RNA to DNA), the immunogenicity of the cubes/anti-cubes is increased. Thus, there is an inverse relationship between the ratio of DNA to RNA and immunogenicity. Accordingly, cubes/anti-cubes having 6DNAs and no RNA are expected to have the lowest degree of immunogenicity, whereas cubes/anti-cubes having 6RNAs and no DNA are expected to have the highest degree of immunogenicity. And, 5DNA/1RNA, 4DNA/2RNA, 3DNA/3RNA, 2DNA/4RNA, and 1DNA/5RNA cubes/anti-cubes are expected to have increasing levels of immunogenicity.

It was also surprisingly observed, as discussed in the Examples and shown in FIG. 1 that as the ratio of DNA to RNA is decreased (i.e., increasing the ratio of RNA to DNA), the stability of the nanoparticles in blood serum is generally increased. Thus, there is generally an inverse relationship between the ratio of DNA to RNA and stability in blood serum. Accordingly, cubes/anti-cubes having 6DNAs and no RNA are expected to have the lowest degree of blood serum stability, whereas cubes/anti-cubes having 6RNAs and no DNA are expected to have a higher degree of serum stability. And, 5DNA/1RNA, 4DNA/2RNA, 3DNA/3RNA, 2DNA/4RNA, and 1DNA/5RNA cubes/anti-cubes are expected to have generally increasing levels of blood serum stability. It was further surprisingly observed that cubes or anti-cubes having the same amount of DNA and RNA were found to have almost the same or more stability as 1DNA/5RNA or 6RNA particles.

Second Therapeutic Agents

In certain preferred embodiments, the drug delivery compositions described herein comprising the complementary nanoscaffolds (cubes and anti-cubes) can comprise a second therapeutic agent. In some embodiments, the composition comprising nanoparticles and the second therapeutic agent are administered simultaneously, either in the same composition or in separate compositions. In some embodiments, the nanoparticle composition and the second therapeutic agent are administered sequentially, i.e., the nanoparticle composition is administered either prior to or after the administration of the second therapeutic agent. The term "sequential administration" as used herein means that the drug in the nanoparticle composition and the second agent are administered with a time separation of more than about 15 minutes, such as more than about any of 20, 30, 40, 50, 60 or more minutes. Either the nanoparticle composition or the chemotherapeutic agent may be administered first. The nanoparticle composition and the chemotherapeutic agent are contained in separate compositions, which may be contained in the same or different packages. In some embodiments, the administration of the nanoparticle composition and the second therapeutic agent are concurrent, i.e., the administration period of the nanoparticle composition and that of the second therapeutic agent overlap with each other. In some embodiments, the administration of the nanoparticle composition and the second therapeutic agent are non-concurrent. For example, in some embodiments, the administration of the nanoparticle composition is terminated before the second therapeutic agent is administered. In some embodiments, the administration of the second therapeutic agent is terminated before the nanoparticle composition is administered.

The second therapeutic agent is selected from, but not limited to chemotherapeutic agents, cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories, antianxiety agents, immunosuppressive agents, immunomodulatory agents, antimigraine agents, sedatives/hypnotics, antianginal agents, antipsychotics, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, anti-infectives, bronchodialators, hormones, hypoglycemic agents, hypolipidemic agents, proteins, peptides, nucleic acids, agents useful for erythropoiesis stimulation, antiulcer/antireflux agents, antinauseants/antiemetics and oil-soluble vitamins, or combinations thereof.

When the second therapeutic agent is a chemotherapeutic agent, the chemotherapeutic agent is selected from, but not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate;

trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlornaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2''-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

Pharmaceutical/Chemotherapeutic Compositions

Reference to a chemotherapeutic agent herein applies to the chemotherapeutic agent or its derivatives and accordingly the invention contemplates and includes either of these embodiments (agent; agent or derivative(s)). "Derivatives" or "analogs" of a chemotherapeutic agent or other chemical moiety include, but are not limited to, compounds that are structurally similar to the chemotherapeutic agent or moiety or are in the same general chemical class as the chemotherapeutic agent or moiety. In some embodiments, the derivative or analog of the chemotherapeutic agent or moiety retains similar chemical and/or physical property (including, for example, functionality) of the chemotherapeutic agent or moiety.

The invention also relates to pharmaceutical or diagnostic compositions comprising the nanoparticles of the invention and a pharmaceutically acceptable carrier. The phrase "pharmaceutically acceptable carrier" is art recognized and includes a pharmaceutically acceptable material, composition or vehicle, suitable for administering compounds used in the methods described herein to subjects, e.g., mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in Remington's Pharmaceutical Sciences, Mack Publishing Company, a standard reference text in this field.

Methods of Treatment

The methods of the invention encompass method of treating or preventing diseases or disorders by administering to subjects in need thereof an effective amount of complementary nanoparticles (e.g., cube and anti-cube), preferably with one or more split functionalities as described herein. Accordingly, a number of diseases or disorders are suitable for treatment according to the methods of the invention. Examples include, but are not limited to, Adenoma, Ageing, AIDS/HIV, Alopecia, Alzheimer's disease, Anemia, Arthritis, Asthma, Atherosclerosis, Cancer, Cardiac conditions or disease, Diabetes mellitus, Foodborne illness, Hemophilia A-E, Herpes, Huntington's disease, Hypertension, Headache, Influenza, Multiple Sclerosis, Myasthenia gravis, Neoplasm, Obesity, Osteoarthritis, Pancreatitis, Parkinson's disease, Pelvic inflammatory disease, Peritonitis, Periodontal disease, Rheumatoid arthritis, Sepsis, Sickle-cell disease, Teratoma, Ulcerative colitis, and Uveitis.

The methods of the invention further encompass diagnostics.

The methods may be practiced in an adjuvant setting. "Adjuvant setting" refers to a clinical setting in which, for example, an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated. The methods provided herein may also be practiced in a neoadjuvant setting, i.e., the method may be carried out before the primary/definitive therapy. Thus, in some embodiments, the individual has previously been treated. In other embodiments, the individual has not previously been treated. In some embodiments, the treatment is a first line therapy.

In aspects, the invention features methods for inhibiting or reducing the expression of a target gene in a cell. In embodiments, the methods involve contacting the cell with a therapeutically effective amount of at least two reverse complementary nanoparticles to a subject.

In some aspects, the invention features methods for killing a pathogen or pathogen-infected cell. In embodiments, the methods involve contacting the cell with a therapeutically effective amount of at least two reverse complementary nanoparticles to a subject.

In aspects, the invention features methods for inhibiting replication of a pathogen in a cell. In embodiments, the methods involve contacting the cell with a therapeutically effective amount of at least two reverse complementary nanoparticles to a subject.

In aspects, the invention features methods for reducing pathogenic burden in a subject. In embodiments, the methods involve administering a therapeutically effective amount of at least two reverse complementary nanoparticles to a subject. In embodiments, the subject is at risk of developing a pathogenic infection. In embodiments, the subject is diagnosed with having a pathogenic infection.

In aspects, the invention features methods for treating or preventing a pathogenic infection in a subject. In embodiments, the methods involve administering a therapeutically effective amount of at least two reverse complementary nanoparticles to a subject. In embodiments, the methods reduce the pathogenic burden, thereby treating or preventing the pathogenic infection. In embodiments, the methods induce death in infected cell, thereby treating or preventing the pathogenic infection.

In any of the above aspects and embodiments, the subject can be a mammal (e.g., human).

In any of the above aspects and embodiments, the pathogen can be a virus, bacteria, fungus, or parasite. In some embodiments, the pathogen is a virus (e.g., HIV or a flavivirus).

In any of the above aspects and embodiments, the methods can involve further contacting the cell with a therapeutically effective amount of a second therapeutic agent or administering a therapeutically effective amount of the second therapeutic agent to the subject. The second therapeutic agent can treat the pathogenic infection or the symptoms associated with pathogenic infection. For example, the second therapeutic agent can be an anti-viral agent, an anti-bacterial agent, an anti-fungal agent, or an anti-parasitic agent. Such agents are well known in the art, and it is within the purview of a physician to select and determine the appropriate dosage of the second therapeutic agent. See, e.g., *Drug Information Handbook: A Comprehensive Resource for All Clinicians and Healthcare Professionals*, 20.sup.th Ed., C. F. Lacy et al. (eds.) (Lexi-Comp 2011); *Johns Hopkins ABX Guide: Diagnosis & Treatment of Infectious Diseases*, 2.sup.nd Ed., J. G. Bartlett et al. (eds.) (Jones & Bartlett Publishers 2010); and Mandell, Douglas, and Bennett's *Principles and Practice of Infectious Diseases: Expert Consult Premium Edition*, 7.sup.th Ed., G. L. Mandell (ed.) (Churchill Livingstone 2009); *The Sanford Guide to Antimicrobial Therapy* 2012, 42.sup.nd Ed., D. N. Gilbert et al. (eds.) (Antimicrobial Therapy 2012); *Clinical Infectious Disease* 2013, 11.sup.th Ed., C. G. Weber (ed.) (Pacific Primary Care Software 2012), the contents of which are hereby incorporated by reference in their entirety.

In aspects, the invention features methods for killing a neoplastic cell. In embodiments, the methods involve contacting the cell with a therapeutically effective amount of at least two reverse complementary nanoparticles to a subject.

In aspects, the invention features methods for treating a subject having a neoplasia. In embodiments, the methods involve administering a therapeutically effective amount of at least two reverse complementary nanoparticles to a subject.

In embodiments, the neoplastic cell is a cancer cell which is present in a solid tumor. In embodiments, the cancer is selected from the group consisting of breast cancer, prostate cancer, melanoma, glioblastomas, colon cancer, ovarian cancer, and non-small cell lung cancer.

In some embodiments, the second therapeutic agent that may be administered is an anti-cancer agent. Anti-cancer agents are well known in the art, and any such agent is suitable for use in the present invention. See, e.g., *Anticancer Drugs: Design, Delivery and Pharmacology* (Cancer Etiology, Diagnosis and Treatments) (eds. Spencer, P. & Holt, W.) (Nova Science Publishers, 2011); *Clinical Guide to Antineoplastic Therapy: A Chemotherapy Handbook* (ed. Gullatte) (Oncology Nursing Society, 2007); *Chemotherapy and Biotherapy Guidelines and Recommendations for Practice* (eds. Polovich, M. et al.) (Oncology Nursing Society, 2009); *Physicians' Cancer Chemotherapy Drug Manual* 2012 (eds. Chu, E. & DeVita, Jr., V. T.) (Jones & Bartlett Learning, 2011); DeVita, Hellman, and Rosenberg's *Cancer: Principles and Practice of Oncology* (eds. DeVita, Jr., V. T. et al.) (Lippincott Williams & Wilkins, 2011); and *Clinical Radiation Oncology* (eds. Gunderson, L. L. & Tepper, J. E.) (Saunders) (2011), the contents of which are hereby incorporated by reference in their entirety.

For example, nonlimiting examples of anti-cancer agents include Abiraterone Acetate, Afatinib, Aldesleukin, Alemtuzumab, Alitretinoin, Altretamine, Amifostine, Aminoglutethimide Anagrelide, Anastrozole, Arsenic Trioxide, Asparaginase, Azacitidine, Azathioprine, Bendamustine, Bevacizumab, Bexarotine, Bicalutamide, Bleomycin, Bortezomib, Busulfan, Capecitabine, Carboplatin, Carmustine, Cetuximab, Chlorambucil, Cisplatin, Cladribine, Crizotinib, Cyclophosphamide, Cytarabine, Dacarbazine, Dactinomycin, Dasatinib, Daunorubicin, Denileukin diftitox, Decitabine, Docetaxel, Dexamethasone, Doxifluridine, Doxorubicin, Epirubicin, Epoetin Alpha, Epothilone, Erlotinib, Estramustine, Etinostat, Etoposide, Everolimus, Exemestane, Filgrastim, Floxuridine, Fludarabine, Fluorouracil, Fluoxymesterone, Flutamide, folate linked alkaloids, Gefitinib, Gemcitabine, Gemtuzumab ozogamicin, GM-CT-01, Goserelin, Hexamethylmelamine, Hydroxyureas, Ibritumomab, Idarubicin, Ifosfamide, Imatinib, Interferon alpha, Interferon beta, Irinotecan, Ixabepilone, Lapatinib, Leucovorin, Leuprolide, Lenalidomide, Letrozole, Lomustine, Mechlorethamine, Megestrol, Melphalan, Mercaptopurine, Methotrexate, Mitomycin, Mitoxantrone, Nelarabine, Nilotinib, Nilutamide, Octreotide, Ofatumumab, Oprelvekin, Oxaliplatin, Paclitaxel, Panitumumab, Pemetrexed, Pentostatin, polysaccharide galectin inhibitors, Procarbazine, Raloxifene, Retinoic acids, Rituximab, Romiplostim, Sargramostim, Sorafenib, Streptozocin, Sunitinib, Tamoxifen, Temsirolimus, Temozolamide, Teniposide, Thalidomide, Thioguanine, Thiotepa, Tioguanine, Topotecan, Toremifene, Tositumomab, Trametinib, Trastuzumab, Tretinoin, Valrubicin, VEGF inhibitors and traps, Vinblastine, Vincristine, Vindesine, Vinorelbine, Vintafolide (EC145), Vorinostat, or a salt thereof.

In any of the above aspects and embodiments, the pathogen can be any known virus, bacteria, fungus, or parasite known in the art. See, e.g., *Clinical Infectious Disease* 2013, 11.sup.th Ed., C. G. Weber (ed.) (Pacific Primary Care Software 2012).

Exemplary bacterial pathogens include, but are not limited to, *Aerobacter, Aeromonas, Acinetobacter, Actinomyces israelli, Agrobacterium, Bacillus, Bacillus antracis, Bacteroides, Bartonella, Bordetella, Bortella, Borrelia, Brucella, Burkholderia, Calymmatobacterium, Campylobacter, Citrobacter, Clostridium, Clostridium perfringers, Clostridium tetani, Cornyebacterium, Corynebacterium diphtherias, Corynebacterium sp., Enterobacter, Enterobacter aerogenes, Enterococcus, Erysipelothrix rhusiopathiae, Escherichia, Francisella, Fusobacterium nucleatum, Gardnerella, Haemophilus, Hafnia, Helicobacter, Klebsiella, Klebsiella pneumoniae, Lactobacillus, Legionella, Leptospira, Listeria, Morganella, Moraxella, Mycobacterium, Neisseria, Pasteurella, Pasturella multocida, Proteus, Providencia, Pseudomonas, Rickettsia, Salmonella, Serratia, Shigella, Staphylococcus, Stentorophomonas, Streptococcus, Streptobacillus moniliformis, Treponema, Treponema pallidium, Treponema pertenue, Xanthomonas, Vibrio*, and *Yersinia*.

Exemplary viruses include, but are not limited to, Retroviridae (e.g., human immunodeficiency viruses, such as HIV-1 (also referred to as HDTV-III, LAVE or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g. influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviruses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of pathogenic fungi include, without limitation, *Alternaria, Aspergillus, Basidiobolus, Bipolaris, Blastoschizomyces, Candida, Candida albicans, Candida krusei, Candida glabrata* (formerly called *Torulopsis glabrata*), *Candida parapsilosis, Candida tropicalis, Candida pseudotropicalis, Candida guilliermondii, Candida dubliniensis,* and *Candida lusitaniae, Coccidioides, Cladophialophora, Cryptococcus, Cunninghamella, Curvularia, Exophiala, Fonsecaea, Histoplasma, Madurella, Malassezia, Plastomyces, Rhodotorula, Scedosporium, Scopulariopsis, Sporobolomyces, Tinea,* and *Trichosporon.*

Parasites can be classified based on whether they are intracellular or extracellular. An "intracellular parasite" as used herein is a parasite whose entire life cycle is intracellular. Examples of human intracellular parasites include *Leishmania, Plasmodium, Trypanosoma cruzi, Toxoplasma gondii, Babesia,* and *Trichinella spiralis.* An "extracellular parasite" as used herein is a parasite whose entire life cycle is extracellular. Extracellular parasites capable of infecting humans include *Entamoeba histolytica, Giardia lamblia, Enterocytozoon bieneusi, Naegleria* and *Acanthamoeba* as well as most helminths. Yet another class of parasites is defined as being mainly extracellular but with an obligate intracellular existence at a critical stage in their life cycles. Such parasites are referred to herein as "obligate intracellular parasites". These parasites may exist most of their lives or only a small portion of their lives in an extracellular environment, but they all have at lest one obligate intracellular stage in their life cycles. This latter category of parasites includes *Trypanosoma rhodesiense* and *Trypanosoma gambiense, Isospora, Cryptosporidium, Eimeria, Neospora, Sarcocystis,* and *Schistosoma.* In one aspect, the invention relates to the prevention and treatment of infection resulting from intracellular parasites and obligate intracellular parasites which have at least in one stage of their life cycle that is intracellular. In some embodiments, the invention is directed to the prevention of infection from obligate intracellular parasites which are predominantly intracellular. An exemplary and non-limiting list of parasites for some aspects of the invention include *Plasmodium* spp. such as *Plasmodium falciparum, Plasmodium malariae, Plasmodium ovale,* and *Plasmodium vivax* and *Toxoplasma gondii.* Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii.* Blood-borne and/or tissues parasites include *Plasmodium, Babesia microti, Babesia divergens, Leishmania tropica, Leishmania, Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii.*

Dosage

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Methods of Delivery

The nanoparticle compositions described herein can be administered to an individual (such as human) via various routes, such as parenterally, including intravenous, intraarterial, intraperitoneal, intrapulmonary, oral, inhalation, intravesicular, intramuscular, intra-tracheal, subcutaneous, intraocular, intrathecal, or transdermal. For example, the nanoparticle composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the nanoparticle composition is administrated intravenously. In some embodiments, the nanoparticle composition is administered orally.

The dosing frequency of the administration of the nanoparticle composition depends on the nature of the therapy and the particular disease being treated. For example, dosing frequency may include, but is not limited to, once daily, twice daily, weekly without break; weekly, three out of four weeks; once every three weeks; once every two weeks; weekly, two out of three weeks.

The administration of nanoparticles may be carried out at a single dose or at a dose repeated once or several times after a certain time interval. The appropriate dosage varies according to various parameters, for example the individual treated or the mode of administration.

The dosing frequency of the nanoparticle composition or the nanoparticle composition and the second therapeutic agent may be adjusted over the course of the treatment, based on the judgment of the administering physician.

When administered separately, the nanoparticle composition and the second therapeutic agent can be administered at different dosing frequency or intervals. For example, the nanoparticle composition can be administered weekly, while a second agent can be administered more or less frequently. In some embodiments, sustained continuous release formulation of the nanoparticle and/or second agent may be used. Various formulations and devices for achieving sustained release are known in the art. The doses required for the nanoparticle composition and/or the second agent may (but not necessarily) be lower than what is normally required when each agent is administered alone. Thus, in some embodiments, a subtherapeutic amount of the drug in the nanoparticle composition and/or the second agent are administered. "Subtherapeutic amount" or "subtherapeutic level" refer to an amount that is less than the therapeutic amount, that is, less than the amount normally used when the drug in the nanoparticle composition and/or the second agent are administered alone. The reduction may be reflected in terms of the amount administered at a given administration and/or the amount administered over a given period of time (reduced frequency).

A combination of the administration configurations described herein can be used. The combination therapy methods described herein may be performed alone or in conjunction with another therapy, such as surgery, radiation, chemotherapy, immunotherapy, gene therapy, and the like. Additionally, a person having a greater risk of developing the disease to be treated may receive treatments to inhibit and/or delay the development of the disease.

The dose of nanoparticle composition will vary with the nature of the therapy and the particular disease being treated. The dose should be sufficient to effect a desirable response, such as a therapeutic or prophylactic response against a particular disease.

Appropriate doses will be established by persons skilled in the art of pharmaceutical dosing such as physicians.

In certain embodiments, the siRNAs can be administered as bolaamphiphiles. Bolaamphiphiles have relatively low toxicities, long persistence in the blood stream, and most importantly, in aqueous conditions can form poly-cationic micelles thus, becoming amenable to association with siRNAs. Depending on the application, the extent of siRNA chemical protection, delivery efficiency, and further intracellular release can be varied by simply changing the type of bolaamphiphile used (see, e.g. Kim et al. Mol Ther Nucleic Acids. 2: e80, 2013, incorporated by reference in its entirety herein).

Kits

The disclosure provides kits for the treatment or prevention of disease. In one embodiment, the kit includes a therapeutic or prophylactic composition containing an effective amount of an agent of the invention (e.g., NPs) in unit dosage form. In some embodiments, the kit comprises a sterile container which contains a therapeutic or prophylactic compound; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the disclosure is provided together with instructions for administering it to a subject having or at risk of developing a disease. The instructions will generally include information about the use of the composition for the treatment or prevention of the disease (e.g., neoplasia or viral infection). In other embodiments, the instructions include at least one of the following: description of the compound; dosage schedule and administration for treatment or prevention of the disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Recombinant Polypeptide Expression

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Functionally-Interdependent Shape-Shifting Nucleic Acid Nanoparticles A new concept of dynamic interdependent nucleic acid nanoparticles is presented in the current disclosure and in the following Example. The approach relies on the physical interaction of two complementary nanoparticles with controllable thermodynamic, and chemical properties. Findings of the present invention also suggest that by simply optimizing the ratio between RNA and DNA strands entering the composition of assemblies one can create nanoparticles with optimal immunomodulatory properties when activation of the immune system is desirable (e.g., vaccines and immunotherapy). After interaction of the cognate nanoparticles both in vitro and in human cells, demonstrated in three different cell lines, constructs undergo isothermal shape-switching resulting in activation of one or more functionalities including RNAi, optical response, transcription and split aptamer re-assembly. Importantly, only two nanoparticles are required to simultaneously activate multiple functionalities and no ssRNA or ssDNA toeholds are needed to initiate the interaction. Moreover, in the case of co-transcriptional assemblies, only one specifically designed DNA nanoparticle is needed to efficiently produce an RNA counterpart. Overall, the presented strategy allows for the use of simple, multifunctional, and conditionally activated nanoparticles and provides a promising future for their use in nanobioscience.

Abstract

This Example introduces a new concept that utilizes cognate nucleic acid nanoparticles which are fully complementary and functionally-interdependent to each other (but initially inactive on their own prior to combination). In the described approach, the physical interaction between sets of designed nanoparticles initiates a rapid isothermal shape change which triggers the activation of multiple functionalities and biological pathways including transcription, energy transfer, functional aptamers and RNA interference. Only two complementary nanoparticles are required to trigger the activation of a multitude of functionalities. The individual nanoparticles are not active (i.e., before combination of two complementary nanoparticles) and have controllable kinetics of re-association and fine-tunable chemical and thermodynamic stabilities. Computational algorithms were developed to accurately predict melting temperatures of nanoparticles of various compositions and trace the process of their re-association in silico. Additionally, tunable immunostimulatory properties of described nanoparticles suggest that the particles that do not induce pro-inflammatory cytokines and high levels of interferons can be used as scaffolds to carry therapeutic oligonucleotides, while particles with strong interferon and mild proinflammatory cytokine induction may qualify as vaccine adjuvants. The presented concept in this Example provides a simple, cost-effective and straightforward model for the development of combinatorial regulation of biological processes in nucleic acid nanotechnology.

Introduction

RNAs are recognized to function as scaffolds, enzymes, switches, aptamers, as well as regulators of gene expression. The emerging field of RNA nanotechnology applies the current knowledge related to the structure and function of natural and artificial classes of RNAs to further address specific biomedical challenges by engineering nanodevices that can interact with cellular machinery. Building dynamic RNA nanoparticles that can communicate with one another will further improve the operation of functional systems. In fact, metabolite and cofactor responsive riboswitches and ribozymes or temperature sensing RNA thermometers are examples of dynamic RNAs autogenic in nature. Recently, RNA (30) and RNA-DNA hybrid (31) nanostructures have been reported that conditionally activate gene silencing in diseased cells in vitro and in vivo. The first approach is based on computer-generated two-stranded RNA switches that are activated only in the presence of specific mRNAs through interaction with a single-stranded (ss) RNA toehold of the switch (30). The second approach is based on RNA-DNA hybrids with split-functionalities activated only when two complementary copies are introduced into the same cell. Strand exchange, with subsequent intracellular activation of functionalities, is promoted by the interaction of complementary ssDNA (31) or ssRNA (32) toeholds. This concept was further used by other research groups for various applications (33). The simultaneous delivery and release of multiple functionalities was achieved by including them all into the longer hybrids (34). Alternatively, RNA and/or DNA nanoscaffolds can be decorated with multiple hybrids and activated by adding individual cognate DNA/RNA strands hybrids (35, 36). This approach requires, however, the simultaneous presence of the nanoparticle and six individual cognate hybrids in the same cell to activate six functionalities. While being efficient, previously described nanodevices typically demand intensive computer-assisted design and the use of specifically programmed toeholds.

Here, a series of interdependent complementary nucleic acid nanoparticles are designed that take advantage of dynamic interaction and shape switching to activate multiple functionalities. As opposed to previously described work, this new approach does not require any toeholds to initiate the interactions and their design principles are simple. Additionally, only two particles are required to simultaneously activate multiple functionalities. The novel interrelated nanoparticles are designed by simply taking the reverse complements of the existing RNA scaffolds and assembling them into the "anti-scaffolds" (FIG. 6). As a proof of concept, nucleic acid cubes (1) and their reverse complements, anti-cubes, are extensively characterized in this work (FIG. 1A). The interaction of cubes with anti-cubes at physiological conditions leads to conformational changes and to the swift formation of multiple duplexes or fibers that can further activate transcription, Förster resonance energy transfer (FRET), formation of functional aptamers, and specific gene silencing. It is shown that the immunostimulatory activity, thermodynamic stability, resistance to nuclease degradation, re-association rate, and cost of production for interdependent complementary nanoparticles vary tremendously depending on their composition (e.g., DNA vs RNA). Additionally, RNA hexameric ring (37) and recently engineered RNA and DNA triangle (38) scaffolds and their corresponding anti-scaffolds are explored.

Methods and Materials

RNA Synthesis.

DNAs, DS RNA strands and fluorescently labeled oligonucleotides were purchased from IDT. Scaffolds and aptamers containing RNAs were transcribed in vitro from PCR amplified double stranded DNA templates containing T7 RNA polymerase promoters. The transcription was stopped by adding the DNase. Purification of RNA was accomplished using 8 M urea, 8% (29:1) PAGE. The concentrations of all strands were measured using Beer-Lambert Law. The extinction coefficients of individual sequences were calculated by using IDT OligoAnalizer tools (https://www.idtdna.com/calc/analyzer)

Nanoparticle Assembly and Purification.

All nanoparticles were assembled by combining individual monomer components in equimolar concentrations. For cubes, the mixture of oligonucleotides in double-deionized water (ddiH$_2$O) was heated to 95° C. for 2 minutes, followed by snap-cooling to 45° C. and incubation for 30 minutes. For rings, mixtures were heated to 95° C. for 2 minutes, followed by snap cooling on ice for 2 minutes, and incubation at 30° C. for 30 minutes. An assembly buffer (1× concentration: 89 mM tris-borate (pH 8.3), 2 mM MgCl$_2$, 50 mM KCl, and 50 mM NaCl) was added following the heating step to all assemblies. For triangular complexes the mixtures in TMS buffer (50 mM TRIS pH=8.0, 100 mM NaCl and 10 mM MgCl$_2$) were heated to 80° C. for 2 mM and slow cooled (over 1 h) to 4° C. For co-transcriptional assembly of RNA cubes, DNA cubes and anti-cubes with split promoters were incubated together for 3.5 hours in the presence of T7 RNA polymerase, 100 mM DTT, and transcription buffer (400 mM HEPES-KOH, 10 mM Spermidine, 200 mM DTT, 120 mM MgCl$_2$). For purification, 8% non-denaturing native PAGE (37.5:1) was used in the presence of 89 mM Tris-borate, pH 8.3, 2 mM MgCl$_2$. Nanoparticle bands were visualized with UV lamp (short wavelength), cut and eluted with assembly buffer. The extinction coefficients of nanoparticles were calculated as the sum of extinction coefficients of individual sequences comprising of their composition. Electrophoretic mobility shift assays were performed for all assemblies on 8% non-denaturing native PAGE (37.5:1, 2 mM $MgCl_2$) and visualized with ChemiDoc MP System using total staining with ethidium bromide or fluorescently labeled oligonucleotides. Native-PAGE was run for 2 hours at 4° C., 300 volts.

UV-Melting Experiments.

Temperature-dependent absorption measurements were recorded at 260 nm on an Agilent 8453 spectrophotometer coupled with the Agilent 89090 Peltier Temperature Controller. This configuration contains a diode-array system to enhance the collection of all spectra. The instrument was calibrated by adding 100 μL of assembly buffer into a Starna Cells 100 μL sub-micro quartz fluorometer cell cuvette. Nanoparticles were diluted in assembly buffer for a final concentration and volume of 250 nM and 100 μL, respectively. The temperature was gradually increased from 20-25° C. to 60-85° C. and the absorbance was recorded every 1° C. increment while the temperature was held constant for 10 seconds. The Aglient UV/vis software was used to plot the melting temperature (Tm) based on the average between the initial and final absorbance values selected from the temperature range from the initial increase of the slope until a plateau was observed. The data was analyzed using Origin® Pro 2016 Graphing and Analysis software with a Boltzmann sigmoidal curve fit. All experiments were repeated at least three times and presented as the mean+/−SD.

Kinetics of Re-Association Determination.

To determine the kinetics, gel purified Cy5-tagged anti-cube was mixed with different compositions of cubes and were aliquoted at set time points to assess the extent of re-association. Based on the analysis of Tm curves, the relative rates of re-association were measured at 25° C. to ensure the complete assembly of all nanoparticles. In order to ensure the complete re-association, the cubes without a Cy5 tag were used in 10× excess. Upon addition of the cubes, the solution was pipetted up and down rapidly and equal aliquots were taken at specified time points, mixed with equal volume of loading buffer (50% glycerol, 1× assembly buffer) using the same rapid pipetting mentioned earlier, and placed on dry ice to preserve the current stage of re-association. Samples were loaded in reverse order onto 8% native-PAGE at 4° C. Results were visualized with a ChemiDoc MP System with a Cy5 filter. The bands were quantified to determine the re-association kinetics using ChemiDoc software. All experiments were repeated at least three times and presented as the mean+/−SD.

Nanoparticle Degradation Assays.

Assembled nanoparticles containing either RNA or DNA strands labeled with Alexa 488 at 3'-side were used in chemical stability stadies. For RNase digestion assays, RNase $I_f$ (New England Biolabs) that cleaves at all RNA dinucleotide bonds leaving a 5' hydroxyl and 2',3' cyclic monophosphate, was used according to the manufactures protocols. For DNase digestion assays, RQ1 RNase-free DNase (Promega) that cleaves both double-stranded and single-stranded DNA endonucleolytically, producing 3'-OH oligonucleotides, was used according to the manufactures protocols. For blood stability assays, freshly drawn human blood serum (blood was allowed to coagulate, then spun down and supernatant was collected) was immediately aliquoted and frozen at −80° C. Different nanocubes (1 μM final) were incubated with RNase, DNase, and 1% (v/v) human blood serum at 37° C. for 10 min. The reaction was stopped by snap cooling samples on dry ice prior to loading on native-PAGE. The bands were quantified to determine the re-association kinetics using ChemiDoc software. All experiments were repeated at least three times and presented as the mean+/−SD.

Primary Human Peripheral Blood Mononuclear Cell and Whole Blood Culture for Analysis of Interferon and Cytokine Secretion.

Blood from pre-screened healthy donor volunteers was collected under National Cancer Institute, Frederick Protocol OH99-C-N046 using BD vacutainer tubes containing Li-heparin as the anticoagulant. The blood was used within 1-1.5 h after collection and was kept at room temperature (RT). Whole blood was used for the analysis of chemokines and pro-inflammatory cytokines, while PBMC cultures, in which myeloid cells producing type I interferon are more concentrated than in whole blood, were used for the analysis of type I interferon. The Cultures were performed according to the standardized protocol NCL-ITA-10 (http://ncl.cancer.gov/NCL_Method_ITA-10.pdf). Supernatants were analyzed using a chemiluminescence based multiplex system (Quansys, Logan, Utah) according to the manufacturer's instructions. Two independent samples were prepared for each nanoparticle and tested in at least two individual donors. Each supernatant was analyzed in duplicate on multiplex plate. Presented is the mean+/−SD of individual samples (N=2) for each individual donor.

Computational Predictions and 3D Modeling.

Computational predictions of $T_m$s were performed for the different combinations of RNA and DNA strands using the HyperFold program. Predictions were performed at temperatures between 20° C. and 70° C. using steps of 2° C. intervals. For each temperature, the free energy corresponding to the ensemble of all nucleic acid structures for which all six strands are forming a complex was computed. Using linear interpolation, the temperature corresponding to a free energy of zero was determined. Additional structure predictions were performed at 10° C. in order to obtain the idealized secondary structures shown in FIG. 10.

The all-RNA cube model is identical to that which was built with the aid of our program called NanoTiler, (https://binkley2.ncifcrf.gov/users/bshapiro/software.html) and scaled to bring it into better agreement with the experimental data (1, 2). The RNA/DNA hybrid cubes and DNA cube models utilize the RNA cube as a spatial reference, but were created independently in PyMOL Molecular Graphics System (Schrödinger, LLC., http://www.pymol.org/) with custom scripts connecting B-form (pure DNA) and A-form (Hybrid and pure RNA) helices and single-stranded corner linker fragments pre-generated in Accelrys Discovery Studio Visualizer 4.0 (Accelrys Software, Inc; http://accelrys-.com). The DNA/RNA hybrid cube model shown in FIG. 1B that was built from 3 RNA and 3 DNA strands mixes the B-form and A-form helices in one cube (2 pure DNA B-form helices, 2 pure RNA A-form helices and 8 DNA/RNA helices). All preliminary models were structurally cleaned-up with implicit solvent Generalized Born energy minimization in Amber14 with the RNA and DNA specific components of the force field ff14SB (3-8). In addition, all models were subjected to 50 ns long explicit solvent molecular dynamics (TIP3P water model, Berendsen thermostat, PME method for long distance interactions and 9 Å non-bonded cutoff (9, 11) simulations that verified their robustness, i.e. maintenance of the designed base pairing under full cube dynamic distortions (results not shown).

Flourescence Studies

Activation of FRET: To determine the re-association of nanoparticles in vitro, FRET measurements were performed using a FluoroMax3 (Jobin-Yvon, Horiba). For all measurements, the excitation wavelength was set at 460 nm and the excitation and emission slit widths were set at 2 nm. For tracking the DS RNA formation, DS sense and antisense strands were modified with Alexa 488 and Alexa 546 fluorophores, respectively. To follow the kinetics of re-association, purified DNA nanoparticles containing DS sense strands were first incubated for two minutes at 37° C. and nanoparticles assembled with DS antisense strands were then added in equimolar amounts. At 460 nm excitation, the emissions were simultaneously recorded at 520 nm and 570 nm every 30 seconds to follow the DS RNA formation through FRET. This was completed for nanoparticles with and without Lipofectamine 2000 (L2K) added in the concentrations corresponding to the transfection experiments. For reporter DNA release in co-transcriptional production experiments, static measurements were performed after 3 hours of incubation of equimolar amounts of the two fluorescently labeled DNA nanoparticles. Since the reporter strands are relatively short (tP4C: 5'-ATAGTGAGTCG-Alexa 488; tP4AC:5'-Alexa 546-CgACTCACTAT) with $T_m$s below 37° C., FRET was measured at 20° C. Low $T_m$ can also explain the appearance of two bands, due to melting, on re-association gel in FIG. 2B.

Activation of Broc-Coli aptamers: Equimolar concentrations of purified cubes with Broc and anti-cubes with Coli RNA strands (both assembled at 1 µM final) were thoroughly combined and incubated at 37° C. for 30 minutes. Afterwards, samples were kept at RT for 10 minutes before being placed on ice. All assemblies and re-associations were confirmed by native-PAGE. The gels underwent three washes with ddiH$_2$O for durations of five minutes each. After the final wash, the gel was stained with (Z)-4-(3,5-difluoro-4-hydroxybenzylidene)-2-methyl-1-(2,2,2-trifluoroethyl)-1H-imidazol-5(4H)-one (DFHBI-1T) for 30 minutes and visualized with a Bio-Rad ChemiDoc MP System. Afterwards, the gel was stained with ethidium bromide and visualized with a Bio-Rad ChemiDoc MP System. To trace the re-associations of cubes in solution, equal amounts (1 µM final) of cubes with Broc and anti-cubes with Coli RNA strands were combined, mixed and incubated at 37° C.; 2 µL aliquots were taken at specified time points and fluorescence of DFHBI-1T was measured using NanoDrop 3300 Fluoropectometer. Re-association experiments were repeated at least three times and presented as the mean±SD.

AFM Imaging and Sample Preparation.

A freshly cleaved mica surface was treated with 1 mM solution of NiCl$_2$ before deposition of 5 µL of 1 µM RNA solution for 2 min. The unbound RNA molecules and excess of salts were washed twice with 50 µL of DI water and the mica surface was dried under a stream of nitrogen gas. AFM imaging was performed on AFM 5500 Keysight Technologies using alternating contact (AC) mode. The images were recorder with 2 Hz scanning rate using a silicon probe with resonance frequency of 287 KHz ans spring constant between 10-50 n/m. Images were processed by PicoVeiw 1.2 software and leveled by third-order fit for sample tilt correction. Triangle DNA samples were imaged in AFM facility at University of Nebraska Medical Center, according to the well-developed procedure (12).

Transfection of Human Cell Lines.

For cell culture experiments with nanoparticles, human breast cancer MDA-MB-231 (with or without eGFP), human prostate cancer PC-3, and human cervical cancer Hela cell lines were grown in D-MEM (MDA-MB-231 and Hela) and RPMI (PC-3) media at 37° C. in a 5% CO$_2$ incubator. The media was supplemented with 10% FBS and penicillin-streptomycin. All transfection experiments were carried out using L2K purchased from Invitrogen. Solution of purified nanoparticles (100× concentration) were pre-incubated at RT with L2K. Prior to each transfection, the cell media was changed to OPTI-MEM (from RPMI or D-MEM) and prepared nanoparticles with L2K complexes were added to the final 1× concentration. The cells were incubated for 4 hours followed by a media change (RPMI or D-MEM).

Fluorescent Microscopy.

To assess the intracellular interaction and shape of nanoparticles, FRET measurements were performed using a LSM 710 confocal microscope (Carl Zeiss) with a 63×, 1.4 NA magnification lens. PC-3 cells were plated in glass bottom petri dishes (Ibidi) and transfected with fluorescently labeled complementary cubes and anti-cubes used in FRET studies. On the next day, the samples were fixed in 4% paraformaldehyde at RT. Images of the cells were then taken to assess the appearance of FRET within the sample as detailed elsewhere (13).

Flow Cytometry.

For intracellular activation of aptamers, HeLa human breast cancer cells were cultured at $2\times10^4$ or $3\times10^4$ cells per well respectively in either 12 or 24 well plates. XX hours post-transfections, cells were incubated with 5 µM DFHBI-1T for XX hours and then treated with cell dissociation buffer (Gibco). Fluorescence of DFHBI-1T was assessed using BD Accuri C6 flow cytometer. Non-transfected cells treated with DFHBI-1T were used as control. At least 15,000 events were collected for each sample and analysed. For specific gene silencing experiments, human breast cancer cells expressing GFP (MDA-MB-231/GFP) were cultured at 2×104 or 3×104 cells per well respectively in either 12 or 24 well plates. 72 hours post-transfections, cells were removed from plates using trypsin, centrifuged, and re-suspended in 1×PBS. Silencing of GFP was assessed using BD Accuri C6 flow cytometer. Non treated cells were used as control. At least 15,000 events were collected for each sample and analyzed. CellQuest or the CFlow Sampler software were used to retrieve the geometric mean fluorescence intensity (gMFI) and the standard error of the mean.

Cell Proliferation Assay.

The viability of cells after transfection with purified cognate nanoparticles designed to release DS RNAs against PLK1 and BCL-2 was assessed through the CellTiter 96® Aqueous One assay (Promega, Madison) following manufacturer's protocol. Briefly, upon addition of the CellTiter reagents to the cells in DMEM, the absorbance (490 nm) of the resorufin-forming compound was measured after three hours of incubation at 37° C.

Nuclease Digestion Assays.

Different Alexa 488 labeled nanocubes (1 µM final) were incubated with RNAse, DNase and human blood serum at 37° C. for 10 mins. The reaction was stopped by snap cooling samples on dry ice prior to loading on native-PAGE and further analysis.

Results

Complementary Nanoparticles have Controlled Rates of Re-Association and Fine-Tunable Thermodynamic, Chemical, and Immunogenic Properties.

Figure 7:
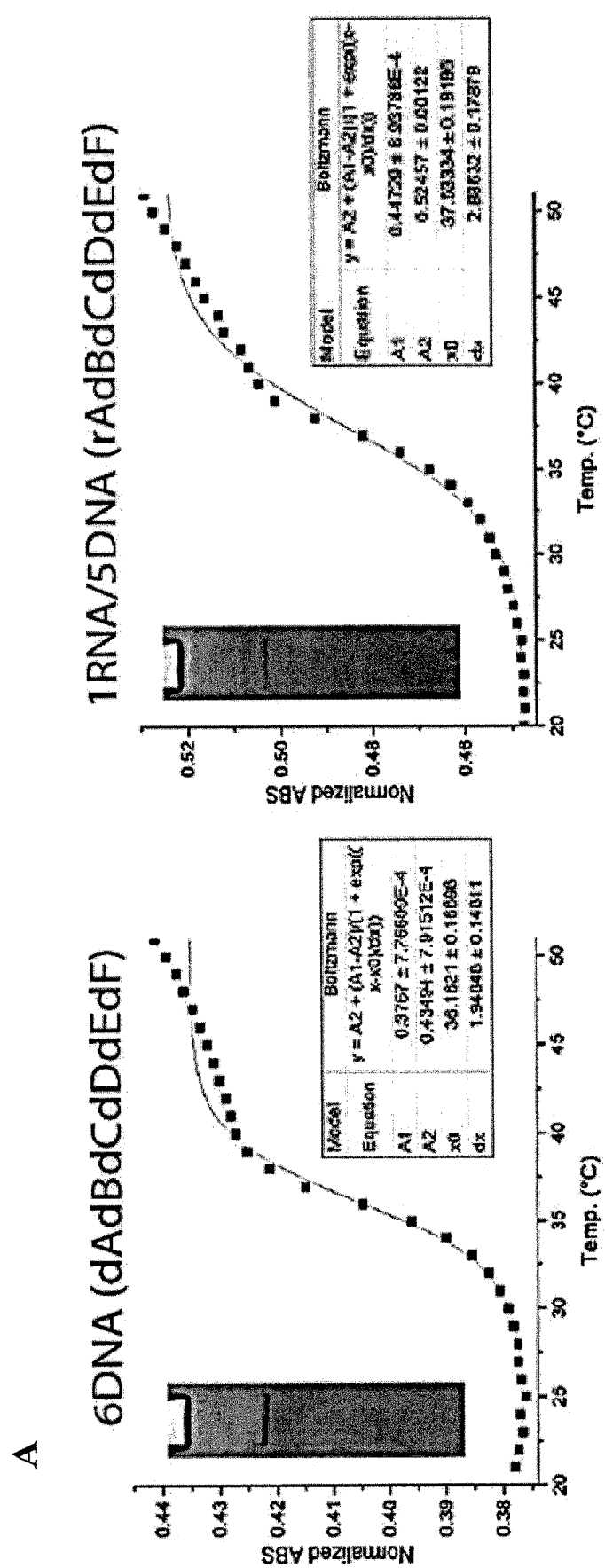
FIG. 7 shows melting temperatures measured by UV-melt for different compositions of cube nanoparticles (Normalized ABS versus Temperature (° C.)) (A) Shows a melting temperature plot for a 6DNA configuration and a 1RNA/5DNA configuration. (B) Shows a melting temperature plot for a 2RNA/4DNA configuration and a 3RNA/3DNA configuration. (C) Shows a melting temperature plot for a 4RNA/2DNA configuration and a 5RNA/1DNA configuration. (D) Shows a melting temperature plot for a 6RNA configuration and a 6 DNA anti-cube configuration. (E) Shows the melting temperatures (Tm (° C.)) for each of the cube configurations. EtBr total staining native-PAGE show the assemblies of corresponding compositions. Error is presented as s.d.; N=3.
Figure 7:
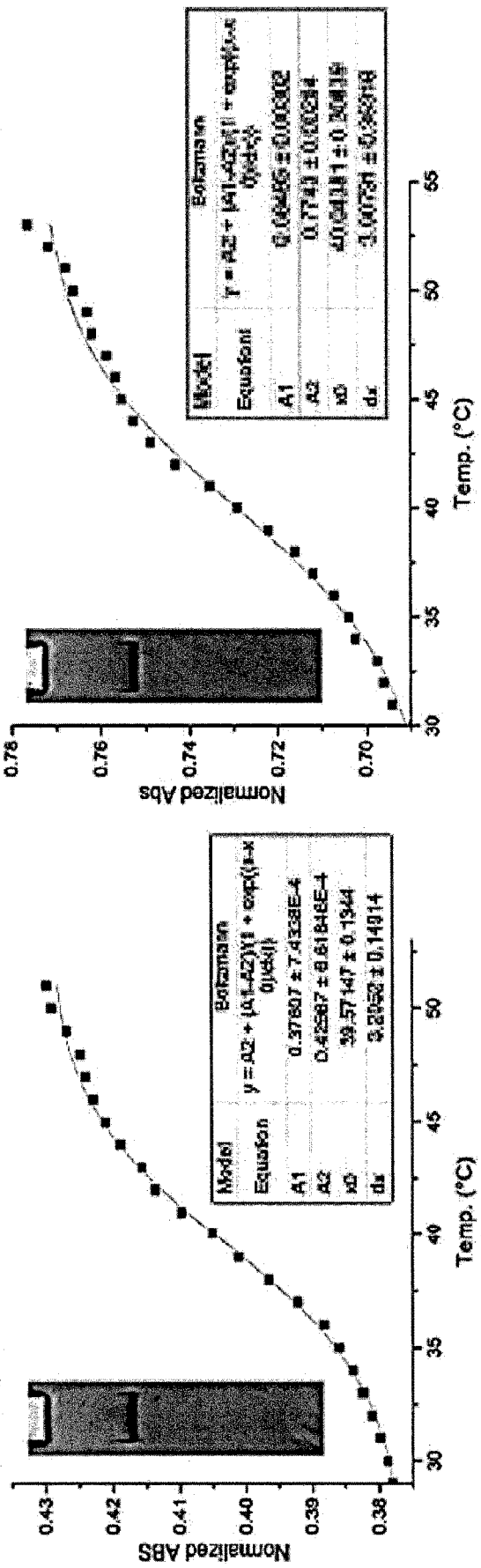
Figure 7:
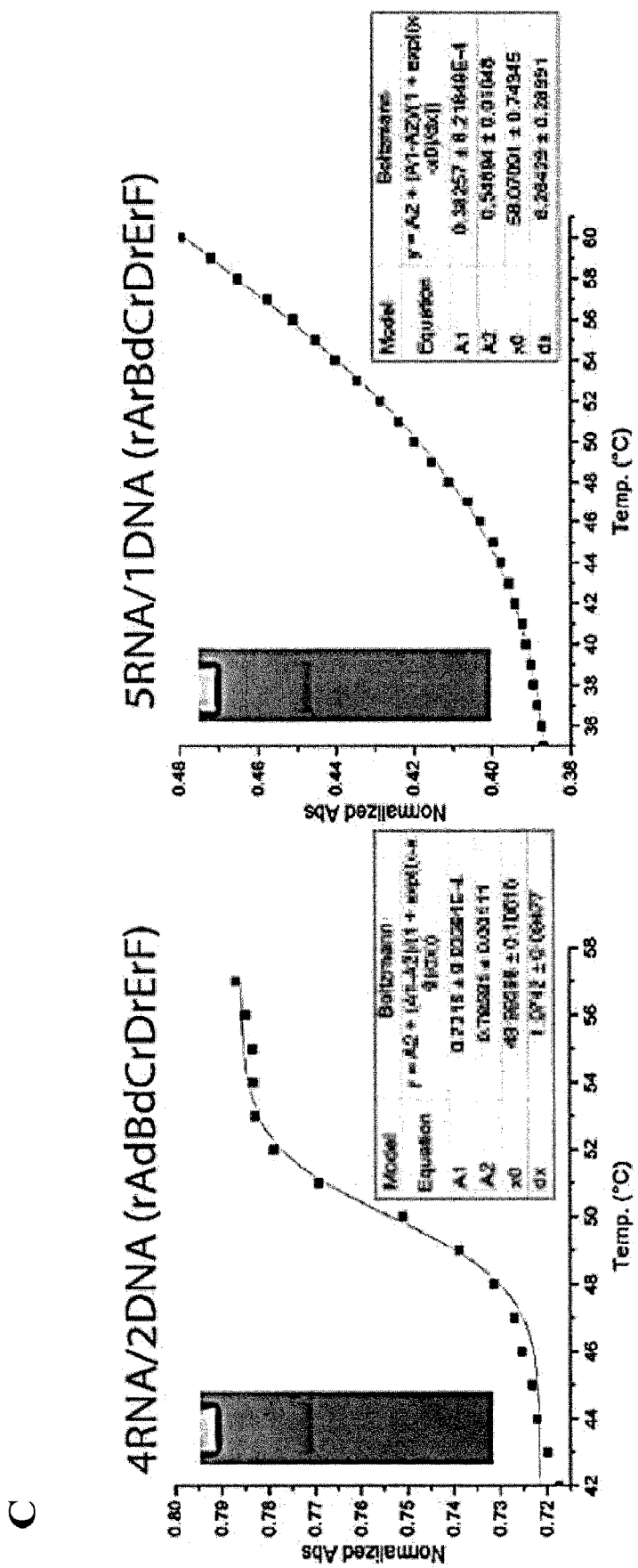
Figure 7:
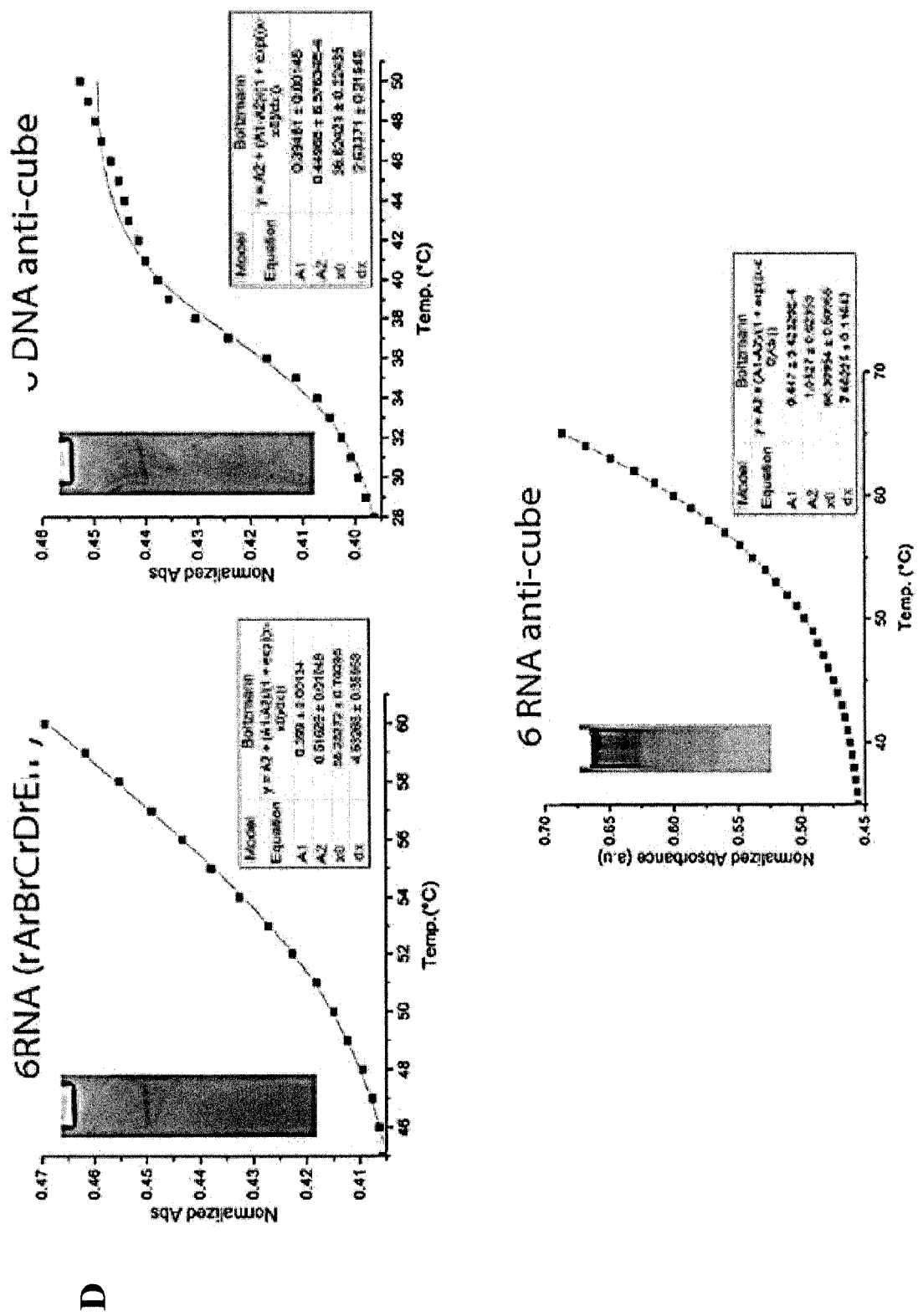
Figure 8:
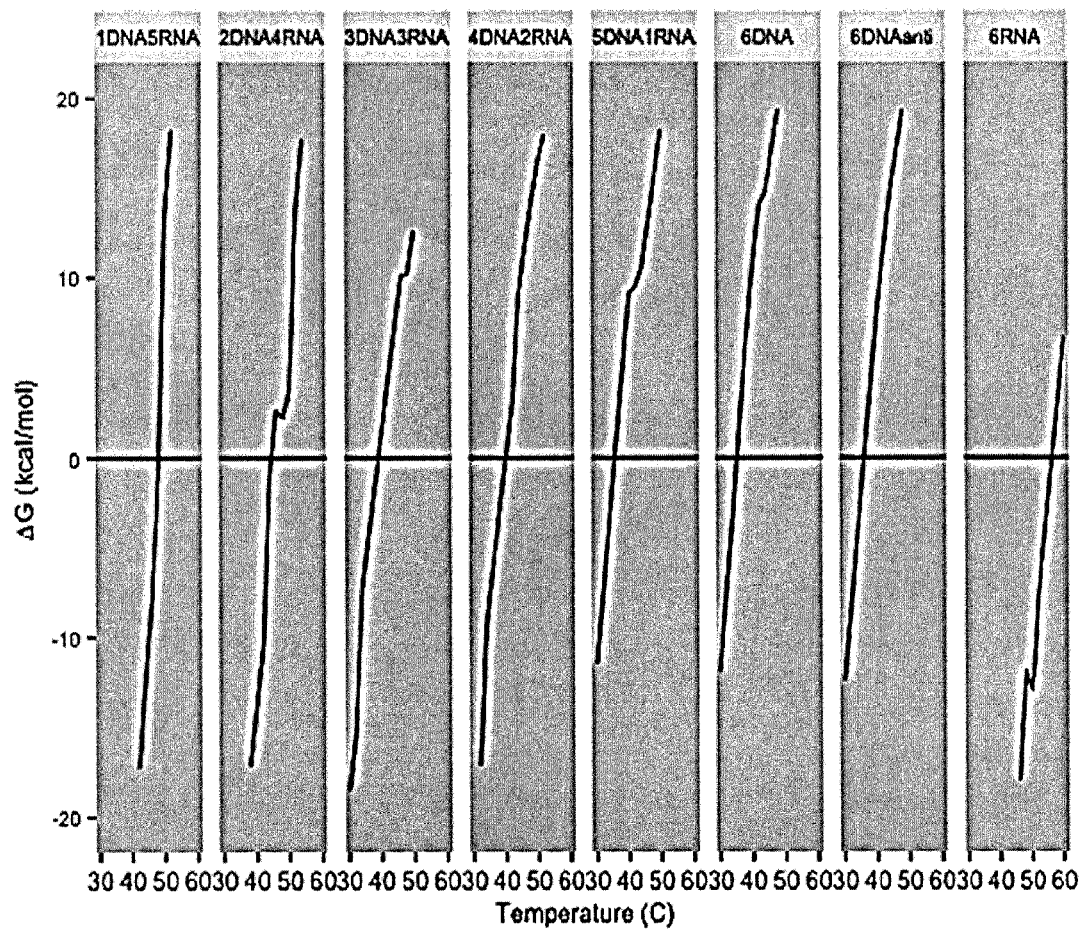
FIG. 8 shows the predicted free energy of nucleic acid cube structures (at 250 nM concentration) as a function of temperature for each of the indicated configurations of nanoparticles having different ratios of DNA and RNA strands.

An important feature of rationally designed cubes is their ability to efficiently assemble with different ratios of RNA and DNA strands entering their composition (FIG. 1B). This design flexibility together with the difference in physico-chemical properties between RNA and DNA allows to fine-tune the thermodynamic, kinetic, and chemical properties of the interacting nanoparticles (FIG. 1C-E). To prove the concept, seven cubes with different ratios of RNA and DNA strands in their compositions are examined. It is worth mentioning that the costs of tested nanoparticles increase by approximately a factor of two with the introduction of each RNA strand into the assembly. The assembly of all cubes were confirmed by non-denaturing polyacrylamide gel electrophoresis (native-PAGE). As expected, the relative thermodynamic stability of nanoparticles increased with the higher number of RNA strands introduced into the assembly, with the melting temperatures ($T_m$) ranging from ~36° C. for DNA cubes and anti-cubes to ~60° C. for RNA cubes. Computational predictions using the new version of Hyperfold (30) confirmed the experimental results (FIG. 1, FIG. 6 and FIG. 7).

Upon re-association of two complementary nanoparticles, the formation of duplexes consisting of cube and anti-cube strands was observed (FIG. 1). The re-association of the equimolar concentrations of the cognate cubes after 30 mins of incubation was demonstrated via native-PAGE. The intact cubes had lower mobility compared to corresponding duplexes. The re-association of cognate cubes was thermodynamically driven and did not require any toehold interactions.

Thermodynamics of Re-Associating Cubes.

At 20° C., 250 nM, we obtain the following free energies of predicted structures for the following nucleic acid strand combinations:

| Structure | Free Energy (kcal/mol) |
|---|---|
| RNA cube | −125.01 |
| DNA cube | −41.04 |
| DNA anti-cube | −41 |
| RNA/DNAa duplexes | −305.67 |
| DNA/DNAa dupelxes | −318.61 |

For the re-association of RNA cube and DNA anti-cube we obtain:

$$\Delta\Delta G = \Delta G_{RNA/DNA\alpha} - \Delta G_{RNA} - \Delta G_{DNA\alpha}$$

$$\Delta\Delta G = -305.67 \text{ kcal/mol} - (-125.01)\text{kcal/mol} - (-41) \text{ kcal/mol} = -139.67 \text{ kcal/mol}$$

In contrast, for the re-association of the DNA cube with the DNA anti-cube we obtain:

$$\Delta G = \Delta G_{DNA/DNA\alpha} - \Delta G_{DNA} - \Delta G_{DNA\alpha}$$

$$\Delta\Delta G = -318.61 \text{ kcal/mol} - (-41.04)\text{kcal/mol} - (-41) \text{ kcal/mol} = -236.57 \text{ kcal/mol}$$

There appears to be a big energetic difference: while the RNA/DNA hybrid duplexes are similar in energy compared to DNA/DNA duplexes, it is the RNA cube that is energetically far more stable compared to the DNA cube and less apt to participate in the re-association reaction.

Another role may play, that the DNA cube is more likely to be partially unfolded compared to the RNA cube, thus providing additional toehold-like regions that may aid the re-association. However, the kinetics of re-association were tracked experimentally at 25° C., which is below the $T_m$ of DNA cubes (FIG. 7).

Both of these effects are contributing to the experimentally observed tendency, that the DNA cube combined with the DNA anti-cube are re-associating far more readily compared to the RNA cube combined with the DNA anti-cube.

Figure 9:
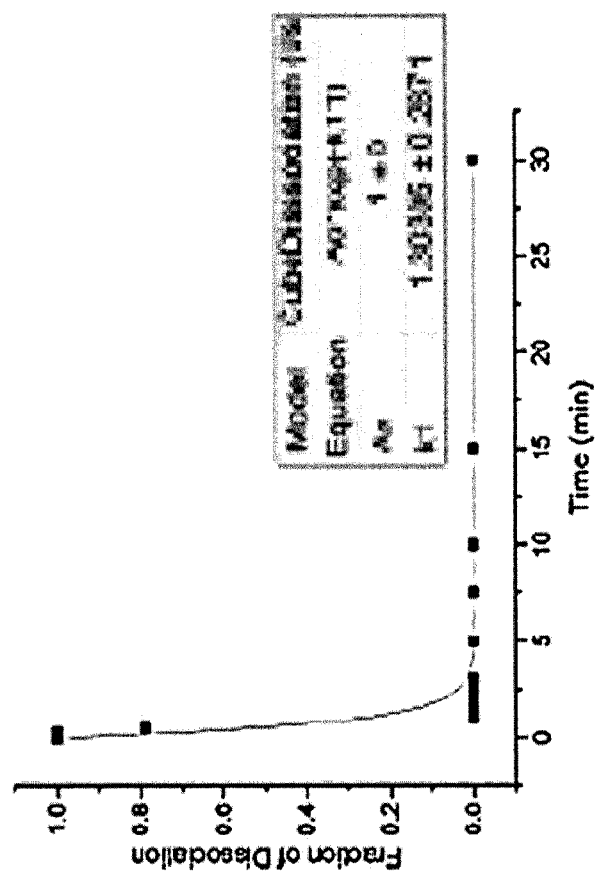
FIG. 9 provides relative rates of re-association measured for different composition of nanoparticles using native-PAGE. The configurations include (A) 6DNA, (B) 2RNA/4DNA, (C) 4RNA/2DNA, (D) 6RNA, (E) 1RNA/5DNA, (F) 3RNA/3DNA, and (G) 5RNA/1DNA. In all experiments gel purified anti-cube was fluorescently labeled with Cy5. (H) compares the re-association rates for each configuration. Error is presented as s.d.; N=3.
Figure 9:
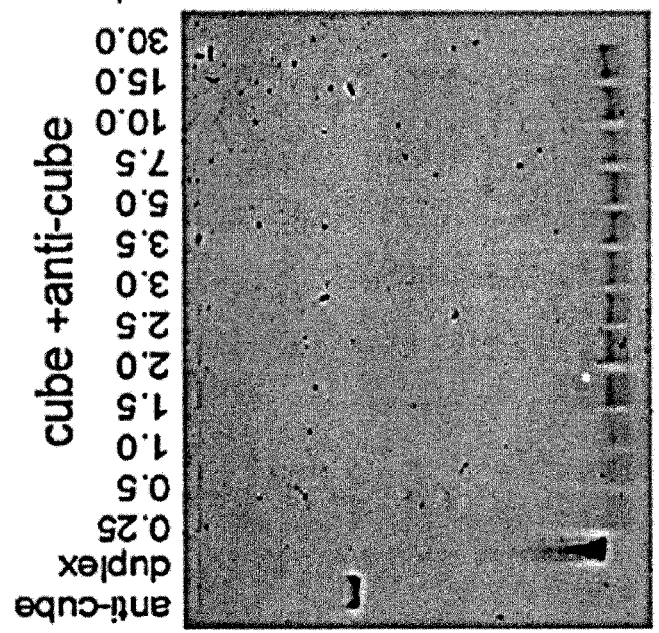
Figure 9:
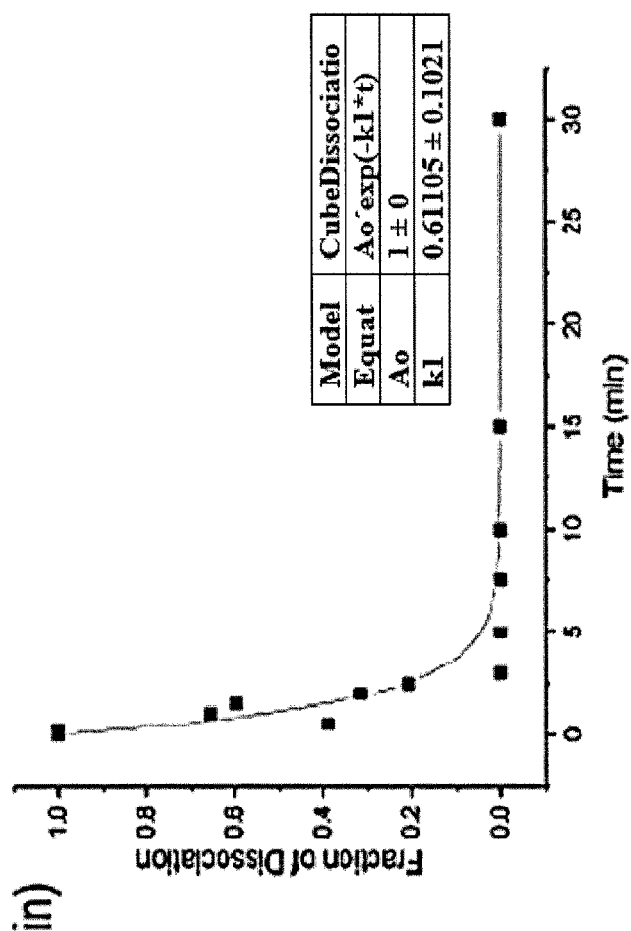
Figure 9:
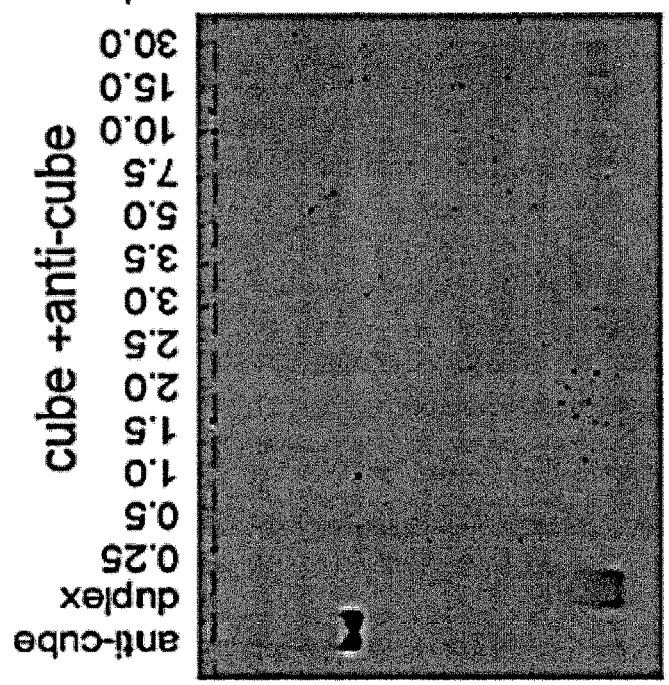
Figure 9:
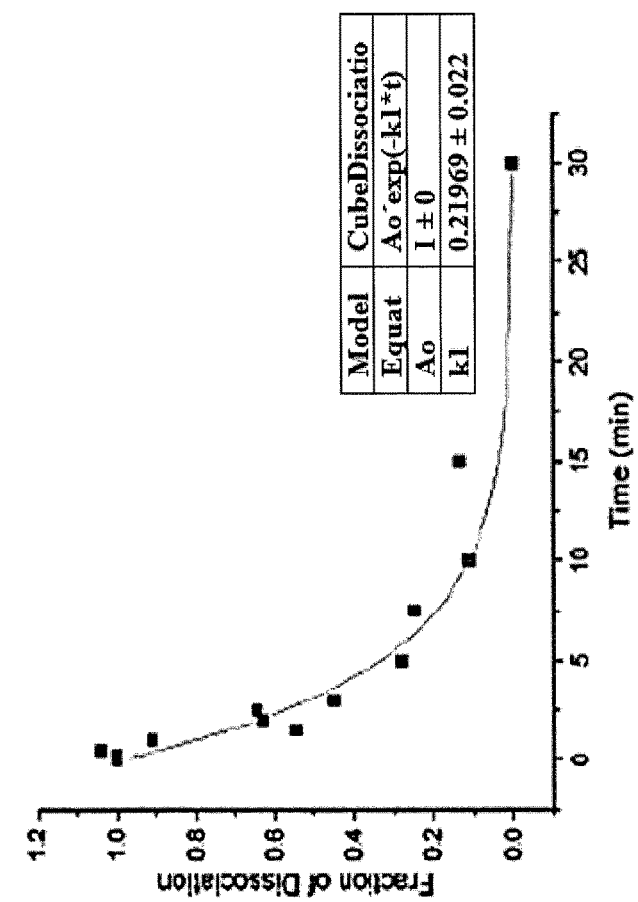
Figure 9:
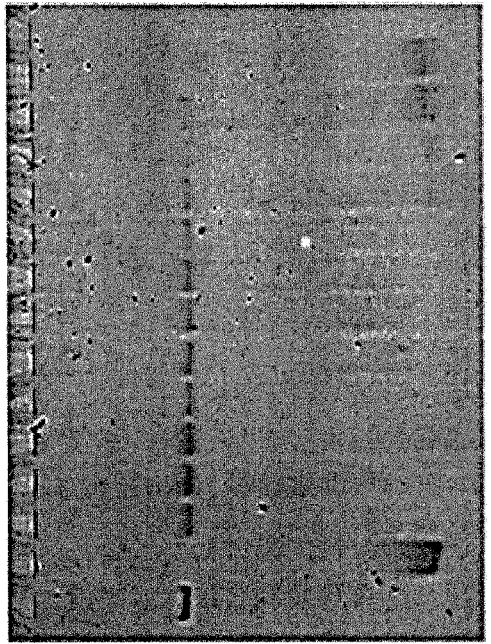
Figure 9:
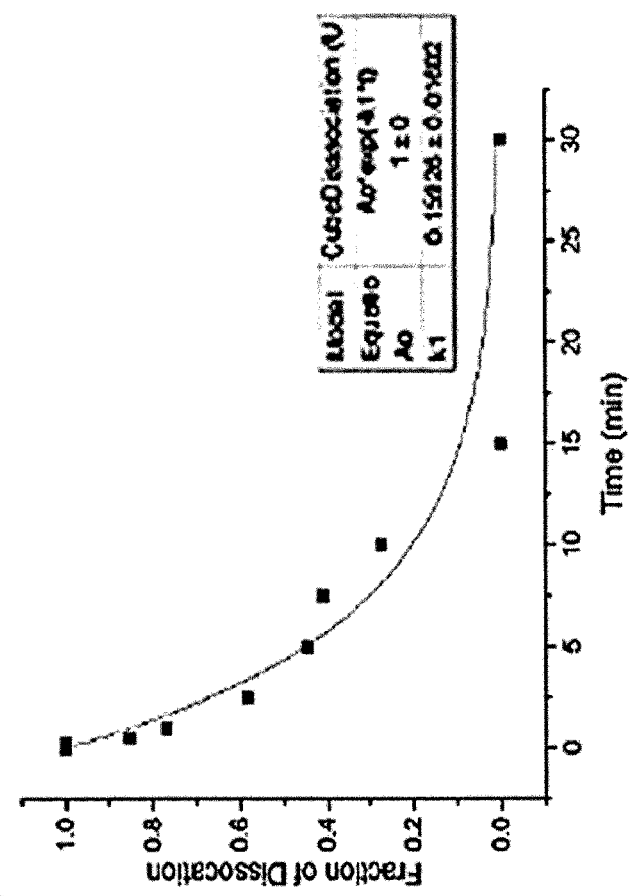
Figure 9:
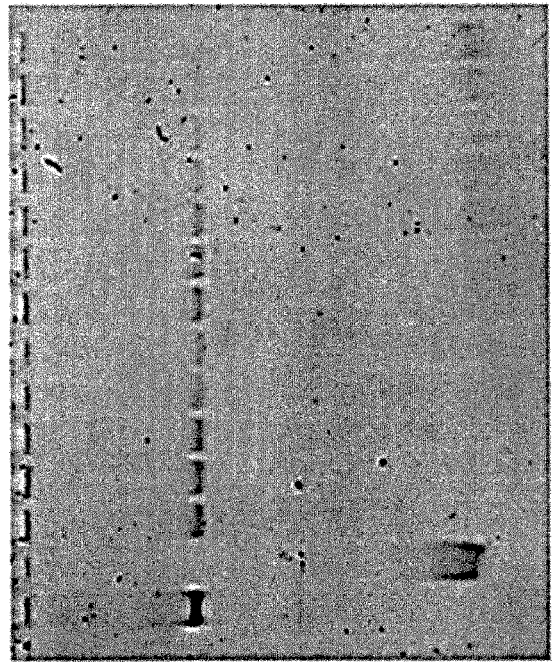
Figure 9:
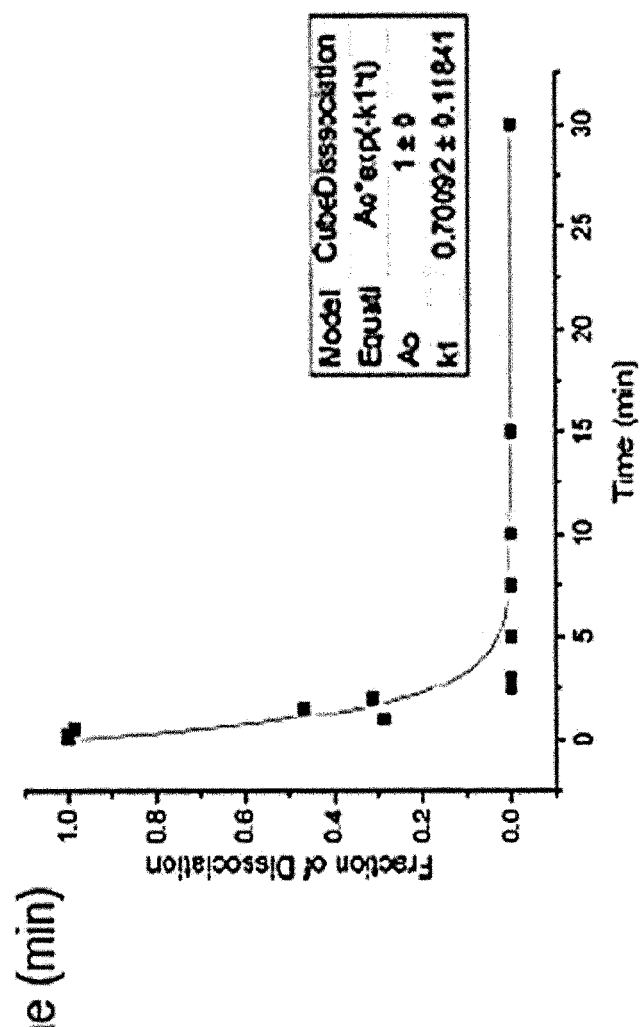
Figure 9:
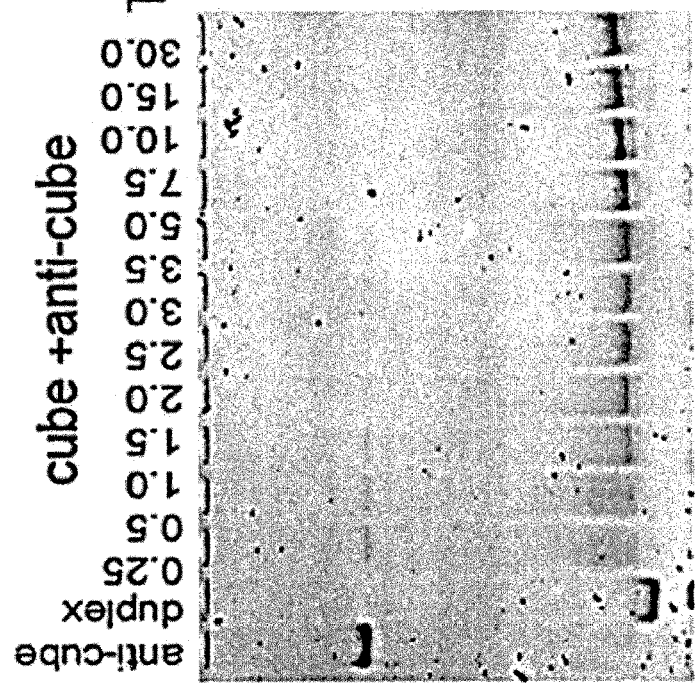
Figure 9:
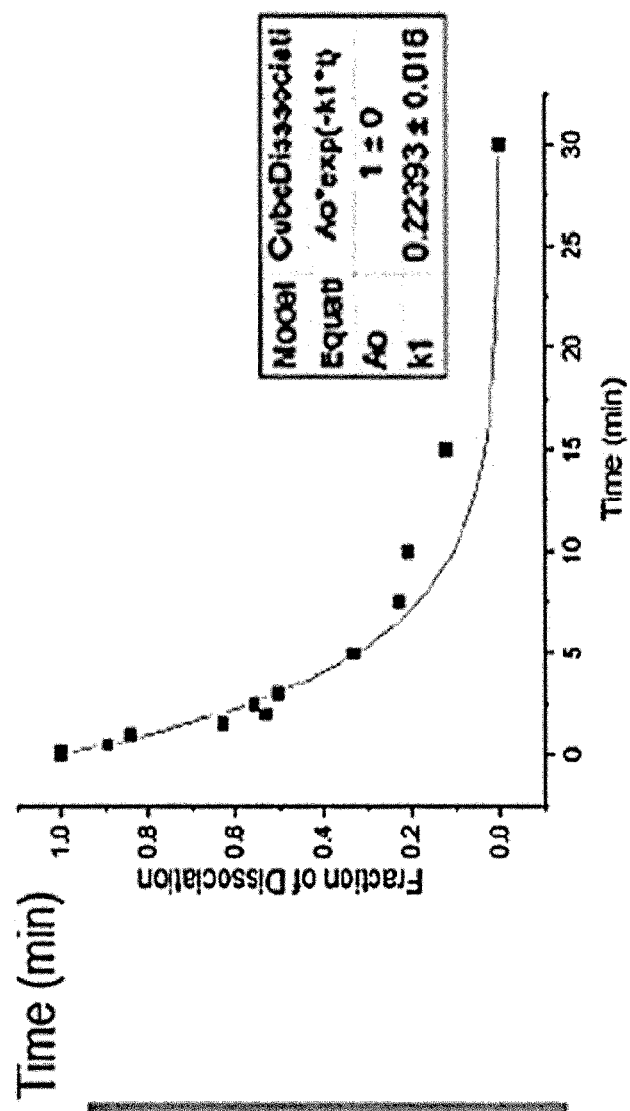
Figure 9:
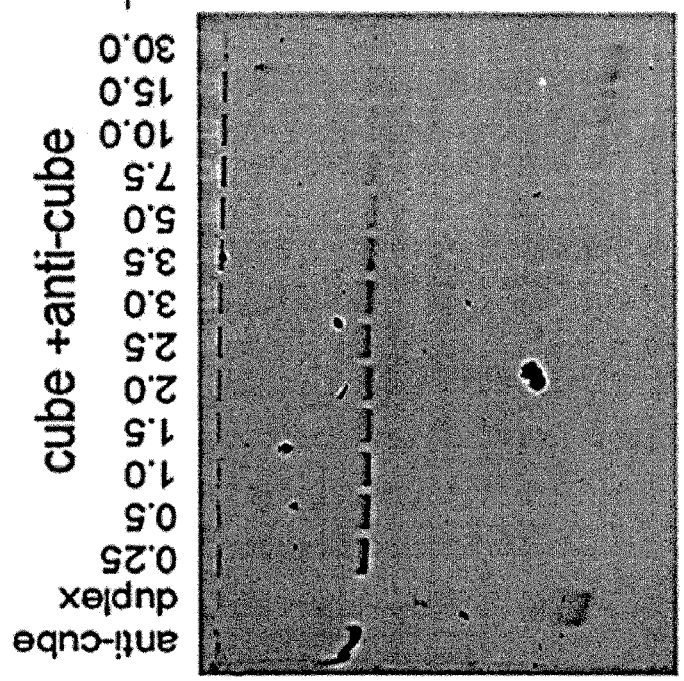
Figure 9:
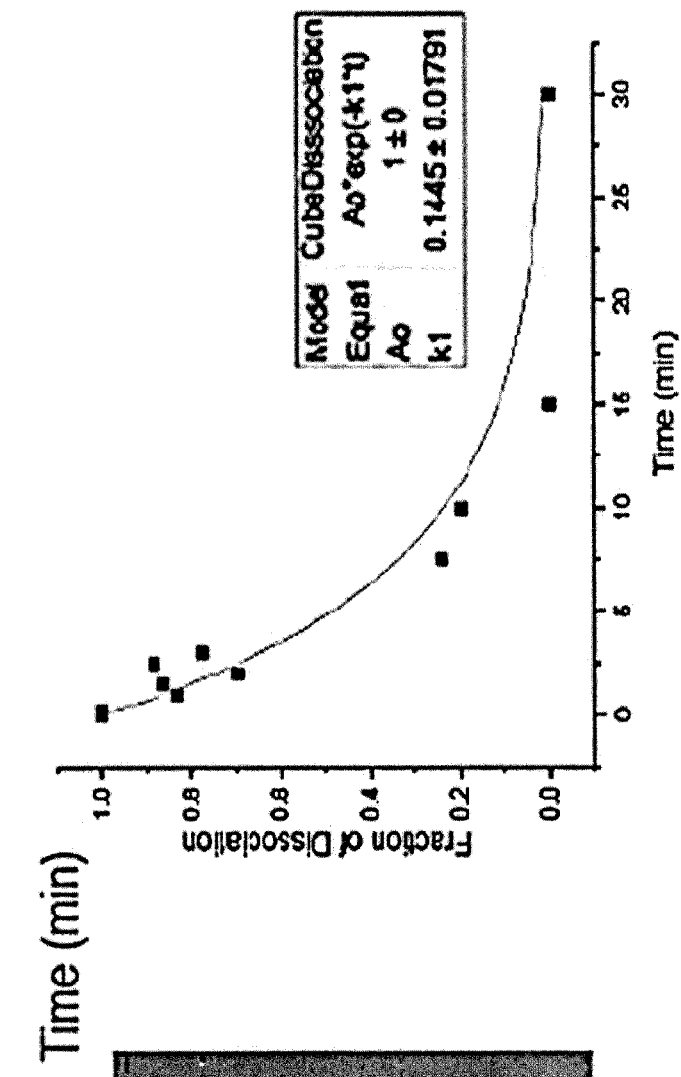
Figure 9:
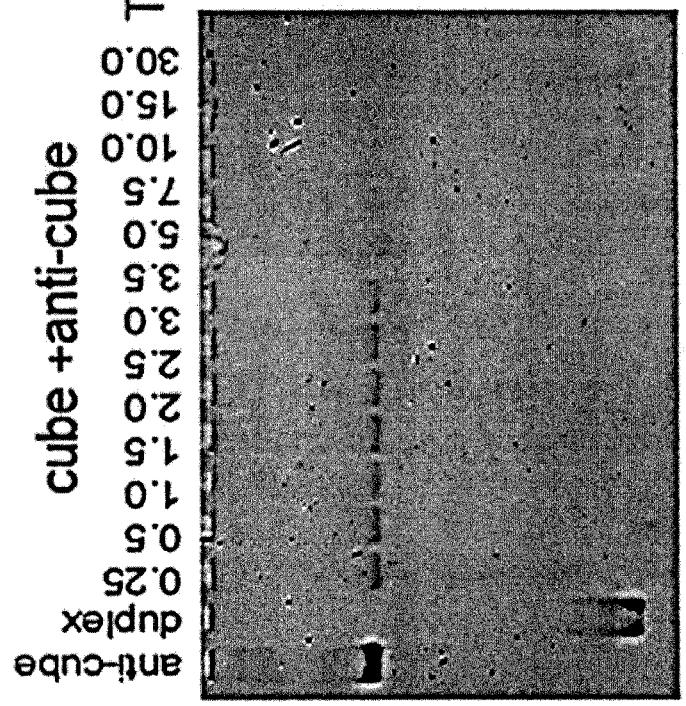
Figure 9:
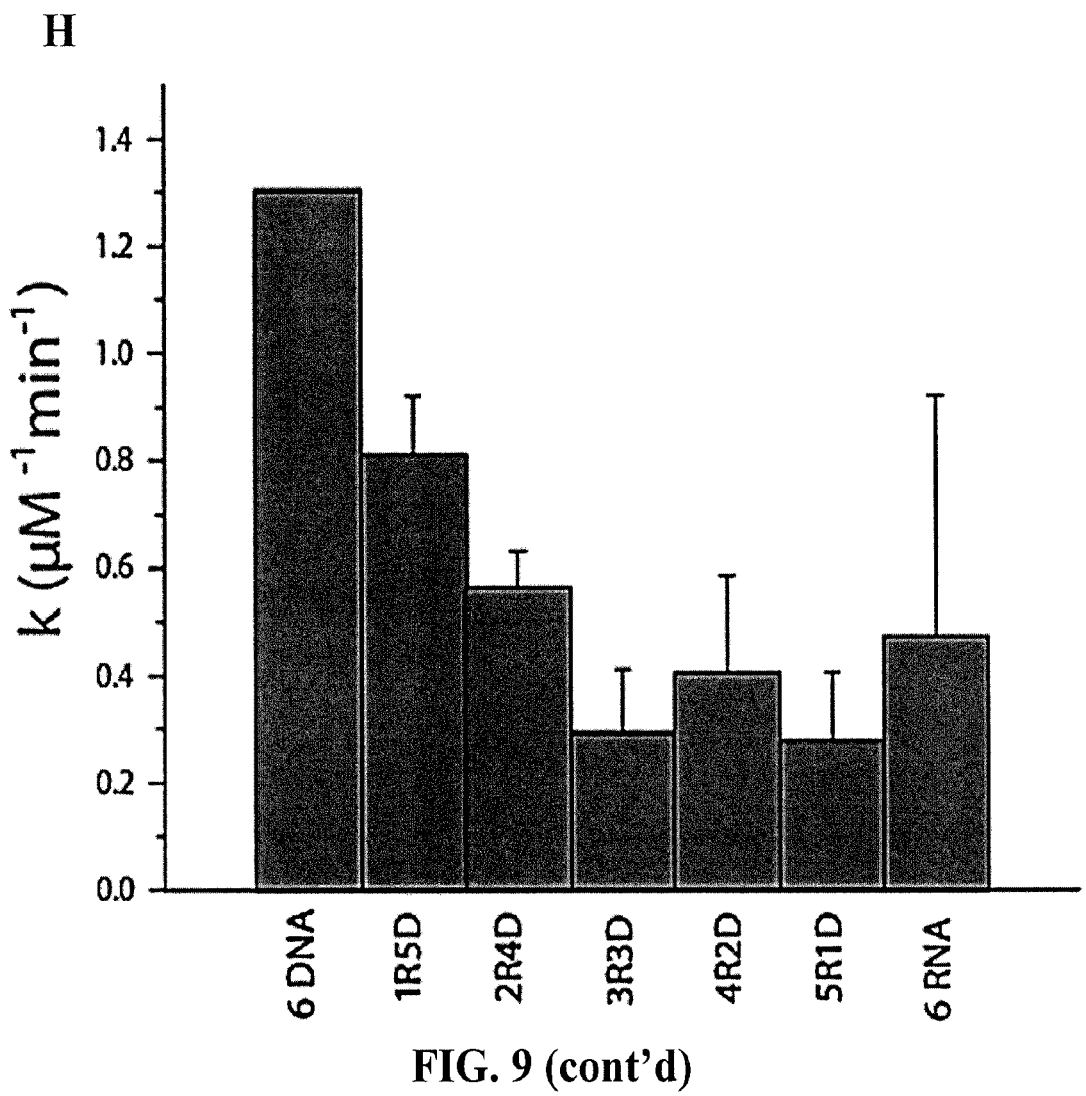
Figure 10:
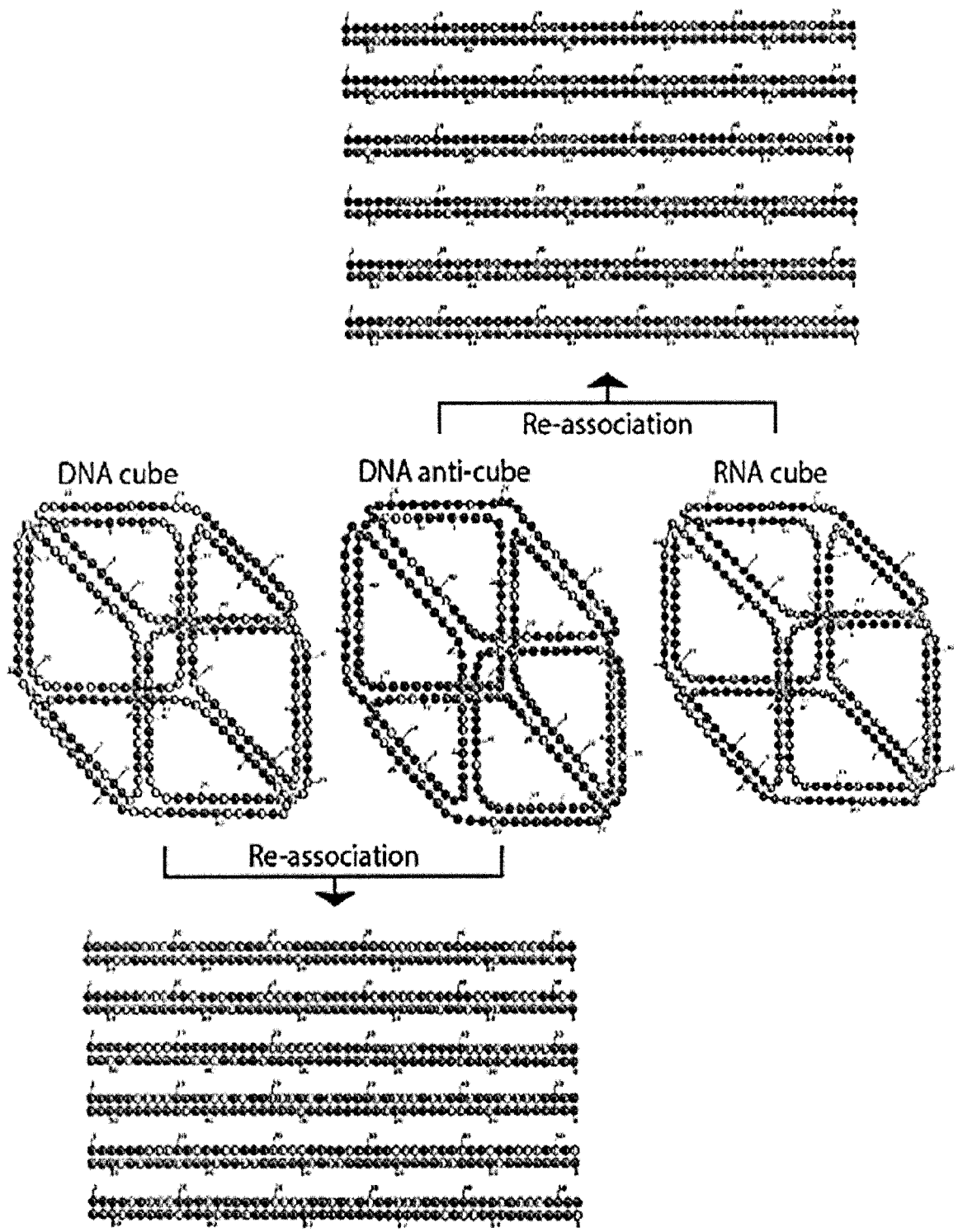
FIG. 10 shows computationally predicted secondary structures of RNA cube (right, middle), DNA anti-cube (middle) and hybrid duplexes (top and bottom duplexes) formed during their re-association. As described in the Methods section, secondary structure predictions where generated using HyperFold for a variety of different temperatures and different combinations of RNA and DNA strands. The depicted secondary structures are idealized secondary structures, but they are also identical to the secondary structures for low temperatures (10° C.). At higher temperatures, the predicted cube structures are similar, but some helices (especially helices consisting of only 4 or 6 base pairs) are predicted to be unfolded. This tendency is more pronounced for DNA strands compared to RNA strands.

As described in the Methods herein, secondary structure predictions for different cubes and the products of their re-association can now be automatically generated using HyperFold (FIG. 10). The kinetics experiments (FIG. 9) demonstrated the capability to directly alter the rates of re-association by changes in the nucleic acid makeup. The higher number of RNA strands in cube composition delayed the re-association. This notion was supported by the measured $T_m$s. The relative chemical stability and the resistance to nuclease degradation can also be tuned by changing the composition of cube (FIG. 1).

Although synthetic RNA and DNA nanoparticles are biodegradable and commonly considered highly biocompatible, various therapeutic RNA and DNA motifs have been found to trigger the human innate immune system, leading to the induction of pro-inflammatory cytokines and type I interferons thus, complicating the translation of these novel therapeutics from bench to clinic (39). The immune response to the cubes with varying ratio of RNA to DNA strands was analyzed in primary human peripheral blood mononuclear cell cultures by measuring the activation and secretion of type I interferon (IFN-α) as well as various pro-inflammatory cytokines and chemokines including IL-1β, TNFα, IL-8 and MIP-1α (FIG. 1). IFNα, IL-1β and TNFα were selected because they are common biomarkers used to estimate the pro-inflammatory potential of nucleic acids during both normal immune responses to viral pathogens and during autoimmune responses to the host nucleic acids (40, 41). The same markers were used in (pre)clinical studies to estimate the safety of RNA therapeutics (42). We expanded this commonly used test panel by adding pro-inflammatory chemokines IL-8 and MIP-1α (43). To deliver nanoparticles to cells, we complexed them with Lipofectamine 2000. Such complexation was used for consistency with other experiments presented in this study, and because expression of the immune receptors sensing nucleic acids is restricted to the intracellular compartments (e.g., endosomes, cytosol). Although all tested constructs induced the expression of IFNα, IL-8 and MIP-1α, cubes containing six RNA strands were more potent immune stimulants compared to other tested particles. A similar trend was observed in the cases of pro-inflammatory cytokines IL-1β and TNFα, which were induced only by cubes containing five or six RNA strands. The levels of chemokines IL-8 and MIP-1α were raised proportionally with increasing number of RNA strands, except for 2DNA/4RNA cube, which was as potent as cubes containing higher number of RNA strands. This data suggested greater immunostimulatory potential of RNA cubes and is consistent with the earlier reports (35). This finding also demonstrated that the reduction in number of RNA strands is a viable strategy for reducing any undesirable immunostimulation of these nanoparticles if they are used for systemic delivery. It further suggested that optimizing the ratio between RNA and DNA strands can be used to create nanoparticles with optimal immunomodulatory properties when activation of the immune system is desirable (e.g. vaccines and immunotherapy). The precise mechanism of the immune recognition of the particles reported herein is a subject for a separate mechanistic study.

Re-Association of Complementary DNA Nanoparticles Triggers Co-Transcriptional Formation of RNA Nanoparticles.

Figure 2:
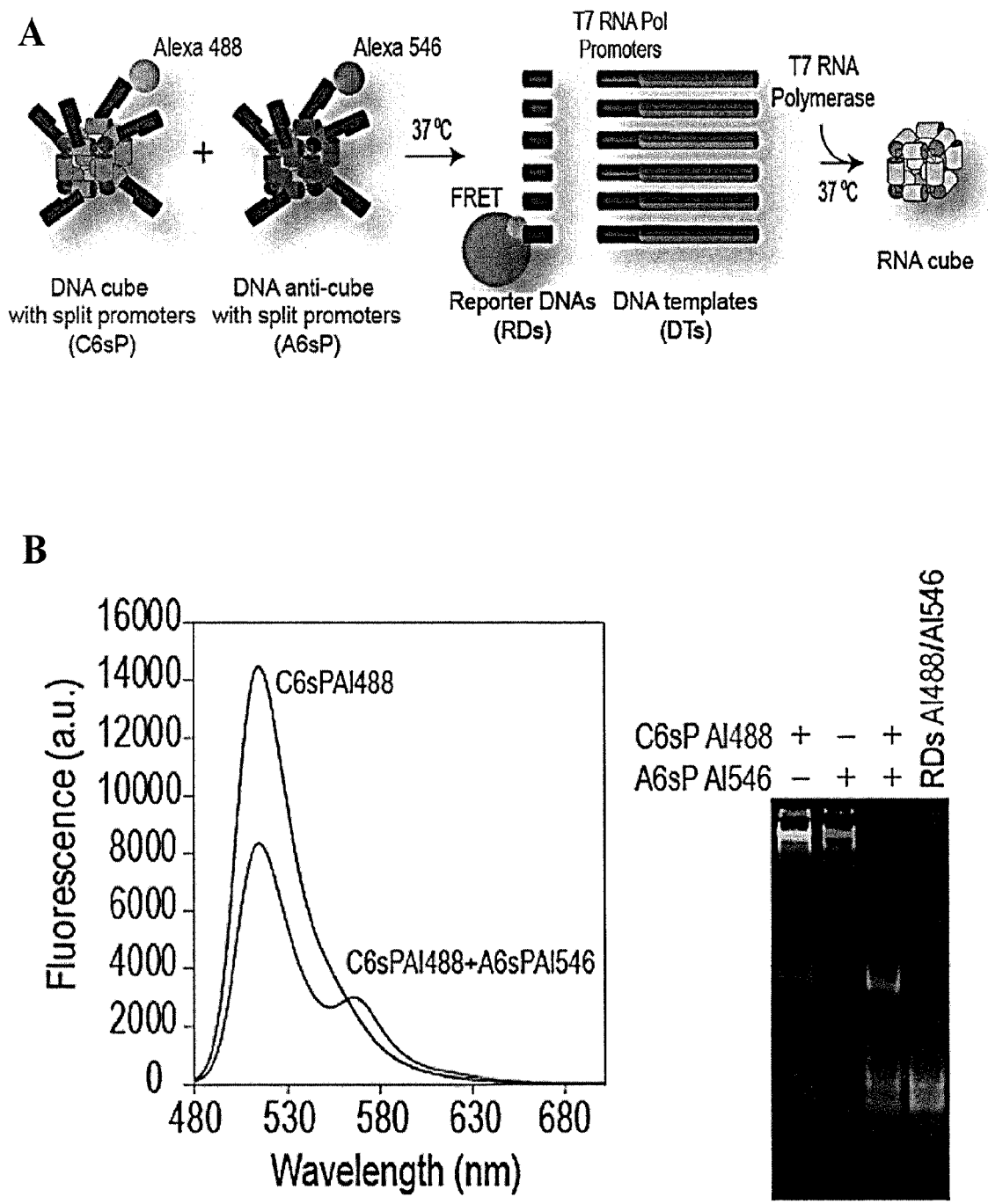
FIG. 2 shows Isothermal re-association of complementary DNA nanoparticles activates co-transcriptional production of RNA nanoparticles. (A) Schematics of isothermal re-association between the complementary cube and anti-cube nanoparticles carrying split T7 RNA polymerase promoters. The DNA cube and DNA anti-cubes are depicted as comprising functional arms (and anti-arms). In this embodiment, the functional arm comprises a single-strand extension of the DNA strands making up the cube body. This single-strand DNA extension comprises one of the two sequences making up the split T7 RNA polymerase promoter. The complementary promoter sequence is in the extension arm of the anti-cube. The functional arms also comprise a complementary pair of short-length reporter DNAs which form a functional optical reporter duplex as a result of the interacting cognate DNA nanoparticles. This embodiment is an example of cognate nanoparticles (i.e., cube and anti-cube) having at least two functionalities (DNA reporting duplex and the DNA transcription template, including the "split" promoter sequence). (B-C) Native-PAGE and fluorescent experiments visualizing re-association of shape-switching purified DNA cubes and anti-cubes resulting in formation of DNA templates with activated T7 RNA polymerase promoters and further co-transcriptional assembly of RNA cubes. (D) RNA cubes can only be formed co-transcriptionally using DNA anti-cubes decorated with six complete T7 RNA Polymerase promoters (A6P) and not from DNA cubes (C6P) that are decorated with six complete T7 RNA polymerase promoters. (E) Native-PAGE showing the co-transcriptional production of RNA cubes from DNA anti-cubes with six promoters. (F) Co-transcriptionally assembled RNA cubes eluted from native PAGe and imaged by AFM.
Figure 2:
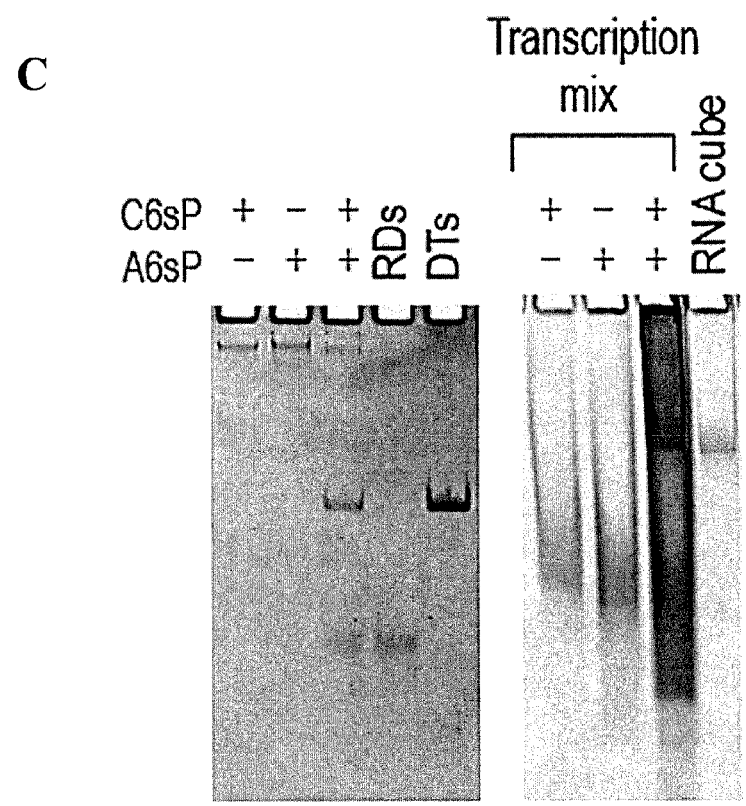
Figure 2:
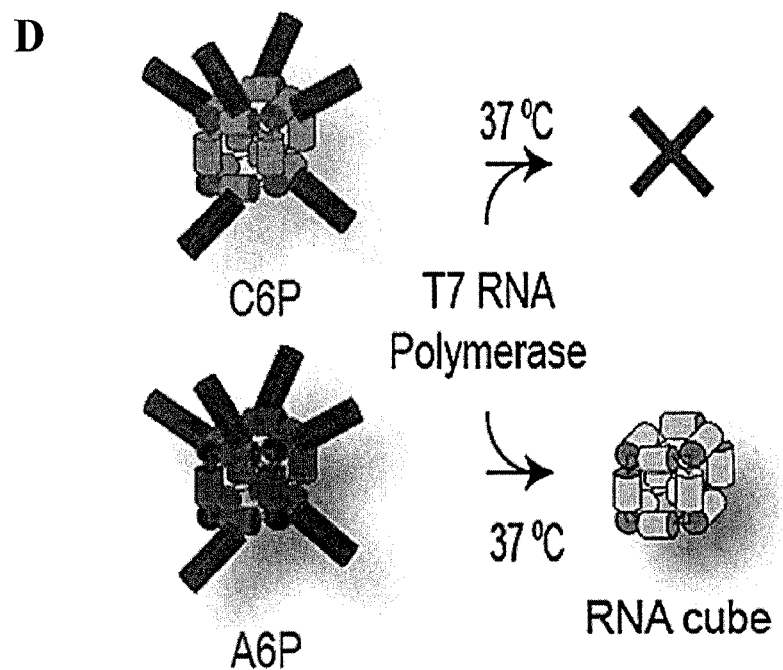
Figure 2:
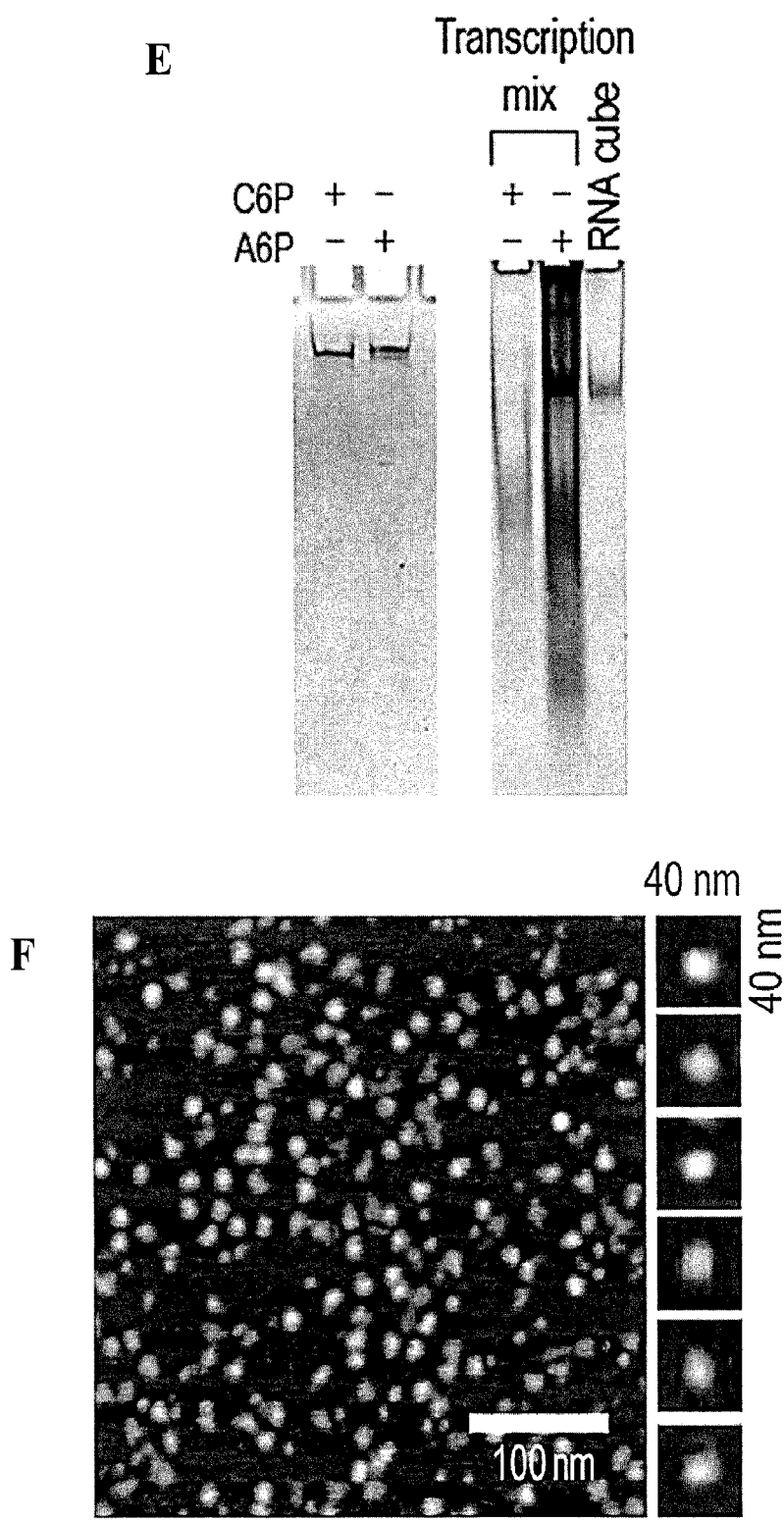
Figure 11:
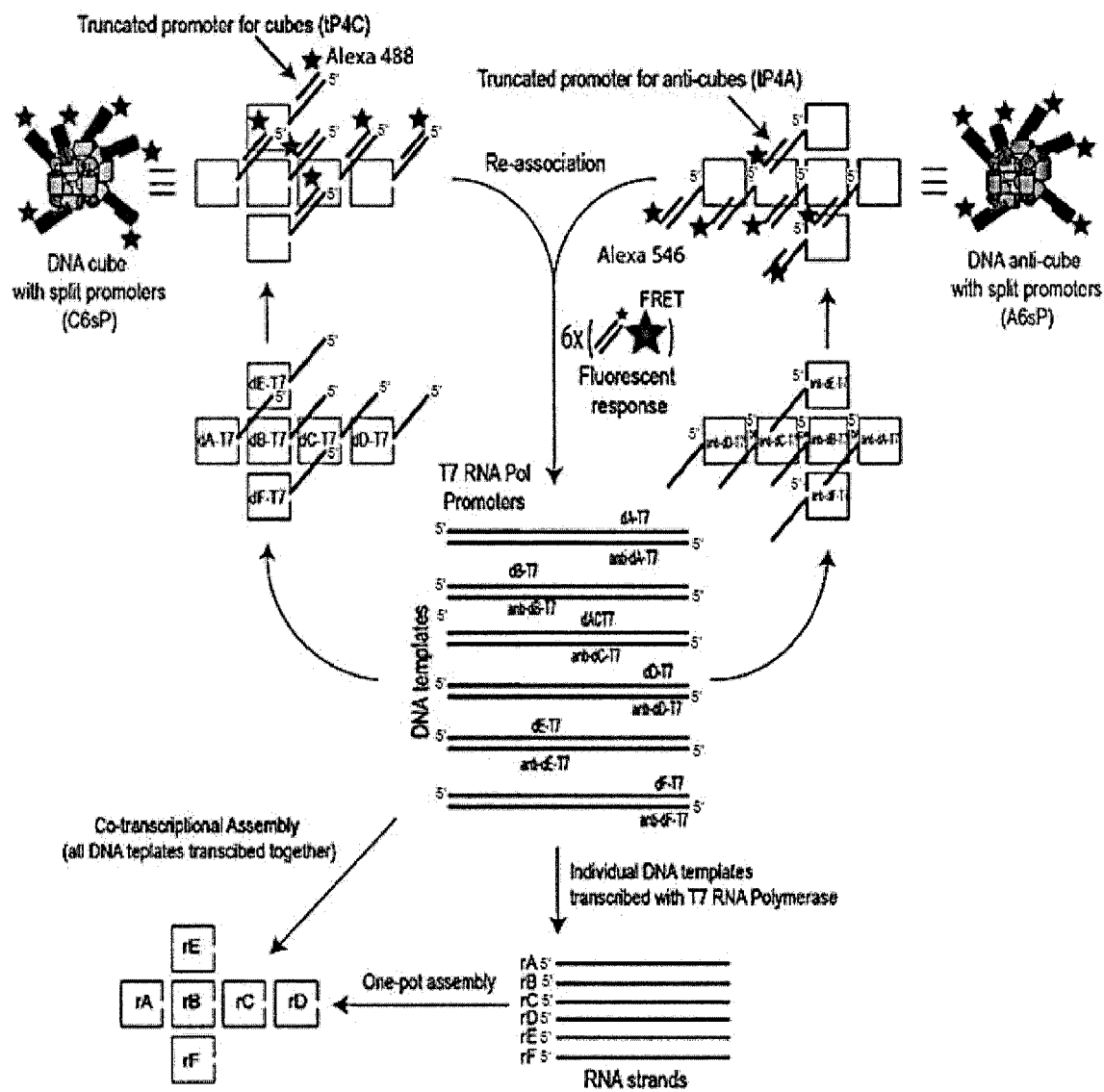
FIG. 11 is a schematic outlining the design principles of complementary nanoparticles activating the in vitro transcription on their re-association. The schematic depicts a DNA cube nanoparticle on the top left with split promoter (C6sP) arm extension and a short complementary RNA aptamer (e.g., optical sensor, such as FRET, for tracking RNA duplex formation). The schematic also depicts a DNA anti-cube nanoparticle on the top right with split promoter (A6sP) arm extension and a short complementary RNA aptamer. The aptamer strands may be complexed with Alexa 488 or Alexa 546 fluorophores for used in FRET monitoring of RNA duplex formation. The open configuration and the three-dimensional configurations are depicted at the top of the drawing. The DNA cube comprises individual strands A, B, C, D, E, and F, wherein each strand is joined to half of a T7 RNA polymerase promoter element. This element is then complexed with the short aptamer sequence. The DNA anti-cube comprises individual strands anti-A, anti-B, anti-C, anti-D, anti-E, and anti-F, wherein each strand is joined to half of a T7 RNA polymerase promoter element. This element is then complexed with the short aptamer sequence. The cube and anti-cube are then depicted to re-associate to form DNA template duplexes (each beginning with a re-associated T7 RNA polymerase promoter) and a coding region that when transcribed forms RNA strands A-F, which then may assemble to form an RNA cube. The RNA duplex comprising the aptamer sequences is not depicted in the drawing; however, the split aptamer sequences in each of the cube and the anti-cube would form an RNA duplex, thereby causing the Alexa 488 and Alexa 546 fluorophores to be activatable. Their detection signals the formation of the RNA duplexes, and by inference, the formation of the DNA duplex DNA templates.

The ability to activate the simultaneous transcription of multiple RNAs and further co-transcriptional assembly of RNA nanostructures is an important step towards the intracellular production of RNA nanoparticles. The endogenous production of functional RNA nanoparticles in mammalian cells will substantially increase their yields while eliminating the complexity of assembly protocols and reducing possible endotoxin contamination. In the attempt to control the transcription with complementary nanoparticles all six DNA strands of cube and anti-cube were modified with split T7 RNA polymerase promoters (FIG. 2A and FIG. 11). T7 RNA polymerase is a single-subunit enzyme that can be expressed in mammalian cells (44) and does not require any additional factors for accurate transcription. In the current design, the presence of both complementary DNA cubes in transcription mixture was required to undergo a shape switching and formation of dsDNA templates with active promoters whose further transcription leads to the assembly of RNA cubes. Short reporter DNAs were used to provide an optical response upon re-association (FIG. 2B). The co-transcriptionally assembled RNA cubes can be easily gel purified and used for further studies (FIG. 2C). Even though the co-transcriptional assembly of RNA cubes was efficiently triggered by the re-association of two parent DNA cubes, the run-off transcription of multiple individual DNA templates may not be ideal for co-transcriptional assembly of RNA nanoparticles in the intracellular environment due to potential degradation or compartmentalization of some DNAs causing stoichiometry problems with transcribed RNA units. To overcome this potential problem, the DNA anti-cube decorated with six complete T7 promoters (FIG. 2D) can be used. We then have an assembly of individually potent ssDNA templates (FIG. 12) required for the co-transcriptional production of RNA cube (FIG. 2E). The advantage of this approach is the precise control over the stoichiometry of the DNA templates and their local availability for transcription. These results paved the way for a further development of the intracellular co-transcriptional production of RNA nanoparticles.

Re-Association of Complementary DNA Nanoparticles Triggers Activation of Split RNA Aptamers in Cells.

Figure 3:
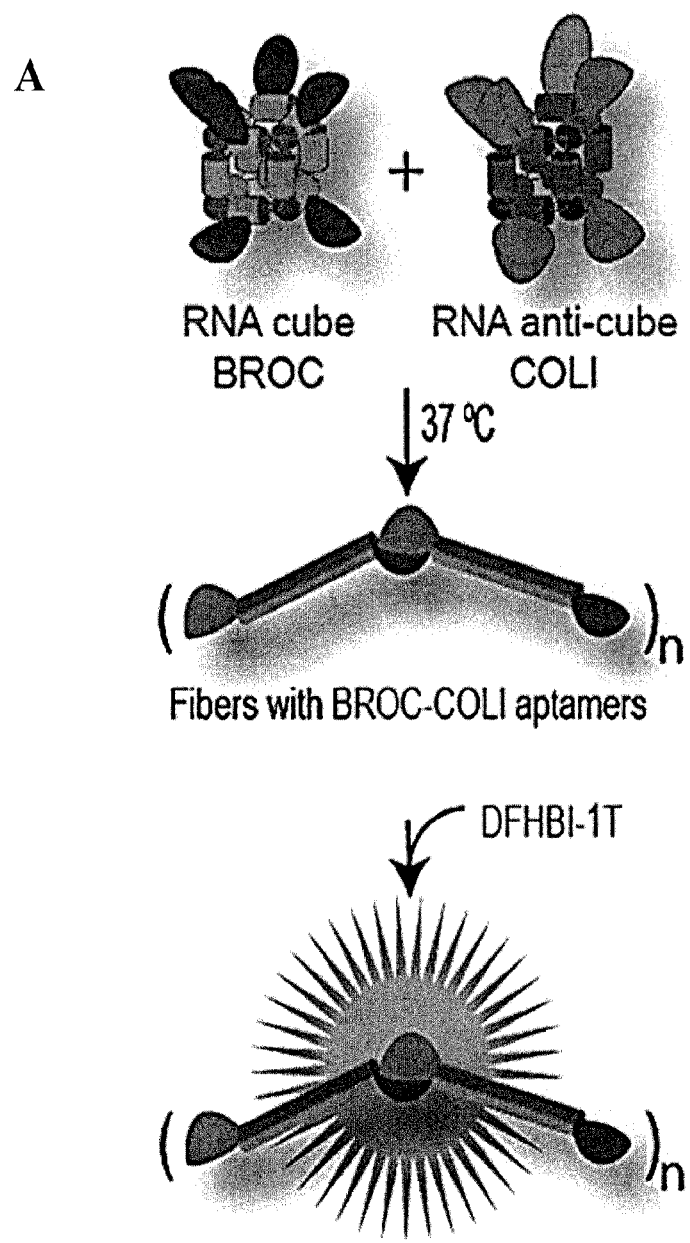
FIG. 3 shows activation of functional aptamers with isothermal re-association of shape switching nanoparticles. (A) Schematics of isothermal re-association and re-assembly of aptamers. Each of the single-stranded RNAs of the RNA cube and the RNA anti-cube are coupled with the "BROC" (on the cube) and "COLI" (on the anti-cube) aptamer halves. At 37° C., the functionalized RNA cubes and RNA anti-cubes interact, leading to simultaneous disassembly of the cube forms, and their reassociation to form duplexes, wherein the strand from the cube retains a 5' end BROC unit and the strand from the anti-cube retains a 5' end COLI unit. Thus, the annealed duplexes lead to the formation of pairing between duplexes through the interaction of the BROC and COLI units (i.e., formation of "fibers", which in the presence of DFHBI-1T, results in a fluorescence signal. (B) Total EtBr and DFHBI-1T stained native-PAGE demonstrates fiber formation and aptamer activation on re-association of cognate cubes. (C) AFM images of the aptamer-containing fibers. (D) Re-association and fiber formation can be traced by measuring fluorescence of DFHBI-1T in vitro. (E) Re-association and fiber formation can be traced by measuring fluorescence of DFHBI-1T in cells stained with DFHBI-1T. Error bars indicate s.d.; N=3.
Figure 3:
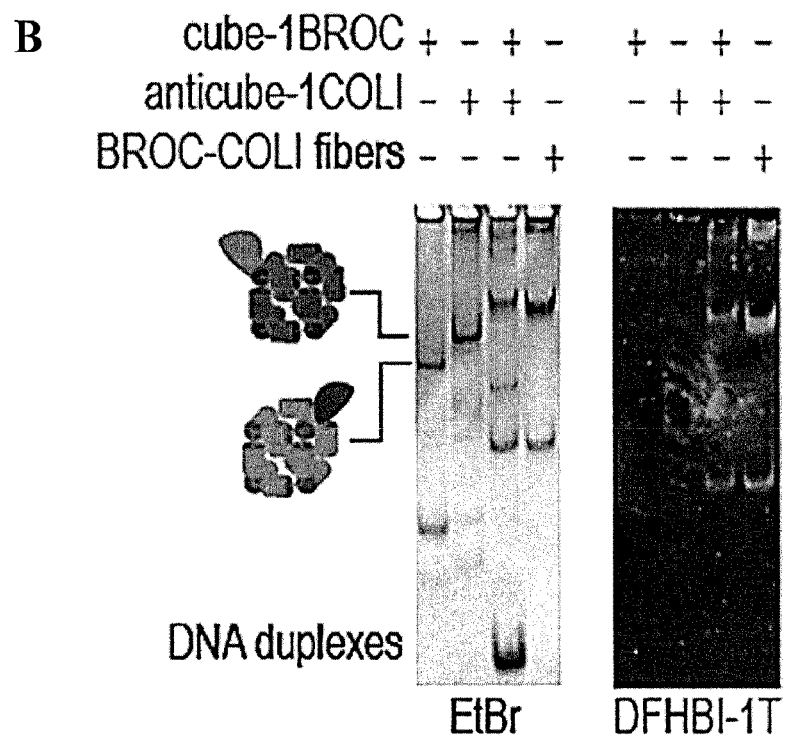
Figure 3:
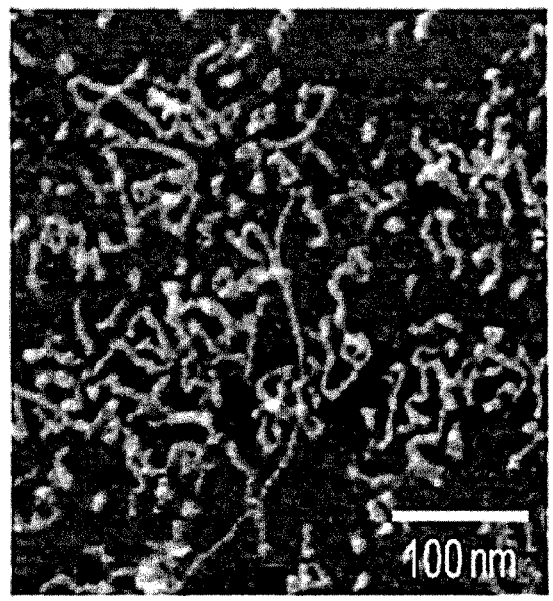
Figure 3:
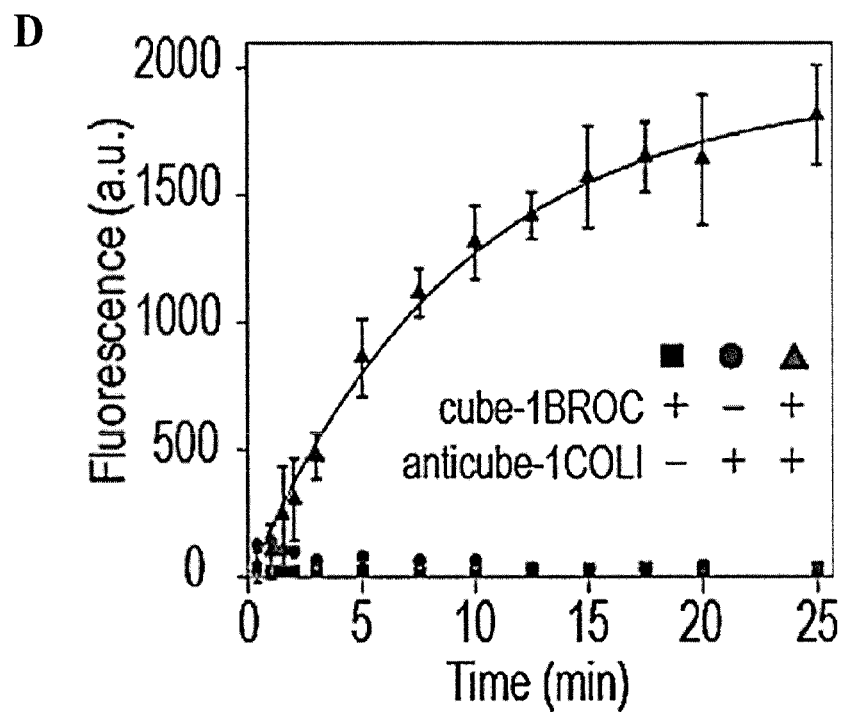
Figure 3:
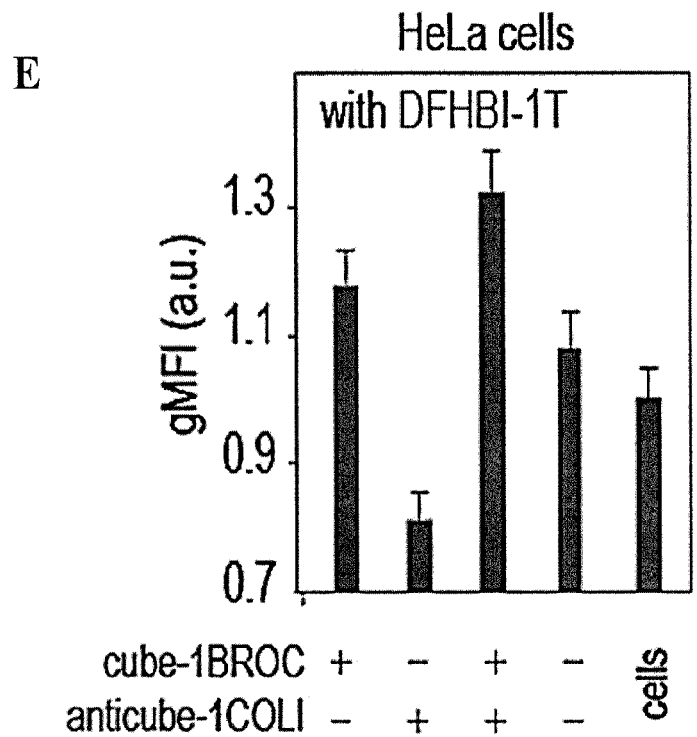

Broc-Coli is a synthetic RNA aptamer which binds the fluorophore DFHBI-1T to mimic the fluorescent spectrum of green fluorescent protein (GFP)(45). We hypothesized that the splitting of the Broc-Coli aptamer sequence into two separate non-functional strands (named Broc and Coli) can be used for monitoring the cube and anti-cube interaction and shape switching that leads to Broc and Coli re-assembly into an active fluorescent aptamer (FIG. 3A). Furthermore, this approach demonstrates the general strategy for conditional re-activation of disconnected functional ssRNAs with complex secondary structure. As predicted, the interaction of Broc-cubes with Coli-anti-cubes leads to the formation of fibers containing re-assembled Broc-Coli aptamers, thus providing an alternative optical response of interdependent nanocubes interaction. This was confirmed by native PAGE (FIG. 3B and FIG. 13) and fluorescent measurements (FIG. 3C). Flow cytometry analysis of human cervical cancer cells co-transfected with complementary nanoparticles bearing the split aptamer strands revealed the feasibility of Broc-Coli re-association into the functional structure (FIG. 3D), thus providing a new tool allowing to trace the interaction between nanoparticle formations in vivo.

Re-Association of Complementary Nanoparticles Triggers Activation of Energy Transfer and RNA Interference in Cells.

Figure 4:
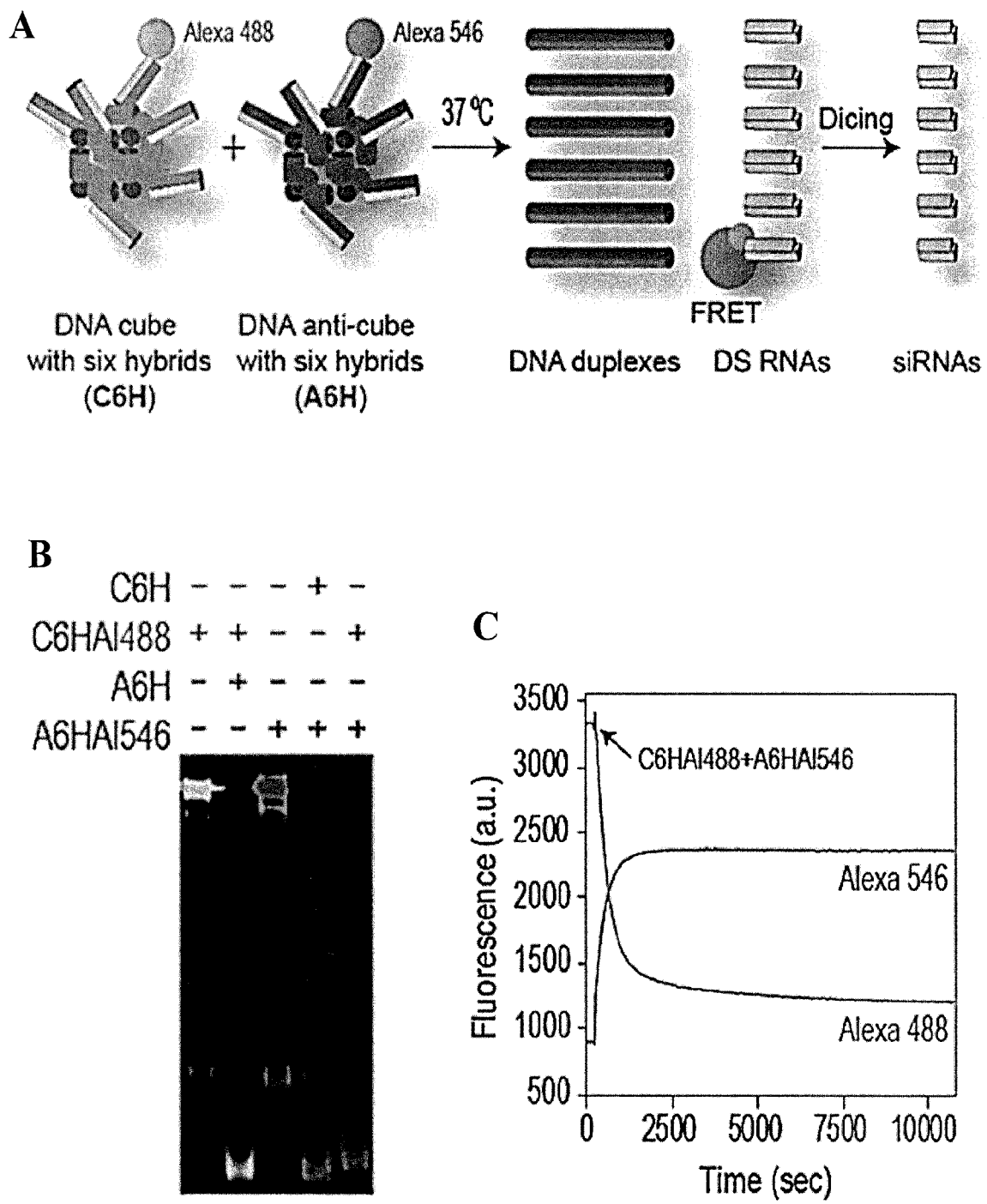
FIG. 4 shows activation of RNA interference and intracellular FRET with complementary shape switching nanoparticles. This is an example of DNA cube and anti-cubes with three (3) functionalities (1. formation of DNA duplexes, 2. formation of double-stranded RNA optical response (FRET), and 3. Dicer-processing of double-stranded RNA to form siRNAs for gene silencing. (A) Schematics of isothermal re-association and activation of FRET and RNAi. (B) In vitro re-association of fluorescently labeled cubes and anti-cubes with split DS RNAs was visualized by native-PAGE. (C) FRET time traces during re-association of fluorescently labeled with Alexa488 and Alexa546 cubes and anti-cubes carrying split Dicer Substrate RNAs (DS RNAs). (D) For intracellular FRET experiments, human prostate cancer (PC-3) cells were co-transfected with fluorescently labeled cubes and anti-cubes and images were taken on the next day. (E) Cell viability assay for Hela cells transfected with nanoparticles designed to release two DS RNAs against PLK1 and BCL2. Error bars indicate s.d.; N=3. (F-G) GFP knockdown assays for human breast cancer cells expressing enhanced GFP (MDA-MB-231/GFP). Prior to transfection formation of the nanocubes was verified by total EtBr staining of native PAGE. Three days after the transfection of cells, GFP expression was analyzed with fluorescent microscopy (F) and flow cytometry (G). As the control, pre-formed DS RNAs (at 2 nM final) against PLK1, BCL-2, and GFP were used for PC-3 and MDA-MB-231 cells respectively. Note that the individual cubes and anti-cubes cause no decrease in eGFP production. gMFI corresponds to the geometric mean fluorescence intensity. Error bars denote SEM.
Figure 4:
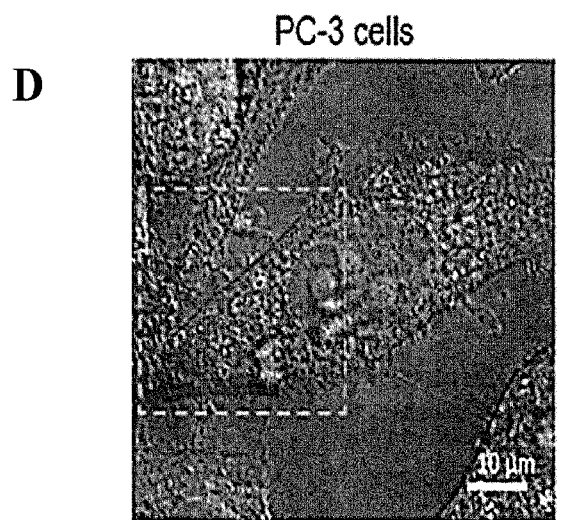
Figure 4:
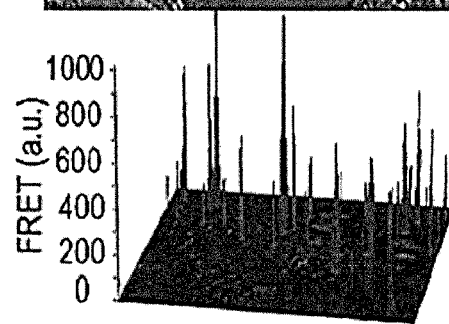
Figure 4:
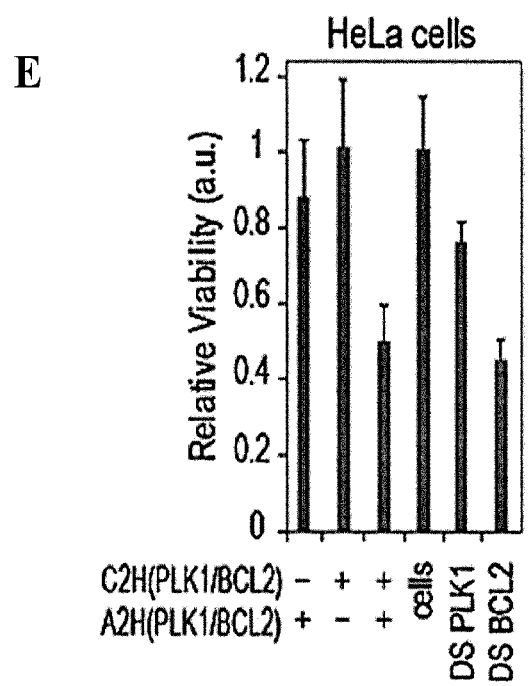
Figure 4:
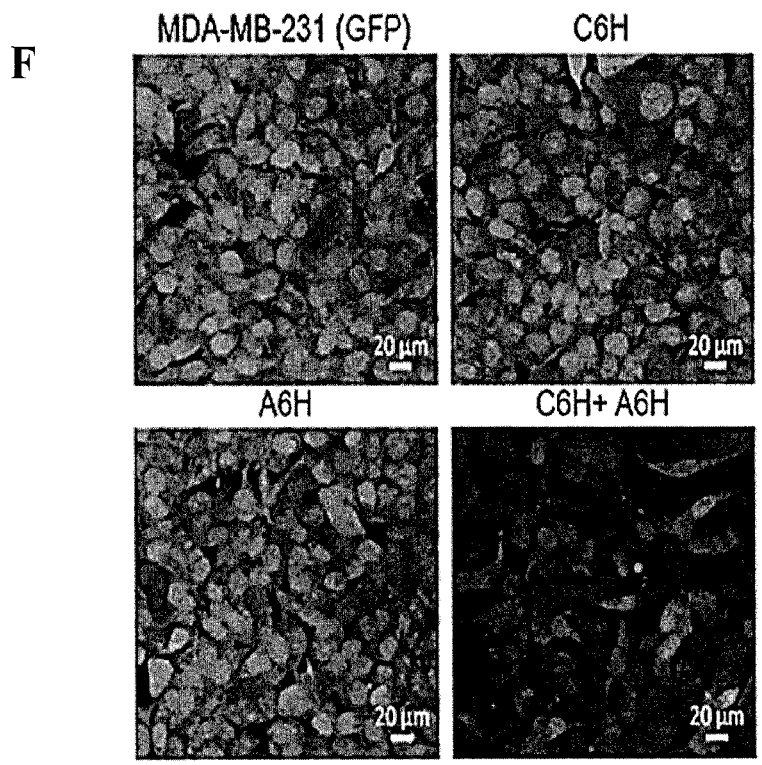
Figure 4:
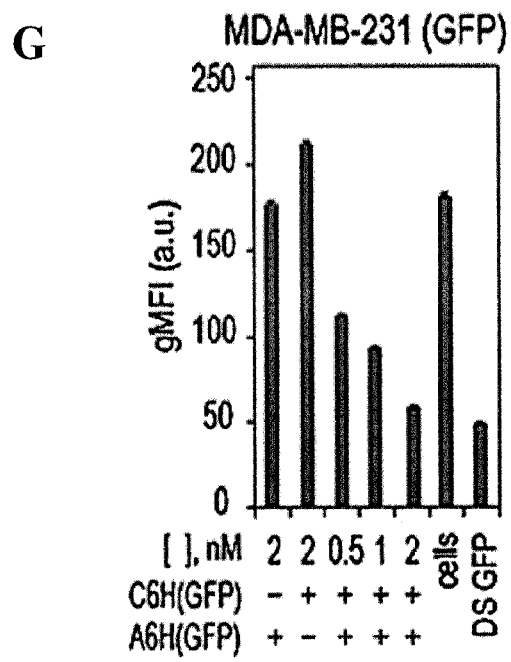

RNAi is a naturally occurring post-transcriptional gene regulation process which represses the expression of specific genes (46). Therefore, exploiting endogenous RNAi by externally delivered siRNAs is a promising tool in biotechnology and therapy. To have additional control over the initiation of targeted gene silencing is an important step forward leading towards the construction of intracellular logic gates and smart nanoparticles. We decorated two sets of cognate DNA cubes and anti-cubes with split Dicer Substrate (DS) RNAs against either BCL2 and PLK1, well-validated molecular targets, whose down-regulation induces apoptosis (47, 48), or against GFP (49). The re-association of the cube and anti-cube nanoparticles led to the formation of DS RNAs that could be further activated through dicing by releasing the functional siRNAs (FIG. 4A). In addition, split DS RNAs can be fluorescently labeled with dyes (e.g., Alexa 488 and Alexa 546) chosen to undergo FRET. Thus, the shape switching of labeled nanoparticles was not only directly visualized by native-PAGE (FIG. 4B), but also assessed in real time using FRET (FIG. 4C). With the same approach, the intracellular re-association of cubes and anti-cubes in human prostate cancer cells was traced by FRET (FIG. 4D and FIG. 14). For activation of RNA interference, prostate cancer cells were treated with nanoparticles releasing BCL2 and PLK1 DS RNAs (FIG. 4E). The cell viability was significantly decreased when both cubes were introduced, while individual cubes did not show much effect. To show the generality of the RNAi induction approach, GFP expressing breast cancer cells were treated with complementary cubes releasing DS RNAs targeting GFP. The extent of GFP silencing was assessed with fluorescent microscopy and quantified by flow cytometry (FIG. 4F-G). The results showed an efficient knock-down of GFP production upon the intracellular re-association of cubes and anti-cubes functionalized with six split DS RNAs. In comparison, transfection of cells with individual cubes or anti-cubes did not result in GFP silencing. Re-association occurs intracellularly as suggested by FRET showing that individual cubes and anti-cubes associated with transfection agent do not re-associate in solution (FIG. 14B). Efficient GFP silencing was observed at picomolar concentrations of complementary cubes (FIG. 15).

By "siRNA" is meant a double stranded RNA. Optimally, an siRNA is 18, 19, 20, 21, 22, 23, 24, 25, 26, 27, 28, 29, 30, 31, 32, 33, 34, 35 or more nucleotides in length and has a 2 base overhang at its 3' end. It is understood that the term "siRNA' includes both diceable and non-diceable siRNAs. These dsRNAs can be introduced to an individual cell or to a whole animal; for example, they may be introduced systemically via the bloodstream. Such siRNAs are used to downregulate mRNA levels or promoter activity. Functional siRNAs can be released by Dicer nuclease. Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference), as are twenty-five to thirty nucleotide Dicer substrate dsRNAs (DsiRNAs; Rossi et al. U.S. Pat. No. 8,084,599). The therapeutic effectiveness of an siRNA approach in mammals was demonstrated in vivo by McCaffrey et al. (Nature 418: 38-39, 2002).

Given the sequence of a target gene, siRNAs may be designed to inactivate that gene. Such siRNAs, for example, could be administered directly to an affected tissue, or administered systemically. The nucleic acid sequence of an Parl gene can be used to design small interfering RNAs (siRNAs). The 21 to 25 nucleotide siRNAs (or, optionally 25 to 30 nucleotide or longer DsiRNAs) may be used, for example, as therapeutics to inhibit disease related genes.

Other Complementary Nanoparticles.

Figure 5:
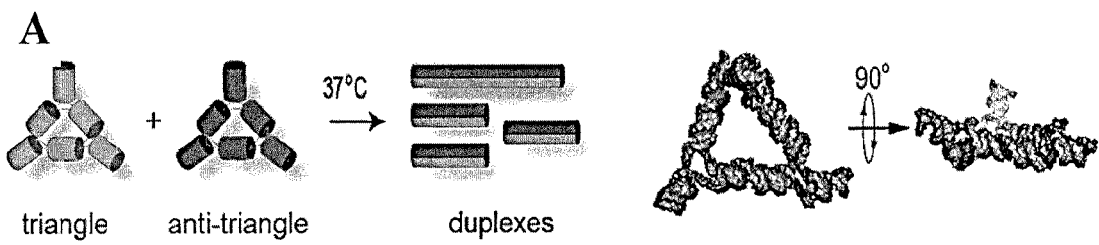
FIG. 5 shows rings and anti-rings nanoparticles do not re-associate but cognate monomers form rings and fibers, but that triangles and anti-triangles do re-associate to form duplexes. (A) Schematics of isothermal re-association of triangles and anti-triangles. (B) AFM of triangles and anti-triangles and native-PAGE of re-associated anti-triangles with triangles after 30 mins of incubation. (C) Schematics and native-PAGE showing that the RNA rings and anti-rings do not interact. (D) Contrary to assembled rings, individual monomers and anti-monomers form the mixture of ring and fiber-like structures as shown by native-PAGE and AFM.
Figure 5:
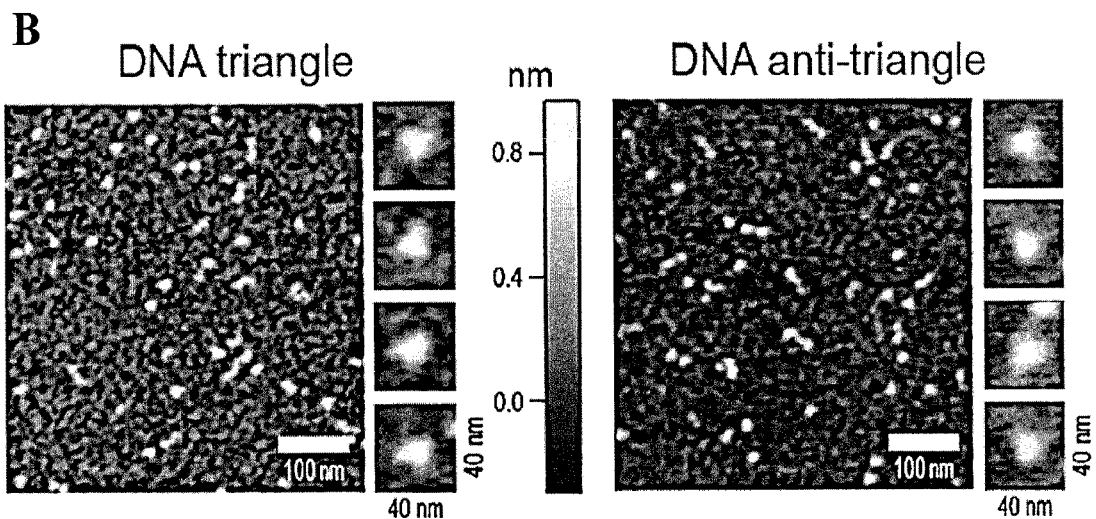
Figure 5:
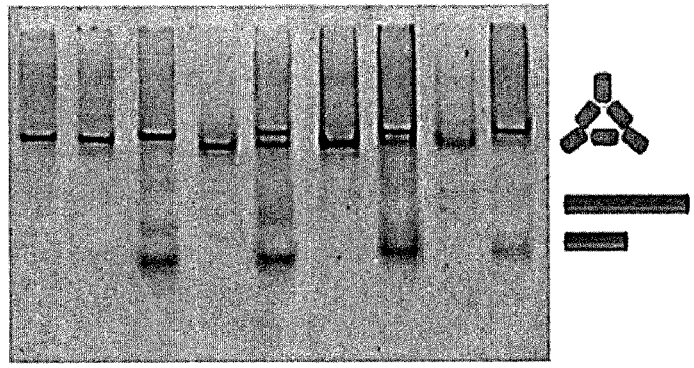
Figure 5:
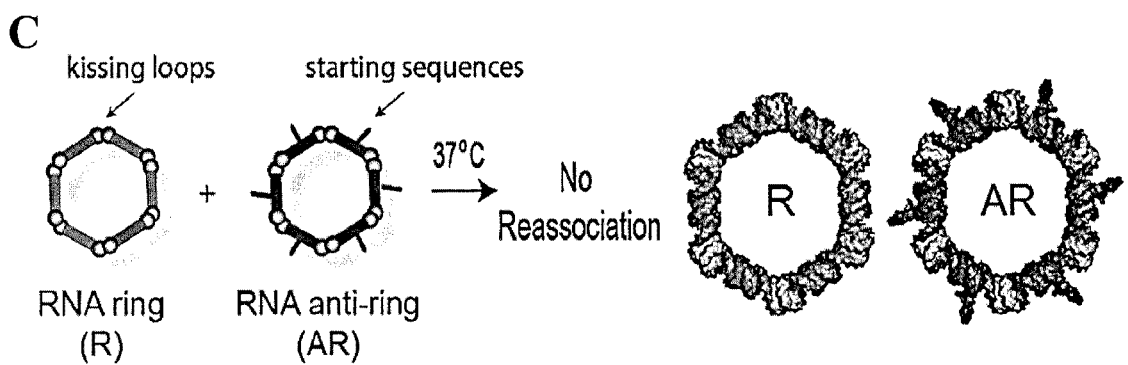
Figure 5:
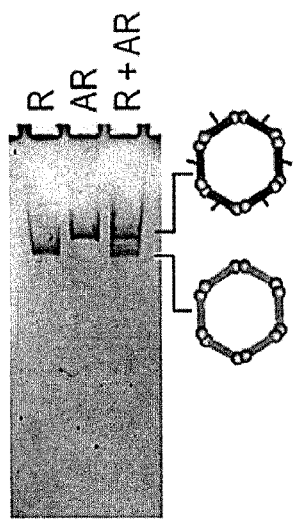
Figure 5:
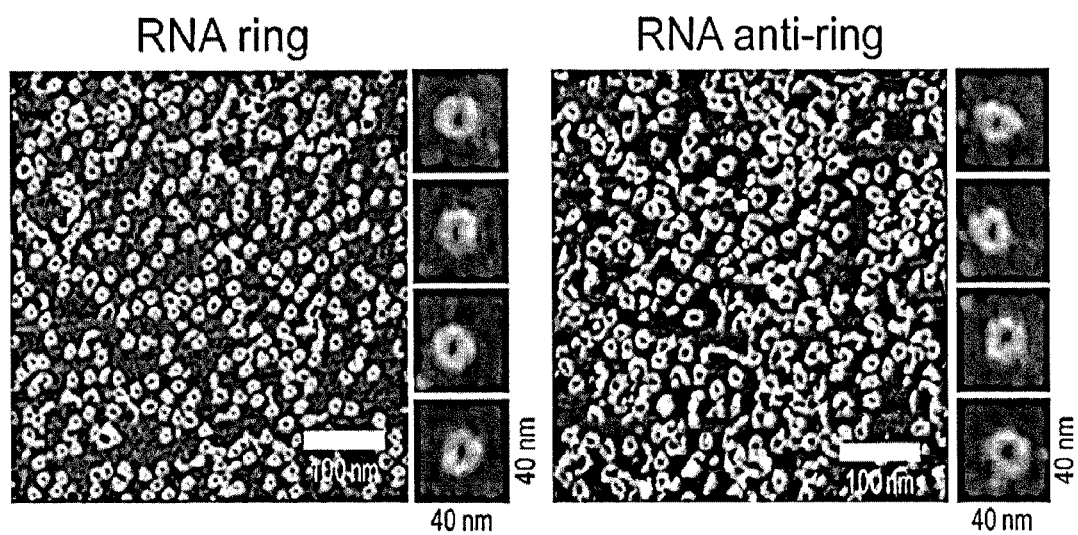
Figure 5:
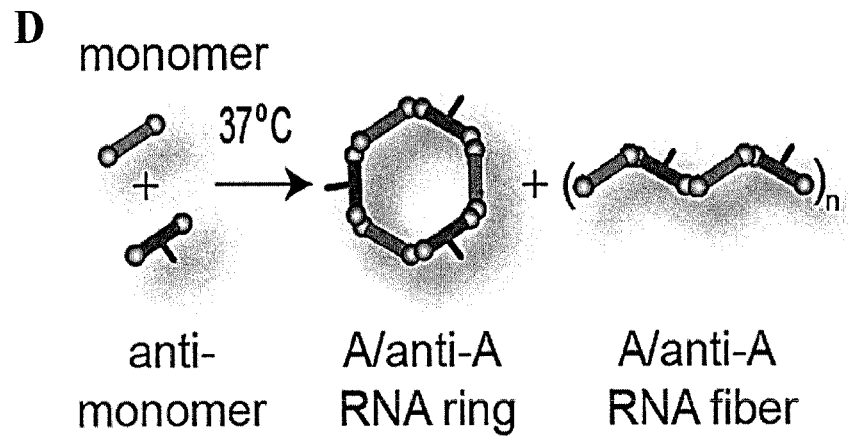
Figure 5:
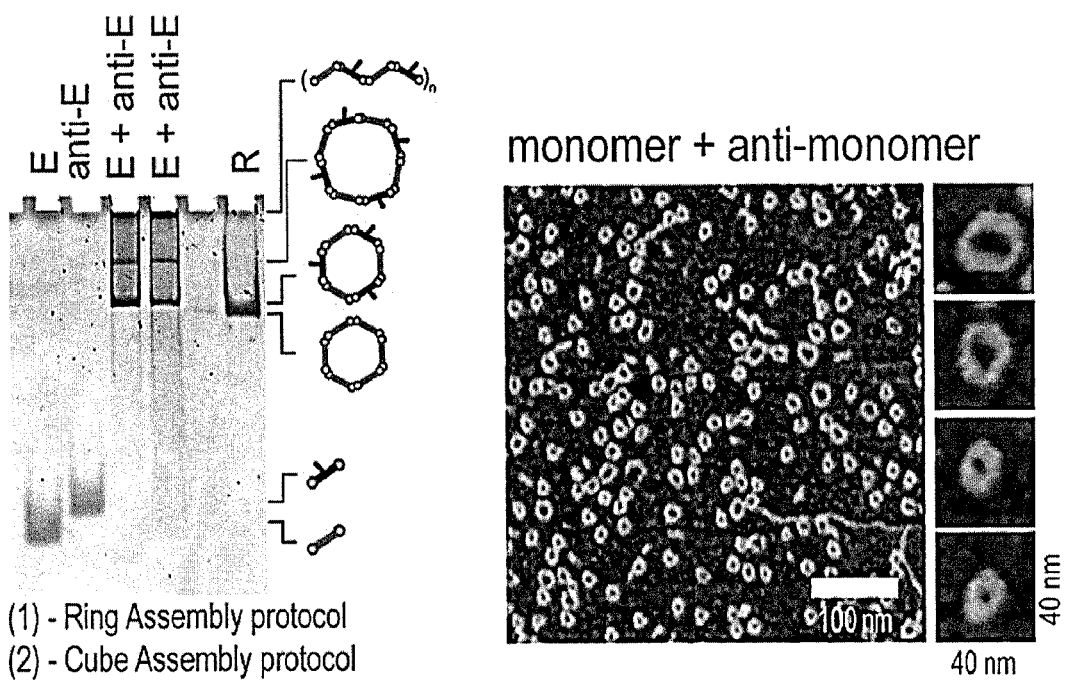

With the same design principles, several additional complementary nanoparticles were created by using previously characterized RNA triangles (38) and RNA rings (37) and their reverse complements (FIG. 5). It is expected that co-incubation of the cognate pairs will lead to the similar collapse of each structure and recombination of smaller subunits as seen in the cube and anti-cube pairs. However, while native-PAGE results showed that the incubation of triangles with anti-triangles led to the shape-switching (FIG.

5B), the rings and anti-rings did not interact (FIG. 5C). The explanation was offered by comparing ring designing principles with the cube and triangle structures. RNA nanorings did not have exposed single bases like cubes and triangles have in their corners, rather the rings were formed through interstrand RNA-RNA "kissing loops" or KL. Therefore, due to the absence of exposed bases, the reverse complement strands were unable to elicit shape-switching, and each ring remains intact as is visualized using native PAGE stained with ethidium bromide (FIG. 5C). The use of RNA tertiary interacting motifs (KL) also prevented rings from forming RNA/DNA or DNA/DNA structures (FIG. 15), as opposed to cubes and triangles. The use of complementary rings provided a simple way of expanding the library of the novel programmable nanoscaffolds, based on the existing nanodesigns, thus eliminating any laborious computational design and experimental verification. Although the intact rings would not interact, their individual subunits were complementary and form both rings as well as elongated fiber-like structures as verified by native-PAGE and AFM (FIG. 5D and FIG. 17A). The fabrication of these structures was accomplished using both the established ring and cube assembly protocol, which differ only in the incubation profile. Depending on the kissing loop sequence, the formation of either fibers (e.g., A and anti-A) or rings (e.g., F and anti-F) can be promoted (FIG. 17A). The formation of functional fibers and rings was achieved by functionalizing one of the monomers (FIG. 17B).

Conclusion

Diverse examples of mutual relations between interdependent entities exist in nature both at the levels of ecosystems and individual molecular interactions. Herein, the Example presents a new concept of dynamic interdependent nucleic acid nanoparticles. The approach outlined above relies on the physical interaction of two complementary nanoparticles (but initially inactive) with controllable thermodynamic and chemical properties. The findings presented in this Example also suggest that by simply optimizing the ratio between RNA and DNA strands entering the composition of assemblies, one can create nanoparticles with optimal immunomodulatory properties when activation of the immune system is desirable (e.g., vaccines and immunotherapy). However, other types of RNA nanoparticles may expose different immunomodulatory properties (51). After interaction of the cognate nanoparticles both in vitro and in human cells, as demonstrated in three different cell lines, constructs undergo isothermal shape-switching resulting in activation of one or more functionalities including RNAi, optical response, transcription and split aptamer re-assembly. Importantly, only two nanoparticles are required to simultaneously activate multiple functionalities and no ssRNA or ssDNA toeholds are needed to initiate the interaction. Moreover, in the case of co transcriptional assemblies, only one specifically designed DNA nanoparticle is needed to efficiently produce an RNA counterpart. Overall, the presented strategy allows for the use of simple, multifunctional and conditionally activated nanoparticles and provides a promising future for their use in nanobioscience.

Further discussion on RNA and DNA nanoparticles, nanocubes and RNA interference can be found in Afonin et al., *Triggering of RNA Interference with RNA-RNA, RNA-DNA, and DNA-RNA Nanoparticles*, ACS Nano, Vol. 9, No. 1, pp. 251-259, published online Dec. 18, 2014 and Afonin K A., *Multifunctional RNA nanoparticles*, Nano Lett., Vol. 14, No. 10, pp. 5662-71, Oct. 8, 2014 and a pending U.S. application Ser. No. 15/309,157 with a priority date of 6 May 2014 each of which are incorporate herein by reference in their entireties.

EQUIVALENTS

Those skilled in the art will recognize, or be able to ascertain using no more than routine experimentation, many equivalents to the specific embodiments of the invention described herein. Such equivalents are intended to be encompassed by the following claims. [1] Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

REFERENCES

The following specific references, also incorporated by reference, are indicated above by corresponding reference number.

1. Afonin, K. A. et al. In vitro assembly of cubic RNA-based scaffolds designed in silico. *Nature nanotechnology* 5, 676-682 (2010).
2. Guo, P. The emerging field of RNA nanotechnology. *Nature nanotechnology* 5, 833-842 (2010).
3. Guo, P., Zhang, C., Chen, C., Garver, K. & Trottier, M. Inter-RNA interaction of phage phi29 pRNA to form a hexameric complex for viral DNA transportation. *Mol Cell* 2, 149-155 (1998).
4. Hague, F. et al. Ultrastable synergistic tetravalent RNA nanoparticles for targeting to cancers. *Nano today* 7, 245-257 (2012).
5. Khisamutdinov, E. F., Jasinski, D. L. & Guo, P. RNA as a boiling-resistant anionic polymer material to build robust structures with defined shape and stoichiometry. *ACS Nano* 8, 4771-4781 (2014).
6. He, Y. et al. Hierarchical self-assembly of DNA into symmetric supramolecular polyhedra. *Nature* 452, 198-201 (2008).
7. Yu, J., Liu, Z., Jiang, W., Wang, G. & Mao, C. De novo design of an RNA tile that self-assembles into a homo-octameric nanoprism. *Nat Commun* 6, 5724 (2015).
8. Geary, C., Rothemund, P. W. & Andersen, E. S. RNA nanostructures. A single-stranded architecture for cotranscriptional folding of RNA nanostructures. *Science* 345, 799-804 (2014).
9. Rothemund, P. W. K. Folding DNA to create nanoscale shapes and patterns. *Nature* 440, 297-302 (2006).
10. Ohno, H. et al. Synthetic RNA-protein complex shaped like an equilateral triangle. *Nature nanotechnology* 6, 116-120 (2011).
11. Osada, E. et al. Engineering RNA-protein complexes with different shapes for imaging and therapeutic applications. *ACS Nano* 8, 8130-8140 (2014).

12. Pinheiro, A. V., Han, D., Shih, W. M. & Yan, H. Challenges and opportunities for structural DNA nanotechnology. *Nature nanotechnology* 6, 763-772 (2011).
13. Lee, H. et al. Molecularly self-assembled nucleic acid nanoparticles for targeted in vivo siRNA delivery. *Nature nanotechnology* 7, 389-393 (2012).
14. Mao, C., Sun, W., Shen, Z. & Seeman, N. C. A nanomechanical device based on the B-Z transition of DNA. *Nature* 397, 144-146 (1999).
15. Modi, S. et al. A DNA nanomachine that maps spatial and temporal pH changes inside living cells. *Nature nanotechnology* 4, 325-330 (2009).
16. Modi, S., Nizak, C., Surana, S., Halder, S. & Krishnan, Y. Two DNA nanomachines map pH changes along intersecting endocytic pathways inside the same cell. *Nature nanotechnology* 8, 459-467 (2013).
17. Zhou, M., Liang, X., Mochizuki, T. & Asanuma, H. A light-driven DNA nanomachine for the efficient photoswitching of RNA digestion. *Angew. Chem. Int. Ed. Engl.* 49, 2167-2170 (2010).
18. Yurke, B., Turberfield, A. J., Mills, A. P., Simmel, F. C. & Neumann, J. L. A DNA-fuelled molecular machine made of DNA. *Nature* 406, 605-608 (2000).
19. Shin, J.-S. & Pierce, N. A. A synthetic DNA walker for molecular transport. *J. Am. Chem. Soc.* 126, 10834-10835 (2004).
20. Bath, J., Green, S. J. & Turberfield, A. J. A free-running DNA motor powered by a nicking enzyme. *Angew. Chem. Int. Ed. Engl.* 44, 4358-4361 (2005).
21. Chen, Y., Wang, M. & Mao, C. An autonomous DNA nanomotor powered by a DNA enzyme. *Angew. Chem. Int. Ed. Engl.* 43, 3554-3557 (2004).
22. Lund, K. et al. Molecular robots guided by prescriptive landscapes. *Nature* 465, 206-210 (2010).
23. Andersen, E. S. et al. Self-assembly of a nanoscale DNA box with a controllable lid. *Nature* 459, 73-76 (2009).
24. Douglas, S. M., Bachelet, I. & Church, G. M. A logic-gated nanorobot for targeted transport of molecular payloads. *Science* 335, 831-834 (2012).
25. Bujold, K. E. et al. Sequence-responsive unzipping DNA cubes with tunable cellular uptake profiles. *Chem. Sci.* 5, 2449-2455 (2014).
26. Jimenez, R. M., Polanco, J. A. & Luptak, A. Chemistry and Biology of Self-Cleaving Ribozymes. *Trends Biochem Sci* 40, 648-661 (2015).
27. Mironov, A. S. et al. Sensing small molecules by nascent RNA: a mechanism to control transcription in bacteria. *Cell* 111, 747-756 (2002).
28. Righetti, F. et al. Temperature-responsive in vitro RNA structurome of *Yersinia pseudotuberculosis*. *Proc Natl Acad Sci USA* 113, 7237-7242 (2016).
29. Winkler, W. C., Cohen-Chalamish, S. & Breaker, R. R. An mRNA structure that controls gene expression by binding FMN. *Proc. Natl. Acad. Sci. U.S.A.* 99, 15908-15913 (2002).
30. Bindewald, E. et al. Multistrand Structure Prediction of Nucleic Acid Assemblies and Design of RNA Switches. *Nano letters* 16, 1726-1735 (2016).
31. Afonin, K. A. et al. Activation of different split functionalities on re-association of RNA-DNA hybrids. *Nature nanotechnology* 8, 296-304 (2013).
32. Afonin, K. A. et al. The Use of Minimal RNA Toeholds to Trigger the Activation of Multiple Functionalities. *Nano letters* 16, 1746-1753 (2016).
33. Groves, B. et al. Computing in mammalian cells with nucleic acid strand exchange. *Nature nanotechnology* 11, 287-294 (2016).
34. Afonin, K. A. et al. Co-transcriptional production of RNA-DNA hybrids for simultaneous release of multiple split functionalities. *Nucleic acids research* 42, 2085-2097 (2014).
35. Afonin, K. A. et al. Triggering of RNA Interference with RNA-RNA, RNA-DNA, and DNA-RNA Nanoparticles. *ACS Nano* 9, 251-259 (2015).
36. Afonin, K. A. et al. Multifunctional RNA nanoparticles. *Nano letters* 14, 5662-5671 (2014).
37. Grabow, W. W. et al. Self-assembling RNA nanorings based on RNAI/II inverse kissing complexes. *Nano letters* 11, 878-887 (2011).
38. Bui, M. N. et al. Versatile RNA Tetra-U Helix Linking Motif as a Toolkit for Nucleic Acid Nanotechnology. *submitted* (2016).
39. Dobrovolskaia, M. A. & McNeil, S E Immunological and hematological toxicities challenging clinical translation of nucleic acid-based therapeutics. *Expert opinion on biological therapy* 15, 1023-1048 (2015).
40. Blanco, P., Palucka, A. K., Pascual, V. & Banchereau, J. Dendritic cells and cytokines in human inflammatory and autoimmune diseases. *Cytokine & growth factor reviews* 19, 41-52 (2008).
41. Takanohashi, A. et al. Elevation of proinflammatory cytokines in patients with Aicardi-Goutieres syndrome. *Neurology* 80, 997-1002 (2013).
42. Zamanian-Daryoush, M. et al. Determinants of cytokine induction by small interfering RNA in human peripheral blood mononuclear cells. *Journal of interferon & cytokine research: the official journal of the International Society for Interferon and Cytokine Research* 28, 221-233 (2008).
43. Turner, M. D., Nedjai, B., Hurst, T. & Pennington, D. J. Cytokines and chemokines: At the crossroads of cell signalling and inflammatory disease. *Biochimica et biophysica acta* 1843, 2563-2582 (2014).
44. Elroy-Stein, O. & Moss, B. Cytoplasmic expression system based on constitutive synthesis of bacteriophage T7 RNA polymerase in mammalian cells. *Proc Natl Acad Sci USA* 87, 6743-6747 (1990).
45. Filonov, G. S., Moon, J. D., Svensen, N. & Jaffrey, S. R. Broccoli: rapid selection of an RNA mimic of green fluorescent protein by fluorescence-based selection and directed evolution. *J. Am. Chem. Soc.* 136, 16299-16308 (2014).
46. Fire, A. et al. Potent and specific genetic interference by double-stranded RNA in Caenorhabditis elegans. *Nature* 391, 806-811 (1998).
47. Reagan-Shaw, S. & Ahmad, N. Silencing of polo-like kinase (Plk) 1 via siRNA causes induction of apoptosis and impairment of mitosis machinery in human prostate cancer cells: implications for the treatment of prostate cancer. *The FASEB journal* 19, 611-613 (2005).
48. Ruckert, F. et al. Simultaneous gene silencing of Bcl-2, XIAP and Survivin re-sensitizes pancreatic cancer cells towards apoptosis. *BMC cancer* 10, 379 (2010).
49. Rose, S. D. et al. Functional polarity is introduced by Dicer processing of short substrate RNAs. *Nucleic acids research* 33, 4140-4156 (2005).
50. Shlyakhtenko, L. S., Gall, A. A. & Lyubchenko, Y. L. Mica functionalization for imaging of DNA and protein-DNA complexes with atomic force microscopy. *Methods in molecular biology* 931, 295-312 (2013).
51. Khisamutdinov, E. F., et al., "Enhancing immunomodulation on innate immunity by shape transition among RNA triangle, square and pentagon nanovehicles. *Nucleic Acicds Res.*, 42, pp. 9996-10004 (2014).

The invention claimed is:

1. A nanoparticle system for simultaneous delivery of multiple latent but activatable functionalities, the system comprising at least two complementary nanoparticles, wherein a first nanoparticle or scaffold comprises DNA and/or RNA oligonucleotides, and a second nanoparticle or anti-scaffold which is complementary to the first nanoparticle comprises reverse complementary DNA and/or RNA oligonucleotides of the first nanoparticle; wherein the complementary nanoparticles are capable of undergoing an interaction under physiological conditions that results in their re-association to release one or more functional duplexes comprising the DNA and/or RNA oligonucleotides each paired with its reverse complementary DNA and/or RNA oligonucleotides, and wherein the nanoparticles are not rings and have no single stranded toeholds.

2. The system of claim 1, wherein the functionalities are selected from the group consisting of RNAi, transcription, gene silencing, optical response, RNA cube formation, and split aptamer.

3. The system of claim 1, wherein the nanoparticles are cubes, tubes, or triangles.

4. The system of claim 1, wherein ratio of DNA and RNA in nanoparticles controls the immunostimulatory activity, thermodynamic stability, resistance to nuclease degradation, and rate of re-association of nanoparticles.

5. The system of claim 1, wherein the oligonucleotides control more than one function after re-association.

6. The system of claim 1, wherein the complementary nanoparticles comprise six stranded cubes and anti-cubes.

7. The system of claim 6, wherein cubes and anti-cubes comprise RNA oligonucleotides, DNA oligonucleotides or DNA and RNA oligonucleotides in various ratios.

8. The system of claim 6, wherein the cubes are comprised of DNA oligonucleotides.

9. The system of claim 6, wherein the cubes are comprised of RNA oligonucleotides.

10. The system of claim 6, wherein the anti-cubes have DNA or RNA oligonucleotides.

11. The system of claim 7, wherein the DNA or RNA oligonucleotides comprise more than one functionality that becomes activated after re-association.

12. The system of claim 11, wherein functionalities that get activated after re-association are RNAi agents, split DS RNAs, transcription promoters, T7 RNA polymerase promotors, optical response markers, and split aptamers.

13. The system of claim 12, wherein the dsRNAs are Dicer substrates.

14. The system of claim 12, wherein the dsRNAs are dsRNAs that are active RNAi agents.

15. The system of claim 6, wherein all six oligonucleotide strands comprise arm sequences.

16. The system of claim 15, wherein the arm sequences are a sense or an antisense strand of a split RNAi agent.

17. The system of claim 6, wherein a split RNAi agent of each arm of the RNA nanocube targets a different target gene sequence.

18. The system of claim 6, wherein the different target gene sequences are viral sequences.

19. A composition comprising the system of claim 6 and a lipid-based delivery system.

20. The system of claim 19, wherein nanoparticles after delivery induce immune response upon re-association.

* * * * *

SEQUENCE LISTING

<160> NUMBER OF SEQ ID NOS: 105

<210> SEQ ID NO 1
<211> LENGTH: 52
<212> TYPE: DNA
<213> ORGANISM: Artificial Sequence
<220> FEATURE:
<223> OTHER INFORMATION: synthetic

<400> SEQUENCE: 1
ggcaactttg atccctcggt ttagcgccgg cctttctcc cacactttca cg    52

<210> SEQ ID NO 2
<211> LENGTH: 52
<212> TYPE: DNA
<213> ORGANISM: Artificial Sequence
<220> FEATURE:
<223> OTHER INFORMATION: synthetic

<400> SEQUENCE: 2
gggaaatttc gtggtaggtt tgttgcccg tgtttctacg attactttgg tc    52

<210> SEQ ID NO 3
<211> LENGTH: 52
<212> TYPE: DNA
<213> ORGANISM: Artificial Sequence
<220> FEATURE:
<223> OTHER INFORMATION: synthetic

<400> SEQUENCE: 3
ggacattttc gagacagcat tttttcccga cctttgcgga ttgtatttta gg    52

<210> SEQ ID NO 4
<211> LENGTH: 52
<212> TYPE: DNA
<213> ORGANISM: Artificial Sequence
<220> FEATURE:
<223> OTHER INFORMATION: synthetic

<400> SEQUENCE: 4
ggcgcttttg accttctgct ttatgtcccc tatttcttaa tgacttttgg cc    52

<210> SEQ ID NO 5
<211> LENGTH: 52
<212> TYPE: DNA
<213> ORGANISM: Artificial Sequence
<220> FEATURE:
<223> OTHER INFORMATION: synthetic

<400> SEQUENCE: 5
gggagattta gtcattaagt tttacaatcc gctttgtaat cgtagtttgt gt    52

<210> SEQ ID NO 6
<211> LENGTH: 52
<212> TYPE: DNA
<213> ORGANISM: Artificial Sequence
<220> FEATURE:
<223> OTHER INFORMATION: synthetic

<400> SEQUENCE: 6
gggatcttta cctaccacgt tttgctgtct cgtttgcaga aggtctttcc ga    52

<210> SEQ ID NO 7
<211> LENGTH: 52
<212> TYPE: DNA
<213> ORGANISM: Artificial Sequence

```
<220> FEATURE:
<223> OTHER INFORMATION: synthetic
<220> FEATURE:
<221> NAME/KEY: misc_feature
<222> LOCATION: (52)..(52)
<223> OTHER INFORMATION: wherein the cytosine at position 52 is labeled
      with Alexa 488

<400> SEQUENCE: 7
ggcgcttttg accttctgct ttatgtcccc tatttcttaa tgactttggg cc          52

<210> SEQ ID NO 8
<211> LENGTH: 52
<212> TYPE: DNA
<213> ORGANISM: Artificial Sequence
<220> FEATURE:
<223> OTHER INFORMATION: synthetic

<400> SEQUENCE: 8
cgtgaaagtg tgggagaaaa ggccggcgct aaaccgaggg atcaaagttg cc          52

<210> SEQ ID NO 9
<211> LENGTH: 52
<212> TYPE: DNA
<213> ORGANISM: Artificial Sequence
<220> FEATURE:
<223> OTHER INFORMATION: synthethic

<400> SEQUENCE: 9
gaccaaagta atcgtagaaa cacgggcaac aaaacctacc acgaaatttc cc          52

<210> SEQ ID NO 10
<211> LENGTH: 52
<212> TYPE: DNA
<213> ORGANISM: Artificial Sequence
<220> FEATURE:
<223> OTHER INFORMATION: synthetic

<400> SEQUENCE: 10
cctaaaatac aatccgcaaa ggtcgggaaa aaatgctgtc tcgaaaatgt cc          52

<210> SEQ ID NO 11
<211> LENGTH: 52
<212> TYPE: DNA
<213> ORGANISM: Artificial Sequence
<220> FEATURE:
<223> OTHER INFORMATION: synthetic

<400> SEQUENCE: 11
ggccaaaagt cattaagaaa tagggggacat aaagcagaag gtcaaaagcg cc         52

<210> SEQ ID NO 12
<211> LENGTH: 52
<212> TYPE: DNA
<213> ORGANISM: Artificial Sequence
<220> FEATURE:
<223> OTHER INFORMATION: synthetic

<400> SEQUENCE: 12
acacaaacta cgattacaaa gcggattgta aaacttaatg actaaatctc cc          52

<210> SEQ ID NO 13
<211> LENGTH: 52
<212> TYPE: DNA
<213> ORGANISM: Artificial Sequence
<220> FEATURE:
<223> OTHER INFORMATION: synthetic
```

<400> SEQUENCE: 13
tcggaaagac cttctgcaaa cgagacagca aaacgtggta ggtaaagatc cc    52

<210> SEQ ID NO 14
<211> LENGTH: 52
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (52)..(52)
<223> OTHER INFORMATION: wherein the cytosine at position 52 is labeled
      with Cy5

<400> SEQUENCE: 14
cgtgaaagtg tgggagaaaa ggccggcgct aaaccgaggg atcaaagttg cc    52

<210> SEQ ID NO 15
<211> LENGTH: 52
<212> TYPE: RNA
<213> ORGANISM: Artificial Sequence
<220> FEATURE:
<223> OTHER INFORMATION: synthetic

<400> SEQUENCE: 15
ggcaacuuug aucccucggu uuagcgccgg ccuuuucucc cacacuuuca cg    52

<210> SEQ ID NO 16
<211> LENGTH: 52
<212> TYPE: RNA
<213> ORGANISM: Artificial Sequence
<220> FEATURE:
<223> OTHER INFORMATION: synthetic

<400> SEQUENCE: 16
gggaaauuuc gugguagguu uuguugcccg uguucuacg auuacuuugg uc    52

<210> SEQ ID NO 17
<211> LENGTH: 52
<212> TYPE: RNA
<213> ORGANISM: Artificial Sequence
<220> FEATURE:
<223> OTHER INFORMATION: synthetic

<400> SEQUENCE: 17
ggacauuuuc gagacagcau uuuucccga ccuuugcgga uuguauuuua gg    52

<210> SEQ ID NO 18
<211> LENGTH: 52
<212> TYPE: RNA
<213> ORGANISM: Artificial Sequence
<220> FEATURE:
<223> OTHER INFORMATION: synthetic

<400> SEQUENCE: 18
ggcgcuuuug accuucugcu uuaugucccc uauuucuuaa ugacuuuugg cc    52

<210> SEQ ID NO 19
<211> LENGTH: 52
<212> TYPE: RNA
<213> ORGANISM: Artificial Sequence
<220> FEATURE:
<223> OTHER INFORMATION: synthetic

<400> SEQUENCE: 19
gggagauuua gucauuaagu uuuacaaucc gcuuuguaau cguaguuugu gu         52

<210> SEQ ID NO 20
<211> LENGTH: 52
<212> TYPE: RNA
<213> ORGANISM: Artificial Sequence
<220> FEATURE:
<223> OTHER INFORMATION: synthetic

<400> SEQUENCE: 20
gggaucuuua ccuaccacgu uuugcugucu cguuugcaga aggucuuucc ga         52

<210> SEQ ID NO 21
<211> LENGTH: 52
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (52)..(52)
<223> OTHER INFORMATION: wherein the cytosine at position 52 is labeled
      with Alexa 488

<400> SEQUENCE: 21 ggcgcuuug accuucugcu uuaugucccc uauuucuuaa ugacuuuugg cc         52

<210> SEQ ID NO 22
<211> LENGTH: 72
<212> TYPE: DNA
<213> ORGANISM: Artificial Sequence
<220> FEATURE:
<223> OTHER INFORMATION: synthetic

<400> SEQUENCE: 22
ttctaatacg actcactata ggcaactttg atccctcggt ttagcgccgg cctttctcc   60 cacactttca cg                                                     72

<210> SEQ ID NO 23
<211> LENGTH: 72
<212> TYPE: DNA
<213> ORGANISM: Artificial Sequence
<220> FEATURE:
<223> OTHER INFORMATION: synthetic

<400> SEQUENCE: 23
ttctaatacg actcactata gggaaatttc gtggtaggtt ttgttgcccg tgtttctacg   60
attactttgg tc                                                     72

<210> SEQ ID NO 24
<211> LENGTH: 72
<212> TYPE: DNA
<213> ORGANISM: Artificial Sequence
<220> FEATURE:
<223> OTHER INFORMATION: synthetic

<400> SEQUENCE: 24
ttctaatacg actcactata ggacattttc gagacagcat tttttcccga cctttgcgga   60 ttgtattta gg                                                      72

<210> SEQ ID NO 25
<211> LENGTH: 72
<212> TYPE: DNA
<213> ORGANISM: Artificial Sequence

```
<220> FEATURE:
<223> OTHER INFORMATION: synthetic

<400> SEQUENCE: 25
ttctaatacg actcactata ggcgcttttg accttctgct ttatgtcccc tatttcttaa    60
tgacttttgg cc                                                        72

<210> SEQ ID NO 26
<211> LENGTH: 72
<212> TYPE: DNA
<213> ORGANISM: Artificial Sequence
<220> FEATURE:
<223> OTHER INFORMATION: synthetic

<400> SEQUENCE: 26
ttctaatacg actcactata gggagattta gtcattaagt tttacaatcc gctttgtaat    60
cgtagtttgt gt                                                        72

<210> SEQ ID NO 27
<211> LENGTH: 72
<212> TYPE: DNA
<213> ORGANISM: Artificial Sequence
<220> FEATURE:
<223> OTHER INFORMATION: synthetic

<400> SEQUENCE: 27
ttctaatacg actcactata gggatctttta cctaccacgt tttgctgtct cgtttgcaga    60
aggtctttcc ga                                                        72

<210> SEQ ID NO 28
<211> LENGTH: 20
<212> TYPE: DNA
<213> ORGANISM: Artificial Sequence
<220> FEATURE:
<223> OTHER INFORMATION: synthetic

<400> SEQUENCE: 28
tatagtgagt cgtattagaa                                                20

<210> SEQ ID NO 29
<211> LENGTH: 11
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: wherein the guanine at position 11 is labeled
      with Alexa 488

<400> SEQUENCE: 29
atagtgagtc g                                                         11

<210> SEQ ID NO 30
<211> LENGTH: 72
<212> TYPE: DNA
<213> ORGANISM: Artificial Sequence
<220> FEATURE:
<223> OTHER INFORMATION: synthetic

<400> SEQUENCE: 30
cgtgaaagtg tgggagaaaa ggccggcgct aaaccgaggg atcaaagttg cctatagtga    60
gtcgtattag aa                                                        72
```

<210> SEQ ID NO 31
<211> LENGTH: 72
<212> TYPE: DNA
<213> ORGANISM: Artificial Sequence
<220> FEATURE:
<223> OTHER INFORMATION: synthetic

<400> SEQUENCE: 31
gaccaaagta atcgtagaaa cacgggcaac aaaacctacc acgaaatttc cctatagtga    60
gtcgtattag aa                                                       72

<210> SEQ ID NO 32
<211> LENGTH: 72
<212> TYPE: DNA
<213> ORGANISM: Artificial Sequence
<220> FEATURE:
<223> OTHER INFORMATION: synthetic

<400> SEQUENCE: 32
cctaaaatac aatccgcaaa ggtcgggaaa aaatgctgtc tcgaaaatgt cctatagtga    60
gtcgtattag aa                                                       72

<210> SEQ ID NO 33
<211> LENGTH: 72
<212> TYPE: DNA
<213> ORGANISM: Artificial Sequence
<220> FEATURE:
<223> OTHER INFORMATION: synthetic

<400> SEQUENCE: 33
ggccaaaagt cattaagaaa taggggacat aaagcagaag gtcaaaagcg cctatagtga    60
gtcgtattag aa                                                       72

<210> SEQ ID NO 34
<211> LENGTH: 72
<212> TYPE: DNA
<213> ORGANISM: Artificial Sequence
<220> FEATURE:
<223> OTHER INFORMATION: synthetic

<400> SEQUENCE: 34
acacaaacta cgattacaaa gcggattgta aaacttaatg actaaatctc cctatagtga    60
gtcgtattag aa                                                       72

<210> SEQ ID NO 35
<211> LENGTH: 72
<212> TYPE: DNA
<213> ORGANISM: Artificial Sequence
<220> FEATURE:
<223> OTHER INFORMATION: synthetic

<400> SEQUENCE: 35
tcggaaagac cttctgcaaa cgagacagca aaacgtggta ggtaaagatc cctatagtga    60
gtcgtattag aa                                                       72

<210> SEQ ID NO 36
<211> LENGTH: 20
<212> TYPE: DNA
<213> ORGANISM: Artificial Sequence
<220> FEATURE:
<223> OTHER INFORMATION: synthetic

```
<400> SEQUENCE: 36
ttctaatacg actcactata                                              20

<210> SEQ ID NO 37
<211> LENGTH: 11
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: wherein the cytosine at position 1 is labeled
      with Alexa 546

<400> SEQUENCE: 37
cgactcacta t                                                       11

<210> SEQ ID NO 38
<211> LENGTH: 112
<212> TYPE: RNA
<213> ORGANISM: Artificial Sequence
<220> FEATURE:
<223> OTHER INFORMATION: synthetic

<400> SEQUENCE: 38
gggaaaguug ccauguguau gugggagacg gucggguccA gauauucgua ucugucgagu    60
agaguguggg cucccacaua cucugaugau ccuucgggau cauucauggc aa           112

<210> SEQ ID NO 39
<211> LENGTH: 45
<212> TYPE: RNA
<213> ORGANISM: Artificial Sequence
<220> FEATURE:
<223> OTHER INFORMATION: synthetic

<400> SEQUENCE: 39
gggaaauugc caugu guaug ugggagacgg ucggguccag auauu                  45

<210> SEQ ID NO 40
<211> LENGTH: 72
<212> TYPE: RNA
<213> ORGANISM: Artificial Sequence
<220> FEATURE:
<223> OTHER INFORMATION: synthetic

<400> SEQUENCE: 40
gggaaacgua ucugucgagu agaguguggg cucccacaua cucugaugau ccuucgggau    60
cauucauggc aa                                                       72

<210> SEQ ID NO 41
<211> LENGTH: 96
<212> TYPE: RNA
<213> ORGANISM: Artificial Sequence
<220> FEATURE:
<223> OTHER INFORMATION: synthetic

<400> SEQUENCE: 41
gggaauugcc auguguaugu gggagacggu cgguccaga uauuggcaac uuugaucccu     60
cgguuuagcg ccggccuuuu cucccacacu uucacg                             96

<210> SEQ ID NO 42
<211> LENGTH: 96
<212> TYPE: RNA
```

```
<213> ORGANISM: Artificial Sequence
<220> FEATURE:
<223> OTHER INFORMATION: synthetic

<400> SEQUENCE: 42
gggaauugcc auguguaugu gggagacggu cggguccaga uauugggaaa uuucguggua    60
gguuuuguug cccguguuuc uacgauuacu uggguc                             96

<210> SEQ ID NO 43
<211> LENGTH: 96
<212> TYPE: RNA
<213> ORGANISM: Artificial Sequence
<220> FEATURE:
<223> OTHER INFORMATION: synthetic

<400> SEQUENCE: 43
gggaauugcc auguguaugu gggagacggu cggguccaga uauuggacau uuucgagaca    60 gcauuuuuc ccgaccuuug cggauuguau uuuagg                              96

<210> SEQ ID NO 44
<211> LENGTH: 96
<212> TYPE: RNA
<213> ORGANISM: Artificial Sequence
<220> FEATURE:
<223> OTHER INFORMATION: synthetic

<400> SEQUENCE: 44
gggaauugcc auguguaugu gggagacggu cggguccaga uauuggcgcu uuugaccuuc    60
ugcuuuaugu ccccuauuuc uuaaugacuu uggcc                              96

<210> SEQ ID NO 45
<211> LENGTH: 135
<212> TYPE: RNA
<213> ORGANISM: Artificial Sequence
<220> FEATURE:
<223> OTHER INFORMATION: synthetic

<400> SEQUENCE: 45
gggaauugcc auguguaugu gggagacggu cggguccaga uauuggaga uuuagucauu    60 aaguuuuaca auccgcuuug uaaucguagu uuguguuugc cauguguaug ugggagacgg   120
ucggguccag auauu                                                   135

<210> SEQ ID NO 46
<211> LENGTH: 123
<212> TYPE: RNA
<213> ORGANISM: Artificial Sequence
<220> FEATURE:
<223> OTHER INFORMATION: synthetic

<400> SEQUENCE: 46
gggaacguau cugucgagua gagugugggc ucccacauac ucugaugauc cuucgggauc    60
auucauggca acgugaaagu gugggagaaa aggccggcgc uaaaccgagg gaucaaaguu   120
gcc                                                                123

<210> SEQ ID NO 47
<211> LENGTH: 123
<212> TYPE: RNA
<213> ORGANISM: Artificial Sequence
<220> FEATURE:
<223> OTHER INFORMATION: synthetic

<400> SEQUENCE: 47
```

```
gggaacguau cgucgagua gagugugggc ucccacauac ucugaugauc cuucgggauc    60
auucauggca agaccaaagu aaucguagaa acacgggcaa caaaaccuac cacgaaauuu   120
ccc                                                                123

<210> SEQ ID NO 48
<211> LENGTH: 123
<212> TYPE: RNA
<213> ORGANISM: Artificial Sequence
<220> FEATURE:
<223> OTHER INFORMATION: synthetic

<400> SEQUENCE: 48
gggaacguau cugucgagua gagugugggc ucccacauac ucugaugauc cuucgggauc   60
auucauggca accuaaaaua caauccgcaa aggucgggaa aaaaugcugu cucgaaaaug  120
ucc                                                                123

<210> SEQ ID NO 49
<211> LENGTH: 123
<212> TYPE: RNA
<213> ORGANISM: Artificial Sequence
<220> FEATURE:
<223> OTHER INFORMATION: synthetic

<400> SEQUENCE: 49
gggaacguau cugucgagua gagugugggc ucccacauac ucugaugauc cuucgggauc   60
auucauggca aggccaaaag ucauuaagaa auaggggaca uaaagcagaa ggucaaaagc  120
gcc                                                                123

<210> SEQ ID NO 50
<211> LENGTH: 123
<212> TYPE: RNA
<213> ORGANISM: Artificial Sequence
<220> FEATURE:
<223> OTHER INFORMATION: synthetic

<400> SEQUENCE: 50
gggaacguau cugucgagua gagugugggc ucccacauac ucugaugauc cuucgggauc   60
auucauggca aacacaaacu acgauuacaa agcggauugu aaaacuuaau gacuaaaucu  120
ccc                                                                123

<210> SEQ ID NO 51
<211> LENGTH: 123
<212> TYPE: RNA
<213> ORGANISM: Artificial Sequence
<220> FEATURE:
<223> OTHER INFORMATION: synthetic

<400> SEQUENCE: 51
gggaacguau cugucgagua gagugugggc ucccacauac ucugaugauc cuucgggauc   60
auucauggca aucggaaaga ccuucugcaa acgagacagc aaaacguggu agguaaagau  120
ccc                                                                123

<210> SEQ ID NO 52
<211> LENGTH: 81
<212> TYPE: DNA
<213> ORGANISM: Artificial Sequence
<220> FEATURE:
<223> OTHER INFORMATION: artificial
```

<400> SEQUENCE: 52
cggtggtgca gatgaacttc agggtcattg gcaactttga tccctcggtt tagcgccggc    60
cttttctccc acactttcac g                                              81

<210> SEQ ID NO 53
<211> LENGTH: 81
<212> TYPE: DNA
<213> ORGANISM: Artificial Sequence
<220> FEATURE:
<223> OTHER INFORMATION: synthetic

<400> SEQUENCE: 53
cggtggtgca gatgaacttc agggtcattg ggaaatttcg tggtaggttt tgttgcccgt    60
gtttctacga ttactttggt c                                              81

<210> SEQ ID NO 54
<211> LENGTH: 81
<212> TYPE: DNA
<213> ORGANISM: Artificial Sequence
<220> FEATURE:
<223> OTHER INFORMATION: synthetic

<400> SEQUENCE: 54
cggtggtgca gatgaacttc agggtcattg gacatttcg agacagcatt ttttcccgac    60
ctttgcggat tgtattttag g                                              81

<210> SEQ ID NO 55
<211> LENGTH: 81
<212> TYPE: DNA
<213> ORGANISM: Artificial Sequence
<220> FEATURE:
<223> OTHER INFORMATION: synthetic

<400> SEQUENCE: 55
cggtggtgca gatgaacttc agggtcattg gcgcttttga ccttctgctt tatgtcccct    60
atttcttaat gactttggc c                                               81

<210> SEQ ID NO 56
<211> LENGTH: 81
<212> TYPE: DNA
<213> ORGANISM: Artificial Sequence
<220> FEATURE:
<223> OTHER INFORMATION: synthetic

<400> SEQUENCE: 56
cggtggtgca gatgaacttc agggtcattg ggagatttag tcattaagtt ttacaatccg    60
ctttgtaatc gtagtttgtg t                                              81

<210> SEQ ID NO 57
<211> LENGTH: 81
<212> TYPE: DNA
<213> ORGANISM: Artificial Sequence
<220> FEATURE:
<223> OTHER INFORMATION: synthetic

<400> SEQUENCE: 57
cggtggtgca gatgaacttc agggtcattg ggatctttac ctaccacgtt ttgctgtctc    60
gtttgcagaa ggtctttccg a                                              81

<210> SEQ ID NO 58
<211> LENGTH: 81

```
<212> TYPE: DNA
<213> ORGANISM: Artificial Sequence
<220> FEATURE:
<223> OTHER INFORMATION: synthetic

<400> SEQUENCE: 58
cgtgaaagtg tgggagaaaa ggccggcgct aaaccgaggg atcaaagttg ccaatgaccc    60
tgaagttcat ctgcaccacc g                                              81

<210> SEQ ID NO 59
<211> LENGTH: 81
<212> TYPE: DNA
<213> ORGANISM: Artificial Sequence
<220> FEATURE:
<223> OTHER INFORMATION: synthetic

<400> SEQUENCE: 59
gaccaaagta atcgtagaaa cacgggcaac aaaacctacc acgaaatttc ccaatgaccc    60
tgaagttcat ctgcaccacc g                                              81

<210> SEQ ID NO 60
<211> LENGTH: 81
<212> TYPE: DNA
<213> ORGANISM: Artificial Sequence
<220> FEATURE:
<223> OTHER INFORMATION: synthetic

<400> SEQUENCE: 60
cctaaaatac aatccgcaaa ggtcgggaaa aaatgctgtc tcgaaaatgt ccaatgaccc    60
tgaagttcat ctgcaccacc g                                              81

<210> SEQ ID NO 61
<211> LENGTH: 81
<212> TYPE: DNA
<213> ORGANISM: Artificial Sequence
<220> FEATURE:
<223> OTHER INFORMATION: synthetic

<400> SEQUENCE: 61
ggccaaaagt cattaagaaa tagggggacat aaagcagaag gtcaaaagcg ccaatgaccc   60
tgaagttcat ctgcaccacc g                                              81

<210> SEQ ID NO 62
<211> LENGTH: 81
<212> TYPE: DNA
<213> ORGANISM: Artificial Sequence
<220> FEATURE:
<223> OTHER INFORMATION: synthetic

<400> SEQUENCE: 62
acacaaacta cgattacaaa gcggattgta aaacttaatg actaaatctc ccaatgaccc    60
tgaagttcat ctgcaccacc g                                              81

<210> SEQ ID NO 63
<211> LENGTH: 81
<212> TYPE: DNA
<213> ORGANISM: Artificial Sequence
<220> FEATURE:
<223> OTHER INFORMATION: synthetic

<400> SEQUENCE: 63
tcggaaagac cttctgcaaa cgagacagca aaacgtggta ggtaaagatc ccaatgaccc    60
```
tgaagttcat ctgcaccacc g                                          81

<210> SEQ ID NO 64
<211> LENGTH: 25
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: wherein the adenine at position 1 is
      phosphorylated

<400> SEQUENCE: 64
acccugaagu ucaucugcac caccg                                      25

<210> SEQ ID NO 65
<211> LENGTH: 27
<212> TYPE: RNA
<213> ORGANISM: Artificial Sequence
<220> FEATURE:
<223> OTHER INFORMATION: synthetic

<400> SEQUENCE: 65
cgguggugca gaugaacuuc aggguca                                    27

<210> SEQ ID NO 66
<211> LENGTH: 25
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: wherein the adenine at position 1 is
      phosphorylated
<220> FEATURE:
<221> NAME/KEY: misc_feature
<222> LOCATION: (25)..(25)
<223> OTHER INFORMATION: wherein the guanine at position 25 is labeled
      with Alexa 488

<400> SEQUENCE: 66
acccugaagu ucaucugcac caccg                                      25

<210> SEQ ID NO 67
<211> LENGTH: 27
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: wherein the cytosine at position 1 is labeled
      with Alexa 546

<400> SEQUENCE: 67
cgguggugca gaugaacuuc aggguca                                    27

<210> SEQ ID NO 68
<211> LENGTH: 80
<212> TYPE: DNA
<213> ORGANISM: Artificial Sequence
<220> FEATURE:
<223> OTHER INFORMATION: synthetic

<400> SEQUENCE: 68
tcgtcattaa gcagctcgtt aatggtttgg caactttgat ccctcggttt agcgccggcc    60 tttctccca cactttcacg                                                 80

<210> SEQ ID NO 69
<211> LENGTH: 81
<212> TYPE: DNA
<213> ORGANISM: Artificial Sequence
<220> FEATURE:
<223> OTHER INFORMATION: synthetic

<400> SEQUENCE: 69
ctgcgacagc ttataatgga tgtactttg ggaaatttcg tggtaggttt tgttgcccgt    60
gtttctacga ttactttggt c                                              81

<210> SEQ ID NO 70
<211> LENGTH: 80
<212> TYPE: DNA
<213> ORGANISM: Artificial Sequence
<220> FEATURE:
<223> OTHER INFORMATION: synthetic

<400> SEQUENCE: 70
cgtgaaagtg tgggagaaaa ggccggcgct aaaccgaggg atcaaagttg ccaaaccatt    60
aacgagctgc ttaatgacga                                                80

<210> SEQ ID NO 71
<211> LENGTH: 81
<212> TYPE: DNA
<213> ORGANISM: Artificial Sequence
<220> FEATURE:
<223> OTHER INFORMATION: synthetic

<400> SEQUENCE: 71
gaccaaagta atcgtagaaa cacgggcaac aaaacctacc acgaaatttc ccaaaagtac    60
atccattata agctgtcgca g                                              81

<210> SEQ ID NO 72
<211> LENGTH: 25
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: wherein the cytosine at position 1 is
      phosphorylated

<400> SEQUENCE: 72
ccauuaacga gcugcuuaau gacga                                          25

<210> SEQ ID NO 73
<211> LENGTH: 27
<212> TYPE: RNA
<213> ORGANISM: Artificial Sequence
<220> FEATURE:
<223> OTHER INFORMATION: synthetic

<400> SEQUENCE: 73
ucgucauuaa gcagcucguu aaugguu                                        27

<210> SEQ ID NO 74
<211> LENGTH: 25

<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: wherein the guanine at position 1 is
      phosphorylated

<400> SEQUENCE: 74
guacauccau uauaagcugu cgcag                                          25

<210> SEQ ID NO 75
<211> LENGTH: 27
<212> TYPE: RNA
<213> ORGANISM: Artificial Sequence
<220> FEATURE:
<223> OTHER INFORMATION: synthetic

<400> SEQUENCE: 75
cugcgacagc uuauaaugga uguacuu                                        27

<210> SEQ ID NO 76
<211> LENGTH: 44
<212> TYPE: RNA
<213> ORGANISM: Artificial Sequence
<220> FEATURE:
<223> OTHER INFORMATION: synthetic

<400> SEQUENCE: 76
gggaaccguc cacugguucc cgcuacgaga gccugccucg uagc                     44

<210> SEQ ID NO 77
<211> LENGTH: 44
<212> TYPE: RNA
<213> ORGANISM: Artificial Sequence
<220> FEATURE:
<223> OTHER INFORMATION: synthetic

<400> SEQUENCE: 77
gggaaccgca ggcugguucc cgcuacgaga gaacgccucg uagc                     44

<210> SEQ ID NO 78
<211> LENGTH: 44
<212> TYPE: RNA
<213> ORGANISM: Artificial Sequence
<220> FEATURE:
<223> OTHER INFORMATION: synthetic

<400> SEQUENCE: 78
gggaaccgcg uucugguucc cgcuacgaga cgucuccucg uagc                     44

<210> SEQ ID NO 79
<211> LENGTH: 44
<212> TYPE: RNA
<213> ORGANISM: Artificial Sequence
<220> FEATURE:
<223> OTHER INFORMATION: synthetic

<400> SEQUENCE: 79
gggaaccgag acugguucc cgcuacgagu cguggucucg uagc                      44

<210> SEQ ID NO 80
<211> LENGTH: 44
<212> TYPE: RNA
<213> ORGANISM: Artificial Sequence

```
<220> FEATURE:
<223> OTHER INFORMATION: synthetic

<400> SEQUENCE: 80
gggaaccacc acgagguucc cgcuacgaga accauccucg uagc                    44

<210> SEQ ID NO 81
<211> LENGTH: 44
<212> TYPE: RNA
<213> ORGANISM: Artificial Sequence
<220> FEATURE:
<223> OTHER INFORMATION: synthetic

<400> SEQUENCE: 81
gggaaccgau gguugguucc cgcuacgaga guggaccucg uagc                    44

<210> SEQ ID NO 82
<211> LENGTH: 49
<212> TYPE: RNA
<213> ORGANISM: Artificial Sequence
<220> FEATURE:
<223> OTHER INFORMATION: synthetic

<400> SEQUENCE: 82
gggaagcuac gaggcaggcu cucguagcgg gaaccagugg acgguuccc               49

<210> SEQ ID NO 83
<211> LENGTH: 49
<212> TYPE: RNA
<213> ORGANISM: Artificial Sequence
<220> FEATURE:
<223> OTHER INFORMATION: synthetic

<400> SEQUENCE: 83
gggaagcuac gaggcguucu cucguagcgg gaaccagccu gcgguuccc               49

<210> SEQ ID NO 84
<211> LENGTH: 49
<212> TYPE: RNA
<213> ORGANISM: Artificial Sequence
<220> FEATURE:
<223> OTHER INFORMATION: synthetic

<400> SEQUENCE: 84
gggaagcuac gaggagacgu cucguagcgg gaaccagaac gcgguuccc               49

<210> SEQ ID NO 85
<211> LENGTH: 49
<212> TYPE: RNA
<213> ORGANISM: Artificial Sequence
<220> FEATURE:
<223> OTHER INFORMATION: synthetic

<400> SEQUENCE: 85
gggaagcuac gagaccacga cucguagcgg gaaccacguc ucgguuccc               49

<210> SEQ ID NO 86
<211> LENGTH: 49
<212> TYPE: RNA
<213> ORGANISM: Artificial Sequence
<220> FEATURE:
<223> OTHER INFORMATION: synthetic

<400> SEQUENCE: 86
gggaagcuac gaggaugguu cucguagcgg gaaccucgug gugguuccc               49
```

<210> SEQ ID NO 87
<211> LENGTH: 64
<212> TYPE: DNA
<213> ORGANISM: Artificial Sequence
<220> FEATURE:
<223> OTHER INFORMATION: synthetic

<400> SEQUENCE: 87
gctacgaggc aggctctcgt agcgggaacc agtggacggt tccctatagt gagtcgtatt    60
agaa                                                                 64

<210> SEQ ID NO 88
<211> LENGTH: 64
<212> TYPE: DNA
<213> ORGANISM: Artificial Sequence
<220> FEATURE:
<223> OTHER INFORMATION: synthetic

<400> SEQUENCE: 88
gctacgaggc gttctctcgt agcgggaacc agcctgcggt tccctatagt gagtcgtatt    60
agaa                                                                 64

<210> SEQ ID NO 89
<211> LENGTH: 64
<212> TYPE: DNA
<213> ORGANISM: Artificial Sequence
<220> FEATURE:
<223> OTHER INFORMATION: synthetic

<400> SEQUENCE: 89
gctacgagga gacgtctcgt agcgggaacc agaacgcggt tccctatagt gagtcgtatt    60
agaa                                                                 64

<210> SEQ ID NO 90
<211> LENGTH: 64
<212> TYPE: DNA
<213> ORGANISM: Artificial Sequence
<220> FEATURE:
<223> OTHER INFORMATION: synthetic

<400> SEQUENCE: 90
gctacgagac cacgactcgt agcgggaacc acgtctcggt tccctatagt gagtcgtatt    60
agaa                                                                 64

<210> SEQ ID NO 91
<211> LENGTH: 64
<212> TYPE: DNA
<213> ORGANISM: Artificial Sequence
<220> FEATURE:
<223> OTHER INFORMATION: synthetic

<400> SEQUENCE: 91
gctacgagga tggttctcgt agcgggaacc tcgtggtggt tccctatagt gagtcgtatt    60
agaa                                                                 64

<210> SEQ ID NO 92
<211> LENGTH: 64
<212> TYPE: DNA
<213> ORGANISM: Artificial Sequence
<220> FEATURE:
<223> OTHER INFORMATION: synthetic

<400> SEQUENCE: 92

```
gctacgaggt ccactctcgt agcgggaacc aaccatcggt tccctatagt gagtcgtatt        60
agaa                                                                      64
```

<210> SEQ ID NO 93
<211> LENGTH: 78
<212> TYPE: RNA
<213> ORGANISM: Artificial Sequence
<220> FEATURE:
<223> OTHER INFORMATION: synthetic

<400> SEQUENCE: 93

```
ggaugcuggu acuuugaaa cauuucgagu cgcgaggguu ucccaucgu uggcccguau         60 cgcguuuucu uaugaaga                                                       78
```

<210> SEQ ID NO 94
<211> LENGTH: 54
<212> TYPE: RNA
<213> ORGANISM: Artificial Sequence
<220> FEATURE:
<223> OTHER INFORMATION: synthetic

<400> SEQUENCE: 94

```
ggucgcgacc uucuuuuccc ucgcgacucg aaauguuucu uuucgagguc gccc             54
```

<210> SEQ ID NO 95
<211> LENGTH: 54
<212> TYPE: RNA
<213> ORGANISM: Artificial Sequence
<220> FEATURE:
<223> OTHER INFORMATION: synthetic

<400> SEQUENCE: 95

```
ggaucuuucg ccuuuucgcg auacgggcca acgaugggu uugaaggucg cgac              54
```

<210> SEQ ID NO 96
<211> LENGTH: 53
<212> TYPE: RNA
<213> ORGANISM: Artificial Sequence
<220> FEATURE:
<223> OTHER INFORMATION: synthetic

<400> SEQUENCE: 96

```
gggcgaccuc guuuuguacc agcauccucu ucauaaguuu uggcgaaaga ucc              53
```

<210> SEQ ID NO 97
<211> LENGTH: 78
<212> TYPE: DNA
<213> ORGANISM: Artificial Sequence
<220> FEATURE:
<223> OTHER INFORMATION: synthetic

<400> SEQUENCE: 97

```
ggatgctggt acttttgaaa catttcgagt cgcgagggtt tcccatcgt tggcccgtat        60 cgcgttttct tatgaaga                                                       78
```

<210> SEQ ID NO 98
<211> LENGTH: 54
<212> TYPE: DNA
<213> ORGANISM: Artificial Sequence
<220> FEATURE:
<223> OTHER INFORMATION: synthetic

<400> SEQUENCE: 98

-continued ggtcgcgacc ttcttttccc tcgcgactcg aaatgtttct tttcgaggtc gccc    54

<210> SEQ ID NO 99
<211> LENGTH: 54
<212> TYPE: DNA
<213> ORGANISM: Artificial Sequence
<220> FEATURE:
<223> OTHER INFORMATION: synthetic

<400> SEQUENCE: 99
ggatctttcg cctttttcgcg atacgggcca acgatgggtt ttgaaggtcg cgac    54

<210> SEQ ID NO 100
<211> LENGTH: 53
<212> TYPE: DNA
<213> ORGANISM: Artificial Sequence
<220> FEATURE:
<223> OTHER INFORMATION: synthetic

<400> SEQUENCE: 100
gggcgacctc gttttgtacc agcatcctct tcataagttt tggcgaaaga tcc    53

<210> SEQ ID NO 101
<211> LENGTH: 78
<212> TYPE: DNA
<213> ORGANISM: Artificial Sequence
<220> FEATURE:
<223> OTHER INFORMATION: synthetic

<400> SEQUENCE: 101
tcttcataag aaaaggcgat acgggccaac gatgggaaaa ccctcgcgac tcgaaatgtt    60
tcaaaagtac cagcatcc    78

<210> SEQ ID NO 102
<211> LENGTH: 54
<212> TYPE: DNA
<213> ORGANISM: Artificial Sequence
<220> FEATURE:
<223> OTHER INFORMATION: synthetic

<400> SEQUENCE: 102
gggcgacctc gaaagaaac atttcgagtc gcgagggaaa agaaggtcgc gacc    54

<210> SEQ ID NO 103
<211> LENGTH: 53
<212> TYPE: DNA
<213> ORGANISM: Artificial Sequence
<220> FEATURE:
<223> OTHER INFORMATION: synthetic

<400> SEQUENCE: 103
tcgcgacctt caaaacccat cgttggcccg tatcgccaaa acgcgaaaga tcc    53

<210> SEQ ID NO 104
<211> LENGTH: 52
<212> TYPE: DNA
<213> ORGANISM: Artificial Sequence
<220> FEATURE:
<223> OTHER INFORMATION: synthetic

<400> SEQUENCE: 104
gatctttcgc gaaaacttat gaagaggatg ctggtacaaa acgaggtcgc cc    52

<210> SEQ ID NO 105
<211> LENGTH: 5

```
<212> TYPE: DNA
<213> ORGANISM: Artificial Sequence
<220> FEATURE:
<223> OTHER INFORMATION: synthetic

<400> SEQUENCE: 105 gggaa                                                                    5
```